(12) United States Patent
Maresh et al.

(10) Patent No.: US 6,432,636 B1
(45) Date of Patent: *Aug. 13, 2002

(54) DIAGNOSTIC APPLICATIONS OF PERLECAN DOMAIN I SPLICE VARIANTS

(75) Inventors: Grace A. Maresh, River Ridge, LA (US); Alan D. Snow, Lynnwood, WA (US)

(73) Assignee: University of Washington, Seattle, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/918,428

(22) Filed: Aug. 26, 1997

Related U.S. Application Data
(60) Provisional application No. 60/025,030, filed on Aug. 26, 1996.

(51) Int. Cl.⁷ .......................... C12Q 1/68; C12Q 19/34; C07H 21/04; C07H 21/02
(52) U.S. Cl. .................. 435/6; 435/91.2; 536/23.5; 536/24.31; 536/24.33
(58) Field of Search .................. 435/6, 91.2; 536/23.5, 536/24.31, 24.33

(56) References Cited

PUBLICATIONS

Ailles et al. "Induction of Perlecan Gene Expression Precedes Amyloid Formation during Experimental Murine AA Amyloidogenesis," Laboratory Investigation, vol. 69, No. 4, pp. 443–448, 1993.

Cohen et al. "Structural Characterization of the Complete Human Perlecan Gene and Its Promoter," Proc. Natl. Acad. Sci. USA, vol. 90, pp. 10404–10408, 1993.

Dolan et al. "Identification and Sites in Domain I of Perlecan That Regulate Heparan Sulfate Synthesis," Journal of Bio. Chem., vol. 272, No. 7, pp. 4316–4322, Feb. 14, 1997.

Groffen et al. "Expression and Characterization of Human Perlecan Domains I and II Synthesized by Baculovirus–infected Insect Cells," European Journal of Biochem., vol. 241, pp. 827–834, 1996.

Murdoch et al. "Widespread Expression of Perlecan Proteoglycan in Basement Membranes and Extracellular Matrices of Human Tissues as Detected by a Novel Monoclonal Antibody Against Domain III and In Situ Hybridization," The Journal of Histochem. and Cytochem., vol. 42, No. 2, pp. 239–249, 1994.

Noonan et al. "Perlecan, the Large Low–density Proteoglycan of Basement Membranes: Structure and Variant Forms," Kidney International, vol. 43, pp. 53–60, 1993.

Sigma Chemical Company "Biochemicals Organic Compounds for Research and Diagnostic Reagents," Sigma Chemical Company, 1992, pp. 513 (see products entitled heparan sulfate).

Stryer, *Biochemsity,* W.H. Freeman and Company, San Francisco, 1981, pp. 13–16 and 512–513.

(List continued on next page.)

*Primary Examiner*—Carla J. Myers
(74) *Attorney, Agent, or Firm*—Patrick M. Dwyer

(57) ABSTRACT

An isolated polynucleotide that is a splice variant of perlecan formed by a partial or complete deletion of a number of exons within domain I of perlecan, the number of exons deleted from domain I numbering less than the number of exons in domain I. An isolated polynucleotide that is a splice variant of perlecan formed by an insertion of nucleotides within domain I of perlecan. A method of detection and/or quantitation of a splice variant of perlecan domain I gene in a sample, the method comprising making complimentary DNA (cDNA) from messenger RNA (mRNA) in the sample, amplifying portions of the cDNA corresponding to the perlecan gene or parts thereof and detecting and quantifying the amplified cDNA in order to detect or quantify the splice variant.

22 Claims, 22 Drawing Sheets-

OTHER PUBLICATIONS

Goedert et al. "Assembly of Miocrotubule–associated Protein Tau into Alzheimer–like Filaments Induced by Sulphated Glycosaminoglycans," Nature, vol. 383, pp. 550–553, Oct. 1996.

Maresh et al. "Detection and Quantitation of Perlecan mRNA Levels in Alzheimer's Disease and Normal Aged Hippocampus by Competitive Reverse Transcription–Polymerase Chain Reaction," J. Neurochem., vol. 67, No. 3, pp. 1132–1143, 1996.

Murdoch et al. "Primary Structure of the Human Heparan Sulfate Proteoglycan from Basement Membrane (HSPG2/Perlecan)," Journal of Bio. Chem., vol. 267, No. 12, pp. 8544–8557, Apr. 25, 1992.

Snow et al. "The Presence of Heparan Sulfate Proteoglycans in the Neuritic Plaques and Congophilic Angiopathy in Alzheimer's Disease," American Journal of Pathology, vol. 133, No. 3, pp. 456–463, Dec. 1988.

Snow et al. "Immunolocalization of Heparan Sulfate Proteoglycans to the Prion Protein Amyloid Plaques of Gerstmann–Straussler Syndrome, Creutzfeldt–Jakob Disease and Scrapie," Laboratory Investigation, vol. 63, No. 5, pp. 601–611, 1990.

Snow et al. "Proteoglycans in the Pathogenesis of Alzheimer's Disease and Other Amyloidoses," Neurobiology of Aging, vol. 10, pp. 481–497, 1989.

Snow et al. "Heparan Sulfate Proteoglycans in Diffuse Plaques of Hippocampus but Not of Cerebellum in Alzheimer's Disease Brain," American Journal of Pathology, vol. 144, No. 2, pp. 337–347, Feb. 1994.

Snow et al. "Differential Binding of Vascular Cell–Derived Proteoglycans (Perlecan, Biglycan, Decorin, and Versican) to the Beta–Amyloid Protein of Alzheimer's Disease," Archives of Biochemistry and Biophysics, vol. 320, No. 1, pp. 84–95 Jun. 20, 1995.

Brunden et al. "pH–Dependent Binding of Synthetic β–Amyloid Peptides to Glycosminoglycans," J. Neurochem., vol. 61, No. 6, pp. 2147–2154, 1993.

Snow et al. "An Important Role of Heparan Sulfate Proteoglycan (Perlecan) in a Model System for teh Deposition and Persistence of Fibrillar Aβ–Amyloid in Rat Brain," Neuron, vol. 12, pp. 219–234, Jan. 1994.

Gupta–Bansal et al. "Proteoglycan–Mediated Inhibition of Aβ Proteolysis," Journal of Bio. Chem., vol. 270, No. 31, pp. 18666–18671, 1995.

Snow et al. "Early Accumulation of Heparan Sulfate in Neurons and in the Beta–Amyloid Protein–Containing Lesions of Alzheimer's Disease and Down's Syndrome," American Journal of Pathology, vol. 137, No. 5, pp. 1253–1270, Nov. 1990.

Kallunki et al. "Human Basement Membrane Haparan Sulfate Proteoglycan Core Protein: A 467–kD Protein Containing Multiple Domains Resembling Elements of the Low Density Lipoprotein Receptor, Laminin, Neural Cell Adhesion Molecules, and Epidermal Growth Factor," Journal of Cell Biology, vol. 116, pp. 559–571, 1992.

Noonan et al. "The Complete Sequence of Perlecan, a Basement Membrane Heparan Sulphate Proteoglycan, Reveals Extensive Similarity with Laminin A Chain, Low Density Lipoprotein–Receptor, and the Neural Cell Adhesion Molecule," Journal of Bio. Chem., vol. 266, No. 34, pp. 22939–22947, Dec. 5, 1991.

Kato et al. "Basement Membrane Proteoglycan in Various Tissues: Characterization Using Monoclonal Antibodies to the Engelbreth–Holm–Swarm Mouse Tumor Low Density Heparan Sulfate Proteoglycan," Journal of Cell Biology, pp. 2203–2210, Jun. 1988.

Kokenyesi et al. "Formation of Heparan Sulfate or Chondroitin/Dermatan Sulfate on Recombinant Domain I of Moise Perlecan Expressed in Chinese Hamster Ovary Cells," Biochemical and Biophysical Research Communications, vol. 211, No. 1, pp. 262–267, Jun. 6, 1995.

Nochlin et al. "A Simple Method of Rapid Freezing Adequately Preserves Brain Tissue for Immunocytochemistry Light and Electron Microscopic Examination," Acta Neuropathol, vol. 86, pp. 645–650, 1993.

Jacob et al. "The 5' Splice Site: Phylogenetic Evolution and Variable Geometry of Association with U1RNA," Nucleic Acids Research, vol. 17, No. 6, pp. 2159–2180, 1989.

Jackson et al. "A Reappraisal of Non–Consensus mRNA Splice Sites," Nucleic Acids Research, vol. 19, No. 14, pp. 3795–3798, 1991.

Merrifield "Solid Phase Synthesis," Science, vol. 232, pp. 341–347, Apr. 18, 1986.

Fields et al. "Solid Phase Peptide Sythesis Utilizing 9–Fluorenylmethoxycarbonyl Amino Acids," Int. J.Peptide Protein Res., vol. 35, pp. 161–214, 1990.

Hampson et al. "Separation of Radiolabelled Glycosaminoglycan Oligosaccharides by Polyacrylamide–Gel Electrophoresis," Biochem. J., vol. 221, pp. 697–705, 1984.

Farach–Carson et al. "Extraction and Isolation of Glycoproteins and Proteoglycans," BioTechniques, vol. 7, No. 5, pp. 482–493, 1989.

Hovingh et al. "Differentially Expressed Patterns of Glycosaminoglycan Structure in Heparan Sulfate Proteoglycans and Free Chains," Eur. J. Biochem., vol. 211, pp. 771–779, 1993.

```
PerDI-v5  194  ...Exon2→
                  ..........AGAGACCGTCACAGCAAGCCAAATGCGCTGGACACA  229
                            ||||||||||||||||||||||||||||||||||
Perlecan  180  CTGCCTGAGGACATAGAGACCGTCACAGCAAGCCAAATGCGCTGGACACA  229

230  TTCGTACCTTTCTGATGATGAGGACATGCTGGCTGACAGCATCTCAGGAG  279
               ||||||||||||||||||||| |||||||||||||||||||||||||||
          230  TTCGTACCTTTCTGATGATGAGTACAGTCTGGCTGACAGCATCTCAGGAG  279

Exon3→                                      Exon4→
          280  ACGACCTGGGCAGTGGGCAGCCTGGGACGGGGACTTCCAGATGGTTTAT  329
               || |||||||||||||||| |||||||||||||||||||||||||||||
          280  ACGACCTGGGCAGTGGGCAGCCTGGGCAGCGGGACTTCCAGATGGTTTAT  329

330  TTCCGAGCCCTGGTGAATTTCACTCGCTCCATCGAGTACAGCCCTCAGCT  379
               |||||||||||||||||||||||||||||||||||||||||||||||||
          330  TTCCGAGCCCTGGTGAATTTCACTCGCTCCATCGAGTACAGCCCTCAGCT  379

380  GGAGGATGCAGGCTCCAGAGAGTTTCGAGAGGTGTCCGAGGCTGTGGTAG  429
               |||||||||||||||||||||||||||||||||||||||||||||||||
          380  GGAGGATGCAGGCTCCAGAGAGTTTCGAGAGGTGTCCGAGGCTGTGGTAG  429

430  ACACG........................................     434
               |||||
          430  ACACGCTGGAGTCGGAGTACTTGAAAATTCCCGAGAGACCAGTTGTCAGT  479

Exon5→                                Exon6→
          435  ..........GGAGCTGGAATGCCTGGGTTTTTGTGGAGCTCGATGT  470
                         ||||||||||||||||||||||||||||||||||||
          480  GTGGTGTTCATCAAGGAGCTGGATGCCTGGGTTTTTGTGGAGCTCGATGT  529

471  GG......   472
               ||
          530  GGGCTCGGAA   539
```

FIGURE 4B

```
                                                                                        Exon1→                                                                    Exon2→
 81  ATGGGCTGGCGGGCCCCGGGCGCGCTGCTGCTGCTGCTGCACGGGCGGCTGCTGGCGGTGACC
      M  G  W  R  A  P  G  A  L  L  L  L  L  H  G  R  L  L  A  V  T      23
                                                                                      ◆
150  CATGGGCTGAGGGCTACGATGGCTTGTCTCTGCCTGAGGACACAGAGACCGTCACAGCAAGCCAAATG
      H  G  L  R  A  Y  D  G  L  S  L  P  E  D  T  E  T  V  T  A  S  Q  M   46
                                                                                      Exon3→
219  CGCTGGACACATTCGTACCTTTCTGATGATGAGGACATGCTGGCTGACAGCATCTCAGGAGACGACCTG
      R  W  T  H  S  Y  L  S  D  D  E  D  M  L  A  D  S  I  S  G  D  D  L   69
                                                         Exon4→
288  GGCAGTGGGGACCTGGGCAGCGGGGACTTCCAGATGGTTTATTTCCGAGCCCTGGTGAATTTCACTCGC
      G  S  G  D  L  G  S  G  D  F  Q  M  V  Y  F  R  A  L  V  N  F  T  R   92

357  TCCATCGAGTACAGCCCTCAGCTGGAGGATGCAGCTCCAGAGAGTTTCGAGAGGTGTCCGAGGCTGTG
      S  I  E  Y  S  P  Q  L  E  D  A  G  S  R  E  F  R  E  V  S  E  A  V   115
                      Exon6→                                                    ◆
426  GTAGACACGGGAGCTGAGTGGCTGGGTTTTGTGAGCTGCGGAGCTCGATGTGGCTCCGAAGGGAATGCCGATGG
      V  D  T  G  A  G  W  L  G  F  C  G  A  R  C  G  L  R  R  R  E  C  G  W  138

495  TGCTCAGATTCAGGAGAGATGCTGCAGGTCATCTCCAGGCGCTCTGTGGCCTCCTACGTCACCTCTCC
      C  S  D  S  R  A  A  Q  G  H  L  Q  R  L  C  G  L  L  R  H  L  S     161
                                                                    Exon7→
564  CCAGGGGATTCCAGTTCCGACGCTGGGCACAGTGCCCCAGTTCCCAAGAGCTCCACGGAGGCCGAGTT
      P  G  I  P  V  P  T  P  G  H  S  A  P  V  P  K  S  L  H  G  G  R  V   184

633  TGCCCTGCCACAGCTACAATGA
      C  L  P  Q  L  Q  *      190
```

FIGURE 4C

```
PerDIv4-6.5  150 ..........................................CATGGGCTGAGGGCATACGA  169
                                                              ||||||||||||||||||||
Perlecan     120 CTGCTGCACGGGCGGCTGCTGCGGTGACCCATGGGCTGAGGGCATACGA  169

170 TGGCTTGTCTCTCGCCTGAGGACATAGAGACCGTCACAGCAAGCCAAATGC  219
                 ||||||||||||| ||||||||||||||||||||||||||||||||||||
             170 TGGCTTGTCTCTCGCCTGAGGACATAGAGACCGTCACAGCAAGCCAAATGC  219

220 GCTGGACACACATTCGTACCTTTCTGATGATGAGGACATGCTGGCTGACAGC  269
                 |||||||||||||||||||||||||||||||||| |||||||||||||||
             220 GCTGGACACACATTCGTACCTTTCTGATGATGAGTAGTACATGCTGGCTGACAGC  269
                 .Exon3→
             270 ATCTCAGGAGACGACCTGGGCAGTGGGCAGACCTGGGCAGCGGGACTTCCA  319
                 ||||||||||||||||||||||||||||||||||||||||||||||||||
             270 ATCTCAGGAGACGACCTGGGCAGTGGGCAGACCTGGGCAGCGGGACTTCCA  319
                 Exon4→
             320 GATGGTTTA..........................................  328
                 |||||||||
             320 GATGGTTTATTTCCGAGCCCTGGTGAATTTCACTCGCTCCATCGAGTACA  369

(236 bp removed)

..Exon6→
             329 ...............AGGAGATGCTGCTCAGGGTTCATCTCCAGCGGCTC  363
                                ||||||||||||||||| ||||||||||||||||
             556 ATGGTGCTCAGATTCAGGAGAGATGCTGCTCAGGG.TCATCTCCAGCGGCTC  598

364 TGTGGCCTCCTACGTCACCTCTCCCCAGG  392
                 |||||||||||||||||||||||||||||
             599 TGTGGCCTCCTACGTCACCTCTCCCCAGG  627
```

FIGURE 5B

```
    ..Exon2→          .                   .                   .                   .
150 CATGGGCTGAGGGCATACGATGGCTTGTCTCTGCCTGAGGACATAGAGACCGTCACAGCAAGCCAAATG                    46
    H  G  L  R  A  Y  D  G  L  S  L  P  E  D  I  E  T  V  T  A  S  Q  M
                                                                    .Exon3→
219 CGCTGGACACATTCGTACCTTTCTGATGATGAGGACATGCTGGCTGACAGCATCTCAGGAGACGACCTG                    69
    R  W  T  H  S  Y  L  S  D  D  E  D  M  L  A  D  S  I  S  G  D  D  L
              Exon4         ...Exon6→     .
288 GGCAGTGGGGACCTGGGCAGCGGGGACTTCCAGATGGTTTA  AGGAGATGCTGCTCAGGGTTCAT                       82
    G  S  G  D  L  G  S  G  D  F  Q  M  V  *

357 CTCCAGCGGCTCTGTGGCCTCCTACGTCACCTCTCCCCAGG
```

FIGURE 5C

```
PerDI+4a  150 ...Exon2→
              CATGGGCTGAGGGCCTACGATGGCTTGTCTCTGCCTGAGGACATAGAGAC  199
                  ||||||||||||||||||||||||||||||||||||||||||||||||
Perlecan  150 CATGGGCTGAGGGCATACGATGGCTTGTCTCTGCCTGAGGACATAGAGAC  199

200 CGTCACACAGCAAGCCAAATGCGCTGGACACATTCGTACCTTTCTGATGATG  249
              ||||||||||||||||||||||||||||||||||||||||||||||||||
          200 CGTCACACAGCAAGCCAAATGCGCTGGACACATTCGTACCTTTCTGATGATG  249

.Exon3→
          250 AGGACATGCTGGCTGACAGCATCTCAGGAGACGACCTGGGCAGTGGGGAC  299
              || |||||||||||||||||||||||||||||||||||||||||||||||
          250 AGTACATGCTGGCTGACAGCATCTCAGGAGACGACCTGGGCAGTGGGGAC  299

Exon4→
          300 CTGGGCAGCGGGGACTTCCAGATGGTTTATTCCGAGCCGGCTCAGGGCA  349
              |||||||||||||||||||||||||||||||||||||||
          300 CTGGGCAGCGGGGACTTCCAGATGGTTTATTCCGAGCC...........  338

350 GCCCCTGGGCCGCCCCGCCCGTGCTGGTGAATTTCACTCGCTCCATCGAGT  399
                                      ||||||||||||||||||||||||||
          339 .......................CTGGTGAATTTCACTCGCTCCATCGAGT  366

Exon5→
          400 ACAGCCCTCAGCTGGAGGATGCAGGCTCCAGAGAGTTTCGAGAGGTGTCC  449
              ||||||||||||||||||||||||||||||||||||||||||||||||
          367 ACAGCCCTCAGCTGGAGGATGCAGGCTCCAGAGAGTTTCGAGAGGTGTCC  416

450 GAGGCTGTGTGGTAGACACGCTGGAGTCGGAGTACTTGAAAATTCCCGGAGA  499
              ||||||||||||||||||||||||||||||||||||||||||||||||||
          417 GAGGCTGTGTGGTAGACACGCTGGAGTCGGAGTACTTGAAAATTCCCGGAGA  466

500 CCAGGTTGTCAGTGTGGTGTTCATCAA
              |||||||||||||||||||||||||||
          467 CCAGGTTGTCAGTGTGGTGTTCATCAA
```

FIGURE 6B

```
...Exon2→                                                                                        .
150 CATGGGCTGAGGGCCTACGATGGCTTGTCTCTGCCTGAGGACATAGAGACCGTCACAGCAAGCCAAATG              46
    H   G   L   R   A   Y   D   G   L   S   L   P   E   D   I   E   T   V   T   A   S   Q   M
                                                                .Exon3→
219 CGCTGGACACATTCGTACCTTTCTGATGATGAGGACATGCTGGCTGACAGCATCTCAGGAGACGACCTG              69
    R   W   T   H   S   Y   L   S   D   D   E   D   M   L   A   D   S   I   S   G   D   D   L
                      Exon4→
288 GGCAGTGGGGACCTGGGCAGCGGGGACTTCCAGATGGTTTATTTCCGAGCCGGCTCAGGGCAGCCCCTG              92
    G   S   G   D   L   G   S   G   D   F   Q   M   V   Y   F   R   A   G   S   G   Q   P   L
357 GGCCGCCCGCCCCGTGCTGGTGAATTTCACTCGCTCCATCGAGTACAGCCCTCAGCTGGAGGATGCAGGC              115
    G   R   P   P   P   V   L   V   N   F   T   R   S   I   E   Y   S   P   Q   L   E   D   A   G
                                                      Exon5→
426 TCCAGAGAGTTTCGAGAGGTGTCCGAGGCTGTGGTAGACACGCTGGAGTCGGAGTACTTGAAAATTCCC              138
    S   R   E   F   R   E   V   S   E   A   V   V   D   T   L   E   S   E   Y   L   K   I   P
495 GGAGACCAGGTTGTCAGTGTGGTGTTCATCAA                                                   149
    G   D   Q   V   V   S   V   V   F   I   K
```

FIGURE 6C

```
                                   Exon1→                     Exon2→
rDI+3a   150  ...Exon1...........................CATGGGCTGAGGGCATACGA  169
              ..........                           ||||||||||||||||||||
rlecan   120  CTGCTGCACGGGCGGCTGCTGGCGGTGACCCATGGGCTGAGGGCATACGA  169 rDI+3a   170  TGGCTTGTCTCTGCCTGAGGACATAGAGACCGTCACAGCAAGCCAAATGC  219
              ||||||||||||||||||||||||||||||||||||||||||||||||||
rlecan   170  TGGCTTGTCTCTGCCTGAGGACATAGAGACCGTCACAGCAAGCCAAATGC  219 rDI+3a   220  GCTGGACACATTCGTACCTTTCTGATGATGAGGACATGCTGGCTGACAGC  269
              ||||||||||||||||||||||||||||||||||||||||||||||||||
rlecan   220  GCTGGACACATTCGTACCTTTCTGATGATGAGTACATGCTGGCTGACAGC  269
                    Exon3→
rDI+3a   270  ATCTCAGGAGACGACCTGGGCAGTGGGACCTGGGCAGCGGGGACTTCCA   319
              |||||||||||||||||||||||||||||||||||||||||||||||||
rlecan   270  ATCTCAGGAGACGACCTGGGCAGTGGGACCTGGGCAGCGGGGACTTCCA   319 rDI+3a   320  GATGGGCTCAGGGCAGCCCCGCCCGGGCCGCCCCGCCCGTGGCTGGCATGATGG  369
              |||||||||
rlecan   320  GATGG..........................................        324
                                                   Exon4→
rDI+3a   370  TCTCGGAGCCTGATGAGGAGTCCCCTCATTTATTTCCGAGCCCTGGTG  419
                                                   ||||||||||||||||
rlecan   325  ..........................................TTTATTTCCGAGCCCTGGTG  344 rDI+3a   420  AATTTCACTCGCTCCATCGAGTACAGCCCTCAGCTGGAGGATGCAGGCTC  469
              ||||||||||||||||||||||||||||||||||||||||||||||||||
rlecan   345  AATTTCACTCGCTCCATCGAGTACAGCCCTCAGCTGGAGGATGCAGGCTC  394
                                                             Exon5→
rDI+3a   470  CAGAGAGTTTCGAGAGGTGTCCGAGGCTGTGGTAGACACGCTGGAGTCGG  519
              ||||||||||||||||||||||||||||||||||||||||||||||||||
rlecan   395  CAGAGAGTTTCGAGAGGTGTCCGAGGCTGTGGTAGACACGCTGGAGTCGG  444 rDI+3a   520  AGTACTTGA.........                               528
              |||||||||
rlecan   445  AGTACTTGAAAAATTCCCGAGACCAGGTTGTCAGTGTGTTCATCAA     493
```

FIGURE 7B

```
    ...Exon2→
150 CATGGGCTGAGGGCCATACGATGGCTTGTCTCTGCCTGAGGACATAGAGACCGTCACAGCAAGCCAAATG  46
    H  G  L  R  A  Y  D  G  L  S  L  P  E  D  I  E  T  V  T  A  S  Q  M
                                                              Exon3→
219 CGCTGGACACATTCGTACCTTTCTGATGATGAGGACATGCTGGCTGACAGCATCTCAGGAGACGACCTG  69
    R  W  T  H  S  Y  L  S  D  D  E  D  M  L  A  D  S  I  S̲  G  D  D  L
288 GGCAGTGGGGACCTGGGCAGCGGGGACTTCCAGATGGGCTCAGGGCAGCCCCCTCTGGGCCGCCCCGTG  92
    G  S̲  G  D  L  G  S̲  G  D  F  Q  M  G  S̲  G  Q  P  P  L  G  R  P  P  V
                                      Exon4→
357 GCTGGCGATGATGGTCTCGGAGCCTGATGAGGAGTCCCCTCTCATTTATTTCCGAGCCCTGGTGAATTTC  115
    A  G  M  M  V  S  E  P  D  E  E  S  P  L  I  Y  F  R  A  L  V  N  F
426 ACTCGCTCCATCGAGTACAGCCCCTCAGCTGGAGGATGCAGGCTCCAGAGAGTTTCGAGAGGTGTCCGAG  138
    T  R  S  I  E  Y  S  P  Q  L  E  D  A  G  S  R  E  F  R  E  V  S  E
                Exon5→
495 GCTGTGGTAGACACGCTGGAGTCGGAGTACTTGA  149
    A  V  V  D  T  L  E  S  E  Y  L
```

FIGURE 7C

```
        Exon1→                                                           Exon2→
  81  ATGGGGTGGCGGGCGCCGGGCGCTGCTGCTGGCGCTGCTGCTGCACGGGCGGCTGCTGGCGGTGACC
       M  G  W  R  A  P  G  A  L  L  L  A  L  L  L  H  G  R  L  L  A  V  T   23

150  CATGGGCTGAGGGCATACGATGGCTTGTCTCTGCCTGAGGACACAGAGACCGTCACAGCAAGCCAAATG
       H  G  L  R  A  Y  D  G  L  S  L  P  E  D  T  E  T  V  T  A  S  Q  M   46
                                                                       Exon3→
 219  CGCTGGACACATTCGTACCTTTCTGATGATGAGGACATGCTGGCTGACAGCATCTCAGGAGACGACCTG
       R  W  T  H  S  Y  L  S  D  D  E  D  M  L  A  D  S  I  S  G  D  D  L   69
                                            Exon4→
 288  GGCAGTGGGGACTTGGGCAGCGGGGACTTCCAGATGGTTTATTTCCGAGCCCTGGTGAATTTCACTCGC
       G  S  G  D  L  G  S  G  D  F  Q  M  V  Y  F  R  A  L  V  N  F  T  R   92

357  TCCATCGAGTACAGCCCCTCAGCTGGAGGATGCAGGTCCCAGAGAGTTTCGAGAGGTGTCCGAGGCTGTG
       S  I  E  Y  S  P  Q  L  E  D  A  G  S  R  E  F  R  E  V  S  E  A  V  115
        Exon6→
 426  GTAGACACGGGAGCTGGATGGCTGGGTTTTGTGAGCTCGATGTGGGCTCCGAAGGAATGCGGATGG
       V  D  T  G  A  G  W  L  G  F  C  G  A  R  C  G  L  R  R  M  C  G  W  138

495  TGCTCAGATTCAGGAGAGATGCTGCTCAGGTCATCTCAGGTCAGGGCCATCTGCAGCGTCTCTGTGGCCTCCTACGTCACCTCTCC
       C  S  D  S  G  D  A  A  Q  G  H  L  Q  R  L  C  G  L  L  R  H  L  S  161
                                                              Exon7→
 564  CCAGGGATTCCAGTTCCGAGTTCCCGGCACAGTGCCCTGGAGCCCCAGTTCCCAAGAGCCTGCACGGAGGCCGAGTT
       P  G  I  P  V  P  T  P  G  H  S  A  P  V  P  K  S  L  H  G  G  R  V  184

633  TGCCTGCCACAGCTACAATGA
       C  L  P  Q  L  Q  *  190

FIGURE 9
```

```
                      ...Exon2→
 150 CATGGGCTGAGGGCTCATACGATGGCTTGTCTCTGCCTGAGGACATAGAGACCGTCACAGCAAGCCAAATG
      H  G  L  R  A  Y  D  G  L  S  L  P  E  D  I  E  T  V  T  A  S  Q  M
                                                                    Exon3→
 219 CGCTGGACACATTCGTACCTTTCTGATGATGAGGACATGCTGGCTGACAGCATCTCAGGAGACGACCTG
      R  W  T  H  S  Y  L  S  D  D  E  D  M  L  A  D  S  I  S  G  D  D  L 288 GGCAGTGGGGACCTGGGCAGCGGGGACTTCCAGATGGGCAGCCCCCTGGGCCGCCCGCCCGTG
      G  S  G  D  L  G  S  G  D  F  Q  M  G  S  L  G  Q  P  L  G  R  P  P  V
                                                        Exon4→
 357 GCTGGGCATGATGGTCTCGGAGCCTGATGAGGAGTCCCCTCATTTATTTCCGAGCCCTGGTGAATTTC
      A  G  M  M  V  S  E  P  D  E  E  S  P  L  I  Y  F  R  A  L  V  N  F 426 ACTCGCTCCATCGAGTACAGCCCCTCAGCTGGAGGATGCAGGCTCCAGAGAGTTTCGAGAGGTGTCCGAG
      T  R  S  I  E  Y  S  P  Q  L  E  D  A  G  S  R  E  F  R  E  V  S  E
                 Exon5→
 495 GCTGTGGTAGACACGCTGGAGTCGGAGTACTTGA
      A  V  V  D  T  L  E  S  E  Y  L
```

FIGURE 11

Table 1. Hippocampal Tissue Samples Used for RT-PCR

| Autopsy # | Diagnosis | Age (years) | Sex | Post-Mortem Delay (hours) | Duration of Disease (years) |
|---|---|---|---|---|---|
| 87-092 | AD[a] | 92 | F | 3.92 | 9 |
| 88-099 | AD | 90 | F | 4.50 | 5 |
| 89-030 | AD | 101 | F | 9.42 | 12 |
| 89-082 | AD | 94 | M | 4.17 | 14 |
| 90-084 | AD | 90 | F | 4.00 | 15 |
| 90-110 | AD | 74 | M | 5.25 | 19 |
| 91-005 | AD | 69 | M | 4.75 | 6 |
| 91-010 | AD | 79 | F | 3.33 | 8 |
| 91-029 | AD | 88 | F | 7.50 | 14 |
| 91-080 | AD | 87 | F | 4.58 | 11 |
|  |  | $86.4 \pm 3.1$[b] |  | $5.1 \pm 0.6$[b] | $11.3 \pm 1.4$[b] |

| Autopsy # | Controls[c] (Cause of Death) | Age (years) | Sex | Post-Mortem Delay (hours) |
|---|---|---|---|---|
| 88-178 | CHF | 67 | M | 3.08 |
| 90-182 | CA | 77 | M | 11.25 |
| 91-124 | MI | 71 | F | 5.58 |
| 91-167 | CHF | 86 | M | 8.42 |
| 91-171 | HR | 75 | M | 5.75 |
| 92-003 | CHF, RF | 78 | M | 5.00 |
| 93-026 | CA | 78 | M | 3.50 |
| 93-119 | CA | 75 | M | 11.50 |
| 94-031 | PPU, DM | 86 | M | 5.25 |
| 94-088 | CA | 77 | F | 8.00 |
|  |  | $77.0 \pm 1.8$[b] |  | $6.7 \pm 0.9$[b] |

[a] AD, Alzheimer's Disease

[b] Mean ± Standard Error of the Mean

[c] Controls (Cause of Death): CA, Cancer; CHF, Congestive Heart Failure; DM, Diabetes Mellitus; HR, Hemorrhage; MI, Myocardial Infarction; PPU, Perforated Peptic Ulcer; RF, Renal Failure

FIGURE 13

TABLE 2 - List of Primers Used For RT-PCR

| | |
|---|---|
| FPerlDI | CATGGGCTGAGGGCATACG |
| RPerlDI | TGTGCCCAGGCGTCGGAAC |
| FPerlDIE | ACGAATTCCATGGGCTGAGGGCATACG |
| RPerlDIX | ACCTCGAGTGTGCCCAGGCGTCGGAAC |
| F2hPerlDI | CTGAGGACATAGAGACCGTC |
| RhPerEx4/6 | CATCCAGCTCCCGTGTCTAC |
| FhEx3/6.5 | CAGATGGTTTAAGGAGATGCTG |
| FhEx178 | CGCCCGTGGCTGGTGAATTTC |
| FhEx181 | GTCCCCTCTCATTTATTTCCGA |

FIGURE 14

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
         (A) LENGTH: 573 NUCLEOTIDES
         (B) TYPE: NUCLEIC ACID
         (C) STRANDEDNESS: SINGLE
         (D) TOPOLOGY: LINEAR (ii) MOLECULE TYPE:cDNA (xi) SEQUENCE DESCRIPTION: SEQ ID NO:1:

```
ATGGGGTGGC GGGCGCCGGG CGCGCTGCTG CTGGCGCTGC TGCTGCACGG          50

GCGGCTGCTG GCGGTGACCC ATGGGCTGAG GGCATACGAT GGCTTGTCTC         100
```

-continued

```
TGCCTGAGGA CACAGAGACC GTCACAGCAA GCCAAATGCG CTGGACACAT        150

TCGTACCTTT CTGATGATGA GGACATGCTG GCTGACAGCA TCTCAGGAGA        200

CGACCTGGGC AGTGGGGACC TGGGCAGCGG GGACTTCCAG ATGGTTTATT        250

TCCGAGCCCT GGTGAATTTC ACTCGCTCCA TCGAGTACAG CCCTCAGCTG        300

GAGGATGCAG CTCCAGAGA GTTTCGAGAG GTGTCCGAGG CTGTGGTAGA         350

CACGGGAGCT GGATGGCTGG GTTTTTGTGG AGCTCGATGT GGGCTCCGAA        400

GGGAATGCGG ATGGTGCTCA GATTCAGGAG ATGCTGCTCA GGGTCATCTC        450

CAGCGGCTCT GTGGCCTCCT ACGTCACCTC TCCCCAGGGA TTCCAGTTCC        500

GACGCCTGGG CACAGTGCCC CAGTTCCCAA GAGCCTGCAC GGAGGCCGAG        550

TTTGCCTGCC ACAGCTACAA TGA                                    573
```

(2) INFORMATION FOR SEQ ID NO:2:

(i) SEQUENCE CHARACTERISTICS:
        (A) LENGTH: 219 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:2:

```
    GGAGCT GGATGGCTGG GTTTTTGTGG AGCTCGATGT GGGCTCCGAA         46

GGGAATGCGG ATGGTGCTCA GATTCAGGAG ATGCTGCTCA GGGTCATCTC         96

CAGCGGCTCT GTGGCCTCCT ACGTCACCTC TCCCCAGGGA TTCCAGTTCC        146

GACGCCTGGG CACAGTGCCC CAGTTCCCAA GAGCCTGCAC GGAGGCCGAG        196

TTTGCCTGCC ACAGCTACAA TGA                                    219
```

(2) INFORMATION FOR SEQ ID NO:3:

(i) SEQUENCE CHARACTERISTICS:
        (A) LENGTH: 190 AMINO ACIDS
        (B) TYPE: AMINO ACID
        (C) STRANDEDNESS:
        (D) TOPOLOGY: LINEAR (ii) MOLECULE TYPE: PROTEIN (ix) FEATURE:
        (D) OTHER INFORMATION: AMINO ACID NUMBERING ACCORDING TO
            TRANSLATION OF GENBANK ACCESSION #M85289

(xi) SEQUENCE DESCRIPTION: SEQ ID NO:3:

```
Met Gly Trp Arg Ala Pro Gly Ala Leu Leu Ala Leu Leu Leu
1               5                  10                  15

His Gly Arg Leu Leu Ala Val Thr His Gly Leu Arg Ala Tyr Asp
                20                  25                  30

Gly Leu Ser Leu Pro Glu Asp Thr Glu Thr Val Thr Ala Ser Gln
                35                  40                  45

Met Arg Trp Thr His Ser Tyr Leu Ser Asp Asp Glu Asp Met Leu
                50                  55                  60

Ala Asp Ser Ile Ser Gly Asp Asp Leu Gly Ser Gly Asp Leu Gly
                65                  70                  75

Ser Gly Asp Phe Gln Met Val Tyr Phe Arg Ala Leu Val Asn Phe
                80                  85                  90
```

```
Thr Arg Ser Ile Glu Tyr Ser Pro Gln Leu Glu Asp Ala Gly Ser
            95                 100                 105

Arg Glu Phe Arg Glu Val Ser Glu Ala Val Val Asp Thr Gly Ala
            110                115                 120

Gly Trp Leu Gly Phe Cys Gly Ala Arg Cys Gly Leu Arg Arg Glu
            125                130                 135

Cys Gly Trp Cys Ser Asp Ser Gly Asp Ala Ala Gln Gly His Leu
            140                145                 150

Gln Arg Leu Cys Gly Leu Leu Arg His Leu Ser Pro Gly Ile Pro
            155                160                 165

Val Pro Thr Pro Gly His Ser Ala Pro Val Pro Lys Ser Leu His
            170                175                 180

Gly Gly Arg Val Cys Leu Pro Gln Leu Gln
            185                190

(2) INFORMATION FOR SEQ ID NO:4:

(i) SEQUENCE CHARACTERISTICS:
        (A) LENGTH: 72 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:4:

Gly Ala Gly Trp Leu Gly Phe Cys Gly Ala Arg Cys Gly Leu Arg
1               5                  10                  15

Arg Glu Cys Gly Trp Cys Ser Asp Ser Gly Asp Ala Ala Gln Gly
                20                 25                  30

His Leu Gln Arg Leu Cys Gly Leu Leu Arg His Leu Ser Pro Gly
                35                 40                  45

Ile Pro Val Pro Thr Pro Gly His Ser Ala Pro Val Pro Lys Ser
                50                 55                  60

Leu His Gly Gly Arg Val Cys Leu Pro Gln Leu Gln
                65                 70

(2) INFORMATION FOR SEQ ID NO:5:

(i) SEQUENCE CHARACTERISTICS:
        (A) LENGTH: 20 NUCLEOTIDES
        (B) TYPE: NUCLEIC ACIDS
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:5:

CATCCAGCTC CCGTGTCTAC                                         20

(2) INFORMATION FOR SEQ ID NO:6:

(i) SEQUENCE CHARACTERISTICS:
        (A) LENGTH: 312 NUCLEOTIDES
        (B) TYPE: NUCLEIC ACIDS
        (C) STRANDEDNESS: SINGLE
        (D) TOPOLOGY: LINEAR (ii) MOLECULE TYPE: cDNA (xi) SEQUENCE DESCRIPTION: SEQ ID NO:6:

ATGGGGTGGC GGGCGCCGGG CGCGCTGCTG CTGGCGCTGC TGCTGCACGG        50
```

```
GCGGCTGCTG GCGGTGACCC ATGGGCTGAG GGCATACGAT GGCTTGTCTC        100

TGCCTGAGGA CATAGAGACC GTCACAGCAA GCCARATGCG CTGGACACAT        150

TCGTACCTTT CTGATGATGA GGACATGCTG GCTGACAGCA TCTCAGGAGA        200

CGACCTGGGC AGTGGGGACC TGGGCAGCGG GGACTTCCAG ATGGTTTAAG        250

GAGATGCTGC TCAGGGTTCA TCTCCAGCGG CTCTGTGGCC TCCTACGTCA        300

CCTCTCCCCA GG                                                 312
```

(2) INFORMATION FOR SEQ ID NO:7:

(i) SEQUENCE CHARACTERISTICS:
        (A) LENGTH: 82 AMINO ACIDS
        (B) TYPE: AMINO ACID
        (C) STRANDEDNESS:
        (D) TOPOLOGY: LINEAR (ii) MOLECULE TYPE: PROTEIN (ix) FEATURE:
        (D) OTHER INFORMATION: AMINO ACID NUMBERING ACCORDING TO
            TRANSLATION OF GENBANK ACCESSION #M85289

(xi) SEQUENCE DESCRIPTION: SEQ ID NO:7:

```
Met Gly Trp Arg Ala Pro Gly Ala Leu Leu Ala Leu Leu Leu
1               5                   10                  15

His Gly Arg Leu Leu Ala Val Thr His Gly Leu Arg Ala Tyr Asp
                20                  25                  30

Gly Leu Ser Leu Pro Glu Asp Ile Glu Thr Val Thr Ala Ser Gln
                35                  40                  45

Met Arg Trp Thr His Ser Tyr Leu Ser Asp Asp Glu Asp Met Leu
                50                  55                  60

Ala Asp Ser Ile Ser Gly Asp Asp Leu Gly Ser Gly Asp Leu Gly
                65                  70                  75

Ser Gly Asp Phe Gln Met Val
                80
```

(2) INFORMATION FOR SEQ ID NO:8:

(i) SEQUENCE CHARACTERISTICS:
        (A) LENGTH: 22 NUCLEOTIDES
        (B) TYPE: NUCLEIC ACID
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:8:

```
CAGATGGTTT AAGGAGATGC TG                                      22
```

(2) INFORMATION FOR SEQ ID NO:9:

(i) SEQUENCE CHARACTERISTICS:
        (A) LENGTH: 33 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:9:

```
GGCTCAGGGC AGCCCCTGGG CCGCCCGCCC GTG                          33
```

(2) INFORMATION FOR SEQ ID NO:10:

(i) SEQUENCE CHARACTERISTICS:
        (A) LENGTH: 11 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:10:

Gly Ser Gly Gln Pro Leu Gly Arg Pro Pro Val
1               5                   10

(2) INFORMATION FOR SEQ ID NO:11:

(i) SEQUENCE CHARACTERISTICS:
        (A) LENGTH: 21 NUCLEOTIDES
        (B) TYPE: NUCLEIC ACIDS
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:11:

CGCCCGTGGC TGGTGAATTT C                                            21

(2) INFORMATION FOR SEQ ID NO:12:

(i) SEQUENCE CHARACTERISTICS:
        (A) LENGTH: 75 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:12:

GCTCAGGGCA GCCCCTGGGC CGCCCGCCCG TGGCTGGCAT GATGGTCTCG              50

GAGCCTGATG AGGAGTCCCC TCTCA                                        75

(2) INFORMATION FOR SEQ ID NO:13:

(i) SEQUENCE CHARACTERISTICS:
        (A) LENGTH: 26 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:13:

Gly Ser Gly Gln Pro Leu Gly Arg Pro Pro Val Ala Gly Met Met
1               5                   10                  15

Val Ser Glu Pro Asp Glu Glu Ser Pro Leu Ile
                20                  25

(2) INFORMATION FOR SEQ ID NO:14:

(i) SEQUENCE CHARACTERISTICS:
        (A) LENGTH: 21 NUCLEOTIDES
        (B) TYPE: NUCLEIC ACIDS
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:14:

GTCCCTCTCA TTTATTTCCG A                                            21

(2) INFORMATION FOR SEQ ID NO:15:

(i) SEQUENCE CHARACTERISTICS:
        (A) LENGTH: 17 AMINO ACIDS
        (B) TYPE: AMINO ACID
        (C) STRANDEDNESS: SINGLE
        (D) TOPOLOGY: LINEAR (ii) MOLECULE TYPE: PROTEIN (xi) SEQUENCE DESCRIPTION: SEQ ID NO:15:

```
Pro Thr Pro Gly His Ser Ala Pro Val Pro Lys Ser Leu His Gly
1               5                   10                  15
Gly Arg
```

(2) INFORMATION FOR SEQ ID NO:16:

(i) SEQUENCE CHARACTERISTICS:
        (A) LENGTH: 19 AMINO ACIDS
        (B) TYPE: AMINO ACID
        (C) STRANDEDNESS: SINGLE
        (D) TOPOLOGY: LINEAR (ii) MOLECULE TYPE: PROTEIN (xi) SEQUENCE DESCRIPTION: SEQ ID NO:16:

```
Gln Pro Leu Gly Arg Pro Pro Val Ala Gly Met Met Val Ser Glu
1               5                   10                  15
Pro Asp Glu Glu
```

(2) INFORMATION FOR SEQ ID NO:17:

(i) SEQUENCE CHARACTERISTICS:
        (A) LENGTH: 20 NUCLEOTIDES
        (B) TYPE: NUCLEIC ACIDS
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:17:

```
CTGAGGACAT AGAGACCGTC                                       20
```

(2) INFORMATION FOR SEQ ID NO:18:

(i) SEQUENCE CHARACTERISTICS:
        (A) LENGTH: 19 NUCLEOTIDES
        (B) TYPE: NUCLEIC ACID
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:18:

```
TGTGCCCAGG CGTCGGAAC                                        19
```

(2) INFORMATION FOR SEQ ID NO:19:

(i) SEQUENCE CHARACTERISTICS:
        (A) LENGTH: 19 NUCLEOTIDES
        (B) TYPE: NUCLEIC ACID
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:19:

```
TGTGCCCAGG CGTCGGAAC                                                    19
```

(2) INFORMATION FOR SEQ ID NO:20:

(i) SEQUENCE CHARACTERISTICS:
        (A) LENGTH: 19 NUCLEOTIDES
        (B) TYPE: NUCLEIC ACID
        (C) STRANDEDNESS: SINGLE
        (D) TOPOLOGY: LINEAR (ii) MOLECULE TYPE: OLIGONUCLEOTIDE PRIMER (xi) SEQUENCE DESCRIPTION: SEQ ID NO:20:

```
TGTGCCCAGG CGTCGGAAC                                                    19
```

DIAGNOSTIC APPLICATIONS OF PERLECAN DOMAIN I SPLICE VARIANTS

This application claims priority to US provisional application Ser. No. 60/025,030, filed Aug. 26 1996.

This invention relates to the discovery and identification of novel perlecan domain I splice variants and their utilization for the production of specific and unique perlecan domain I variant nucleotides, peptides, antibodies, and molecular biology probes for the diagnosis and therapeutic intervention of Alzheimer's disease and other amyloid diseases. In addition new animal models to effectively screen and identify potential therapeutic compounds for Alzheimer's disease and each of the amyloidoses are described.

BACKGROUND OF THE INVENTION

Alzheimer's disease is one of the so-called "amyloid diseases. The literature suggests that an interaction between an amyloid protein and a heparan sulfate proteoglycan, known as perlecan, is important in the pathogenesis of Alzheimer's and other amyloid diseases. A more detailed description of the amyloid diseases, Alzheimer's disease, heparan sulfate proteoglycans, and perlecan is contained in the "Detailed Description of the Invention".

What is not known is whether perlecan (or related macromolecules) present in the tissues of Alzheimer's disease and other amyloid disorders are altered, abnormal and/or different than normal. This is a very important and puzzling question which has, of yet, not been answered. Since perlecan is usually found throughout the body in various organs and tissues and is synthesized by a variety of different cells, is it possible that perlecan (or related macromolecules) may exist in different form(s) in tissues, amyloid deposits and/or neurofibrillary tangles of patients afflicted with Alzheimer's disease? Is it also possible that perlecan (or related macromolecules) may also exist in different form(s) in tissues and/or amyloid deposits of patients afflicted with any of the other amyloid diseases?

SUMMARY OF THE INVENTION

The present invention provides some answers to these questions and relates to the novel and surprising discovery that perlecan exists in unique splice variant forms which are the result of "deletion" or "addition" splicing in domain I of perlecan (the region normally containing the 3 GAG chains of perlecan). The splicing of perlecan domain I results in the production of unique amino acid sequences which usually contain a consensus sequence for an additional GAG chain attachment site (ie. Ser-Gly or Ser-Gly-Asp) creating new perlecan molecules that are predicted to have four or more GAG chains, instead of the three GAG chains found in normal perlecan. Two different anti-peptide polyclonal antibodies produced against unique peptide regions which occurred as a result of perlecan domain I splicing demonstrate the immunolocalization of perlecan domain I variants to either the neurofibrillary tangles (i.e. perlecan domain I exon 5 deletion variant detected using the "exon 5 deletion" antibody) or amyloid plaques (i.e. perlecan domain I variant exon 4a and/or perlecan domain I variant exon 3a using the "perlecan domain I inset" antibody) in Alzheimer's disease brain. Immunolocalization studies utilizing the polyclonal anti-peptide antibodies produced suggest that some of the perlecan domain I splice variant molecules discovered (ie. perlecan domain I exon 5 deletion) do not reside on basement membranes, as does normal perlecan, and therefore should be regarded as distinctly different from perlecan or "basement membrane heparan sulfate PGs". Therefore, the perlecan domain I splice variants identified in the invention are different than normal perlecan in that their are distinct differences in their 1) nucleotide sequence(s), 2) corresponding amino acid sequence(s), 3) number of predicted GAG chains, and 4) distribution in specific tissues. Since recent studies have suggested that heparan sulfate GAGs are primarily involved in amyloid fibril formation (Castillo et al, Soc. Neurosc. Abst. 22:1172, 1996 Abstract) and in the induction of neurofibrillary tangle formation (Goedert et al, Nature 383:550–553, 1996), the surprising discovery in this invention of unique perlecan domain I splice variants which may contain additional heparan sulfate GAG chains and which co-localize to amyloid plaques or neurofibrillary tangles, further implicate their importance in plaque and tangle pathogenesis in Alzheimer's disease. In addition, the presence of perlecan domain I splice variants in tissues outside the central nervous system, as discovered in this invention, also implicates these splice variants in other amyloid diseases which affect systemic organs and tissues.

The present invention identifies perlecan domain I splice variants and provides specific and unique perlecan domain I variant nucleotides, peptides, antibodies, and molecular biology probes for the diagnosis and therapeutic intervention of Alzheimer's disease and other amyloid diseases. In addition new animal models to effectively screen and identify potential therapeutic compounds for Alzheimer's disease and each of the amyloidoses are described.

FEATURES OF THE INVENTION

Perlecan is known to play important and pathogenetic roles in the amyloid diseases including contributing to the formation, deposition, accumulation and/or persistence of fibrillar amyloid deposits in each of the amyloid diseases. This invention relates to the identification and the utilization of newly identified splice variants of domain I of human perlecan. One or all of the splice variants described in the present invention are believed to play similar, if not more important pathogenetic roles in Alzheimer's and other amyloid diseases. The invention described herein concerns these perlecan domain I splice variants and their use for the diagnosis and therapeutic intervention for Alzheimer's disease and other amyloidoses.

A primary object of the present invention is to establish new diagnostic and therapeutic methods and applications for the amyloid diseases. The amyloid diseases include, but are not limited to, the amyloid associated with Alzheimer's disease and Down's syndrome (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

One object of the present invention is to utilize novel and specific primer sequences for the detection of perlecan domain I splice variants in human tissues using standard reverse transcription polymerase chain reaction (RT-PCR) methodology, knowledgeable to one skilled in the art.

Yet another object of the present invention is to use standard RT-PCR methodology, but utilizing the specific primers described herein, which will aid in the amplification of each of the perlecan domain I splice variants, for the ultimate detection of these splice variants in various human tissues, cells and/or cells in biological fluids. In addition, quantitative competitive RT-PCR techniques can be utilized (Maresh et al, *J. Neurochem.* 67:1132–1144, 1996) to determine quantitative differences in these specific variants in total RNA derived from human tissues, cells, white blood cells and/or cells in biological fluids. Changes in quantitative levels of these perlecan domain I splice variants will aid in the diagnosis and monitoring of prognosis of patients who demonstrate amyloid and concurrent perlecan domain I splice variant and/or perlecan accumulation in tissues as part of the pathological process observed in the amyloid diseases.

Another object of the invention is to provide polyclonal and/or monoclonal peptide antibodies which can be utilized in a number of in vitro assays to specifically detect the perlecan domain I splice variants in human tissues and/or biological fluids. Polyclonal or monoclonal antibodies made specifically against a peptide portion or fragment of any of the perlecan domain I splice variants described herein can be utilized to detect and quantify perlecan domain I splice variants in human tissues and/or biological fluids. A preferred embodiment are the polyclonal antibodies described herein (i.e. "exon 5 deletion" antibody and the "perlecan domain I insert" antibody) which are made against unique perlecan domain I sequences as a result of splicing. These antibodies can be made by administering the peptides in antigenic form to a suitable host. Polyclonal or monoclonal antibodies may be prepared by standard techniques by one skilled in the art.

Another object of the present invention is to use each of the perlecan domain I splice variant antibodies described herein for the detection and specific localization of each of the perlecan domain I splice variants in human tissues, cells, and/or cell culture using standard immunohistochemical techniques.

Yet another object of the present invention is to use the "exon 5 deletion" antibody to detect perlecan domain I variant exon 5 (PerDI-v5) as a specific indicator for the presence and extent of neurofibrillary tangles in brain by monitoring biological fluids including, but not limited to, cerebrospinal fluid, blood, serum, urine, saliva, sputum, and stool.

Yet another object of the present invention is to use the "exon 5 deletion" antibody to detect perlecan domain I variant exon 5 (PerDI-v5) as a specific indicator for the presence and progression of Alzheimer's disease and/or other amyloid diseases by monitoring biological fluids including, but not limited to, cerebrospinal fluid, blood, serum, urine, saliva, sputum, and stool.

Yet another object of the present invention is to use the "perlecan domain I insert" antibody to detect perlecan domain I variant exon 4a and/or perlecan domain I variant exon 3a as a specific indicator for the presence and extent of amyloid plaques in brain by monitoring biological fluids including, but not limited to, cerebrospinal fluid, blood, serum, urine, saliva, sputum, and stool.

Yet another object of the present invention is to use the "perlecan domain I insert" antibody to detect perlecan domain I variant exon 4a and/or perlecan domain I variant exon 3a as a specific indicator for the presence and progression of Alzheimer's disease and/or other amyloid diseases by monitoring biological fluids including, but not limited to, cerebrospinal fluid, blood, serum, urine, saliva, sputum, and stool.

Yet another object of the present invention is to provide a method which can evaluate a compound or potential therapeutic's ability to alter (diminish or eliminate) the affinity of a given amyloid protein (as described herein) or amyloid precursor protein, to perlecan domain I splice variant protein or perlecan domain I splice variant GAGs. By providing a method of identifying compounds which affect the binding of amyloid proteins, or amyloid precursor proteins to such perlecan domain I splice variant protein or perlecan domain I splice variant derived-GAGs or fragments thereof, the present invention is also useful in identifying compounds which can prevent or impair such binding interaction. Thus, compounds can be identified which specifically affect an event linked with the amyloid formation, amyloid deposition, and/or amyloid persistence condition associated with Alzheimer's disease and other amyloid diseases as described herein.

Yet another object of the present invention is to use antibodies generated which recognize each of the perlecan domain I splice variants for in vivo labelling; for example, with a radionucleotide, for radioimaging to be utilized for in vivo diagnosis, and/or for in vitro diagnosis. Preferred embodiments include, but are not limited to, the "exon 5 deletion" antibody and the "perlecan domain I insert" antibody described herein.

Yet another object of the present invention is to make use of peptides or fragments thereof which are specific against new and unique sequences of the perlecan domain I splice variants. These peptides or fragments thereof can be used as potential blocking therapeutics for the interaction of the perlecan domain I splice variants in a number of biological processes and diseases (such as in the amyloid diseases described herein).

Another object of the present invention is to use peptides or fragments thereof, in conjunction with polyclonal and/or monoclonal antibodies generated against these peptide fragments, using in vitro assays to detect potential perlecan domain I splice variant autoantibodies in human biological fluids. Specific assay systems can be utilized to not only detect the presence of autoantibodies against perlecan domain I splice variants in biological fluids, but also to monitor the progression of disease by following elevation or diminution of perlecan domain I splice variant autoantibody levels.

Yet another object of the invention is to utilize perlecan domain I splice variant antibodies to isolate the perlecan domain I splice variant proteins from tissues using procedures known to those in the art such as affinity column chromatography and immunoprecipitation methodology. Isolation of perlecan domain I splice variants from tissues will also allow one to further structurally characterize the GAG chains associated with said perlecan domain I splice variants. Therefore, another object of the invention is to utilize perlecan domain I splice variant derived-GAGs as described herein for use in diagnostic assays, therapeutic intervention and research purposes.

Yet another object of the invention is to make oligonucleotides utilizing the nucleotide sequences described herein, to be utilized as new molecular biological probes to detect perlecan domain I splice variants in human tissues by standard in situ hybridization techniques.

Another object of the present invention is to provide new animal models for the production, deposition, accumulation and/or persistence of fibrillar Aβ amyloid in brain as observed in Alzheimer's disease and Down's syndrome. These new animal models can also be used to effectively screen and identify new therapeutic agents that target fibrillar Aβ amyloid formation, deposition, accumulation and/or persistence in brain.

Yet another object of the present invention is to provide new animal models for the production, deposition, accumulation and/or persistence of fibrillar amyloid as observed in each of the other amyloidoses. This includes, but is not limited to, the amyloid associated with chro nic infl ammation, various forms of malignancy and Fanilial Mediterranean Fever (where in the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $beta_2$-rnicroglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin). These new animal models can also be used for the evaluation of candidate drugs and therapies for the prevention and treatment of the amyloidoses as referred to above.

Yet another object of the invention is to produce new transgenic animals that overexpress or knock-out a particular perlecan domain I splice variant in an effort to produce specific phenotypes associated with a number of diseases and/or pathological processes, including, but not limited to, Alzheimer's disease and/or other amyloid diseases.

Yet another object of the invention is to utilize specific perlecan domain I variant antibodies and/or molecular biology probes, described herein, for the detection of these splice variants in human tissues in the amyloid diseases.

These and other features and advantages of the present invention will become more fully apparent when the following detailed description of the invention is read in conjunction with the accompanying figures.

BRIEF DESCRIPTION OF THE DRAWINGS

The following drawings are illustrative of embodiments of the invention and are not meant to limit the scope of the invention.

FIG. 2A are the RT-PCR products analyzed on a 2% agarose gel stained with ethidium bromide. Standards are indicated at 506 and 298 base pairs. FIG. 2B is a Southern blot of the RT-PCR products probed with a digoxigenin-labeled cDNA consisting of perlecan domain I.

FIGS. 3A, 3C and 3E are ethidium bromide-stained 2% agarose gels of some of the individual plasmid clones obtained and cut with EcoRI and XhoI. FIGS. 3B, 3D and 3F are Southern blots of the clones probed with digoxigenin-labeled cDNA probes to perlecan domain I (ie. Dig-366). Sequencing of the potential perlecan domain I splice variants shown in FIGS. 3A and 3B-lane 4 was subsequently identified as perlecan domain I variant exon 5. Sequencing of the potential perlecan domain I splice variants shown in FIGS. 3C and 3D-lanes 1 and 6 were both subsequently identified as perlecan domain I variant exons 4–6.5. Sequencing of the potential perlecan domain I splice variants shown in FIGS. 3E and 3F-lanes 4 and 6 were subsequently identified as the perlecan domain I splice variant exons 4a and 3a, respectively. Arrow in FIGS. 3E and 3F (lane 1) shows the expected size of normal perlecan domain I (ie. ~503 base pairs).

FIG. 4B discloses the determined nucleic acid sequence of Perlecan Domain I variant exon 5 and compares it to the nucleic acid sequence of normal perlecan domain I (using the perlecan sequence numbers of Murdoch et al, *J. Biol. Chem.* 267:8544–8557, 1992; Genbank accession number M85289). The top line is Perlecan Domain I variant exon 5 and the bottom line is normal perlecan domain I.

FIG. 4C discloses the determined nucleic acid sequence of Perlecan Domain I variant exon 5 and its corresponding deduced amino acid sequence. The region sequenced from clone PerDI-v5is shown between the two black diamonds indicated. Underlining indicates Ser-Gly-Asp sequences which are potential sites for addition of glycosaminoglycan chains. Bold letter indicates areas of new sequence not found in normal human perlecan. * indicates a stop codon. The standard one letter abbreviation for amino acids is used throughout.

FIG. 5B discloses the determined nucleic acid sequence of Perlecan Domain I variant exons 4–6.5 and compares it to the nucleic acid sequence of normal perlecan domain I (using the perlecan sequence numbers of Murdoch, A.D. et al, *J. Biol. Chem.* 267:8544–8557, 1992; Genbank accession number M85289). The top line is Perlecan Domain I variant exons 4–6.5 and the bottom line is normal perlecan domain I.

FIG. 5C discloses the determined nucleic acid sequence of Perlecan Domain I variant exons 4–6.5 and its corresponding deduced amino acid sequence. Underlining indicates Ser-Gly sequences which are potential sites for addition of glycosaminoglycan chains. * indicates a stop codon. The standard one letter abbreviation for amino acids is used throughout.

FIG. 6B discloses the determined nucleic acid sequence of Perlecan Domain I variant exon 4a and compares it to the nucleic acid sequence of normal perlecan domain I (using the perlecan sequence numbers of Murdoch et al, *J. Biol. Chem.* 267:8544–8557, 1992; Genbank accession number M85289). The top line is Perlecan Domain I variant exon 4a and the bottom line is normal perlecan domain I. Bold letters indicate 33 new nucleotides of sequence not found in normal human perlecan.

FIG. 6C discloses the determined nucleic acid sequence of Perlecan Domain I variant exon 4a and its corresponding deduced amino acid sequence. Underlining indicates Ser-Gly sequences which are potential sites for addition of glycosaminoglycan chains. Bold letters indicate areas of new sequence not found in normal human perlecan. The standard one letter abbreviation for amino acids is used throughout.

FIG. 7B discloses the determined nucleic acid sequence of Perlecan Domain I variant exon 3a and compares it to the nucleic acid sequence of normal perlecan domain I (using the perlecan sequence numbers of Murdoch et al, *J. Biol. Chem.* 267:8544–8557, 1992; Genbank accession number M85289).The top line is Perlecan Domain I variant exon 3a and the bottom line is normal perlecan domain I. Bold letters indicate 75 new nucleotides of sequence not found in normal human perlecan.

FIG. 7C discloses the determined nucleic acid sequence of Perlecan Domain I variant exon 3a and its corresponding deduced amino acid sequence. Underlining indicates Ser-Gly sequences which are potential sites for addition of glycosaminoglycan chains. Bold letters indicate areas of new sequence not found in normal human perlecan. The standard one letter abbreviation for amino acids is used throughout.

FIG. 9 discloses the determined nucleic acid sequence of Perlecan Domain I variant exon 5 and its corresponding deduced amino acid sequence (also refer to FIG. 4C). The dark solid line depicts the region of new sequence which was used to generate a peptide antibody known as "exon 5 deletion" antibody. The 17 amino-acid peptide P-T-P-G-H-S-A-P-V-P-K-S-L-H-G-G-R (SEQ ID NO: 15)(with a cysteine residue added to the amino terminus for single-point, site-directed KLH conjugation) was used to generate a polyclonal antibody to specifically detect the exon 5 deletion variant (i.e. PerlDI-v5) in tissues and biological fluids.

FIG. 10A demonstrates numerous neurofibrillary tangles (arrowheads) in the pyramidal layer of the hippocampus in a patient with confirmed Alzheimer's disease, following staining with Congo red and viewing under polarized light. FIG. 10B demonstrates the "exon 5 deletion" antibody immunostaining of neurofibrillary tangles (arrowheads) in the pyramidal layer of the hippocampus from the same case (i.e. FIG. 10A). FIG. 10C is a higher magnification of the "exon 5 deletion" antibody immunostaining of neurofibrillary tangles (arrowheads) from FIG. 10B. FIG. 10D demonstrates "exon 5 deletion" immunostaining of neurofibrillary tangles (arrowheads) in the pyramidal layer of the hippocampus from another case of confirmed Alzheimer's disease.

FIG. 11 discloses the determined nucleic acid sequence of Perlecan Domain I variant exon 3a and its corresponding deduced amino acid sequence (also refer to FIG. 7C). The dark solid line depicts the region of new sequence which was used to generate a new peptide antibody known as "perlecan domain I insert" antibody. The 19 amino-acid peptide Q-P-L-G-R-P-P-V-A-G-M-M-V-S-E-P-D-E-E (SEQ ID NO: 16) (with a cysteine residue added to the amino terminus for single-point, site-directed KLH conjugation) was used to generate a polyclonal antibody to detect the Perlecan Domain I variant exon 4a (i.e. PerlDI+4a) and/or the Perlecan Domain I variant exon 3a (i.e. PerlDI+3a) in tissues and biological fluids.

FIG. 12A demonstrates immunostaining of numerous amyloid plaques (arrowheads) in the cortex of a patient with confirmed Alzheimer's disease using the monoclonal antibody 4G8, which recognizes the Alzheimer's Aβ protein. FIG. 12B demonstrates a higher magnification of two amyloid plaques (arrows) in an Alzheimer's disease brain immunostained with the anti-4G8 antibody (from FIG. 12A). FIG. 12C demonstrates the "perlecan domain I insert" antibody immunostaining of neurons (arrowheads) in the pyramidal layer of the hippocampus of a patient with confirmed Alzheimer's disease. FIG. 12D demonstrates "perlecan domain I insert" antibody immunostaining of numerous amyloid plaques (arrows) in the Alzheimer's disease hippocampus from the same case (as in FIGS. 12A–C).

FIG. 13 is Table 1 and lists the hippocampal tissue samples used for RT-PCR.

FIG. 14 is Table 2 and lists the primers used for RT-PCR.

DETAILED DESCRIPTION OF THE INVENTION

Figure 1:
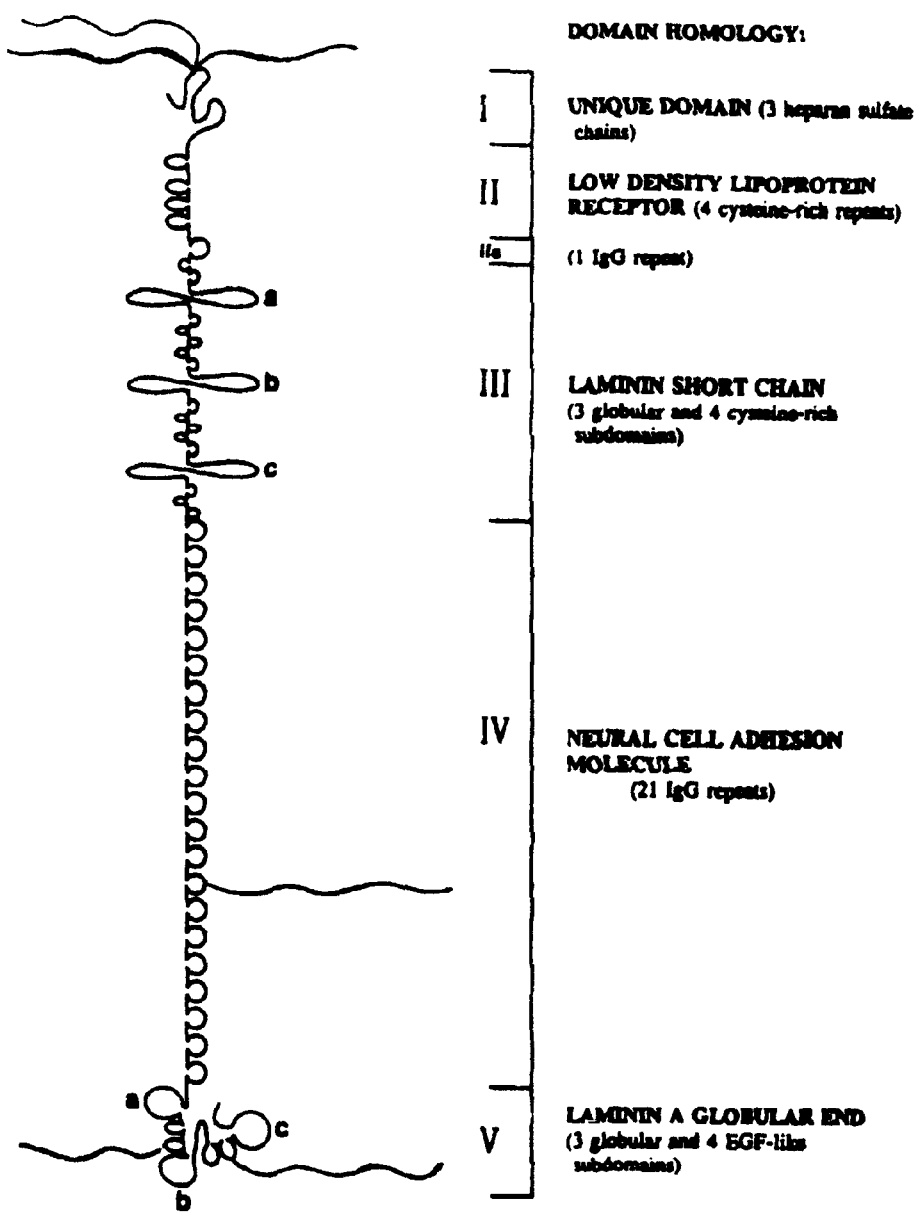
FIG. 1 is a schematic demonstrating the five structural domains of normal perlecan.

The following sections are provided by way of background to better appreciate the invention.

The Amyloid Diseases

The "amyloid diseases" consist of a group of clinically and generally unrelated human diseases which all demonstrate a marked accumulation in tissues of an insoluble extracellular substance known as "amyloid", and usually in an amount sufficient to impair normal organ function. Rokitansky in 1842 (Rokitansky, "*Handbuch der pathologischen Anatomie*", Vol. 3, Braumuller and Seidel, Vienna) was the first to observe waxy and amorphous looking tissue deposits in a number of tissues from different patients. However, it wasn't until 1854 when Virchow (Virchow, *Arch. Path. Anat.* 8:416, 1854) termed these deposits as "amyloid" meaning "starch-like" since they gave a positive staining with the sulfuric acid-iodine reaction, which was used in the 1850's for demonstrating cellulose. Although cellulose is not a constituent of amyloid, nonetheless, the staining that Virchow observed was probably due to the present of proteoglycans (PGs) which appear to be associated with all types of amyloid deposits. The name amyloid has remained despite the fact that Friederich and Kekule in 1859 discovered the protein nature of amyloid (Friedrich and Kekule, *Arch. Path. Anat. Physiol.* 16:50, 1859). For many years, based on the fact that all amyloids have the same staining and structural properties, lead to the postulate that a single pathogenetic mechanism was involved in amyloid deposition, and that amyloid deposits were thought to be composed of a single set of constituents. Current research has clearly shown that amyloid is not a uniform deposit and that amyloids may consist of different proteins which are totally unrelated (Glenner, *N. England J. Med.* 302:1283–1292, 1980).

Although the nature of the amyloid itself has been found to consist of completely different and unrelated proteins, all amyloids appear similar when viewed under the microscope due to amyloid's underlying protein structure to adapt into a fibrillar structure. All amyloids regardless of the nature of the underlying protein 1) stain characteristically with the Congo red dye and display a classic red/green birefringence when viewed under polarized light (Puchtler et al, *J. Histochem. Cytochem.* 10:355–364, 1962), 2) ultrastructurally consists of fibrils with a diameter of 7–10 nanometers and of indefinite length, 3) adopt a predominant beta-pleated sheet secondary structure. Thus, amyloid fibrils viewed under an electron microscope (30,000 times magnification) from the post-mortem brain of an Alzheimer's disease patient would look nearly identical to the appearance of amyloid present in a biopsied kidney from a rheumatoid arthritic patient. Both these amyloids would demonstrate a similar fibril diameter of 7–10 nanometers.

In the mid to late 1970's amyloid was clinically classified into 4 groups, primary amyloid, secondary amyloid, familial amyloid and isolated amyloid. Primary amyloid, is amyloid appearing de novo, without any preceding disorder. In 25–40% of these cases, primary amyloid was the antecedent of plasma cell dysfunction such as the development of multiple myeloma or other B-cell type malignancies. Here the amyloid appears before rather than after the overt malignancy. Secondary amyloid, appeared as a complication of a previously existing disorder. 10–15% of patients with multiple myeloma eventually develop amyloid (Hanada et al, *J. Histochem. Cytochem.* 19:1–15, 1971). Patients with rheumatoid arthritis, osteoarthritis, ankylosing spondylitis can develop secondary amyloidosis as with patients with tuberculosis, lung abscesses and osteomyelitis (Benson and Cohen, *Arth. Rheum.* 22:36–42, 1979; Kamei et al, *Acta Path. Jpn.* 32:123–133, 1982; McAdam et al, *Lancet* 2:572–575, 1975). Intravenous drug users who self-administer and who then develop chronic skin abscesses can also develop secondary amyloid (Novick, *Mt. Sin. J. Med.* 46:163–167, 1979). Secondary amyloid is also seen in patients with specific malignancies such as Hodgkin's disease and renal cell carcinoma (Husby et al, *Cancer Res.* 42:1600–1603, 1982). Although these were all initially classified as secondary amyloid, once the amyloid proteins were isolated and sequenced many of these turned out to contain different amyloid proteins.

The familial forms of amyloid also showed no uniformity in terms of the peptide responsible for the amyloid fibril deposited. Several geographic populations have now been identified with genetically inherited forms of amyloid. One group is found in Israel and this disorder is called Familial Mediterranean Fever and is characterized by amyloid deposition, along with recurrent inflammation and high fever (Mataxas, *Kidney* 20:676–685, 1981). Another form of inherited amyloid is Familial Amyloidotic Polyneuropathy, and has been found in Swedish (Skinner and Cohen, *Biochem. Biophys. Res. Comm.* 99:1326–1332, 1981), Portuguese (Saraiva et al, *J. Lab. Clin. Med.* 102:590–603, 1983; *J. Clin. Invest.* 74:104–119, 1984) and Japanese (Tawaraet al, *J. Lab. Clin. Med.* 98:811–822, 1981) nationalities. Amyloid deposition in this disease occurs predominantly in the peripheral and autonomic nerves. Hereditary amyloid angiopathy of Icelandic origin is an autosomal dominant form of amyloid deposition primarily affecting the vessels in the brain, and has been identified in a group of families found in Western Iceland (Jennson et al, *Clin. Genet.* 36:368–377, 1989). These patients clinically have massive cerebral hemorrhages in early life which usually causes death before the age of 40.

The primary, secondary and familial forms of amyloid described above tend to involve many organs of the body including heart, kidney, liver, spleen, gastrointestinal tract, skin, pancreas, and adrenal glands. These amyloid diseases are also referred to as "systemic amyloids" since so many organs within the body demonstrate amyloid accumulation. For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3 to 5 years.

Isolated forms of amyloid, on the other hand, tend to involve a single organ system. Isolated amyloid deposits have been found in the lung, and heart (Wright et al, *Lab. Invest.* 30:767–773, 1974; Pitkanen et al, *Am. J. Path.* 117:391–399, 1984). Up to 90% of type II diabetic patients (non-insulin dependent form of diabetes) have isolated amyloid deposits in the pancreas restricted to the beta cells in the islets of Langerhans (Johnson et al, *New Engl. J. Med.* 321:513–518, 1989; *Lab. Invest.* 66:522-535, 1992). Isolated forms of amyloid have also been found in endocrine tumors which secrete polypeptide hormones such as in medullary carcinoma of the thyroid (Butler and Khan, *Arch. Path. Lab. Med.* 110:647–649, 1986; Berger et al, *Virch. Arch. A Path. Anat. Hist.* 412:543–551, 1988). A serious complication of long term hemodialysis is amyloid deposited in the medial nerve and clinically associated with carpal tunnel syndrome (Gejyo et al, *Biochem. Biophys. Res. Comm.* 129:701–706, 1985; *Kidney Int.* 30:385–390, 1986). By far, the most common type and clinically relevant type of organ-specific amyloid, and amyloid in general, is that found in the brains of patients with Alzheimer's disease (see U.S.

Pat. No. 4,666,829 and Glenner and Wong, *Biochem. Biophys. Res. Comm.* 120:885–890, 1984; Masters et al, *Proc. Natl. Acad. Sci., USA* 82:4245–4249, 1985). In this disorder, amyloid is predominantly restricted to the central nervous system. Similar deposition of amyloid in the brain occurs in Down's syndrome patients once they reach the age of 35 years (Rumble et al, *New England J. Med.* 320:1446–1452, 1989; Mann et al, *Neurobiol. Aging* 10:397–399, 1989). Other types of central nervous system amyloid deposition include rare but highly infectious disorders known as the prion diseases which include Creutzfeldt-Jakob disease, Gerstmann-Straussler syndrome, and kuru (Gajdusek et al, *Science* 197:943–960, 1977; Prusiner et al, *Cell* 38:127–134, 1984; Prusiner, *Scientific American* 251:50–59, 1984; Prusiner et al, *Micr. Sc.* 2:33–39, 1985; Tateishi et al, *Ann. Neurol.* 24:35–40, 1988).

It was misleading to group the various amyloidotic disorders strictly on the basis of their clinical features, since when the major proteins involved were isolated and sequenced, they turned out to be different. For example, amyloid seen in rheumatoid arthritis and osteoarthritis, now known as AA amyloid, was the same amyloid protein identified in patients with the familial form of amyloid known as Familial Mediterranean Fever. Not to confuse the issue, it was decided that the best classification of amyloid should be according to the major protein found, once it was isolated, sequenced and identified.

Thus, amyloid today is classified according to the specific amyloid protein deposited. The amyloid diseases include, but are not limited to, the amyloid associated with Alzheimer's disease, Down's syndrome and hereditary cerebral hemorrhage with amyloidosis of the Dutch type (wherein the specific amyloid is now known as the beta-amyloid protein or A$\beta$), the amyloid associated with chronic inflammation, various forms of malignancy and Familial Mediterranean Fever (AA amyloid or inflammation-associated amyloidosis), the amyloid associated with multiple myeloma and other B-cell abnormalities (AL amyloid), the amyloid associated with type II diabetes (amylin or islet amyloid), the amyloid associated with the prion diseases including Creutzfeldt-Jakob disease, Gerstmann-Straussler syndrome, kuru and animal scrapie (PrP amyloid), the amyloid associated with long-term hemodialysis and carpal tunnel syndrome (beta$_2$-rnicroglobulin amyloid), the amyloid associated with senile cardiac amyloid and Familial Amyloidotic Polyneuropathy (prealbumin or transthyretin amyloid), and the amyloid associated with endocrine tumors such as medullary carcinoma of the thyroid (variants of procalcitonin).

Alzheimer's Disease

The most common form of amyloidosis is found in the brains of patients with Alzheimer's disease. Alzheimer's disease is the most common cause of dementia in middle and late life, and is manifested by progressive impairment of memory, language, visuospatial perceptions and behavior (*A Guide to the Understanding of Alzheimer's Disease and Related Disorders*, edited by Jorm, New York University Press, New York 1987). A diagnosis of probable Alzheimer's disease can be made on clinical criteria (usually by the exclusion of other diseases, memory tests etc), but a definite diagnosis requires the histological examination of specific abnormalities in the brain tissue usually obtained at autopsy.

In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease is characterized by the deposition and accumulation of a 39–43 amino acid peptide termed the beta-amyloid protein, A$\beta$ or $\beta$/A4 (Glenner and Wong, *Biochem. Biophys. Res. Comm.* 120:885–890, 1984; Masters et al, *Proc. Natl. Acad. Sci. USA* 82:4245–4249, 1985; Husby et al, *Bull. WHO* 71:105–108, 1993). This small peptide is a major component which makes up the amyloid deposits of neuritic "plaques" and in the walls of blood vessels (known as cerebrovascular amyloid deposits) in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). The pathological hallmarks of Alzheimer's disease is therefore the presence of "plaques" and "tangles", with amyloid being deposited in the central core of plaques and within the blood vessel walls. It is important to note that a so-called "normal aged brain" has some amyloid plaques and neurofibrillary tangles present. However, in comparison, an Alzheimer's disease brain shows an over abundance of plaques and tangles. Therefore, differentiation of an Alzheimer's disease brain from a normal brain from a diagnostic point of view is primarily based on quantitative assessment of "plaques" and "tangles".

In an Alzheimer's disease brain, are usually thousands of neuritic plaques. The neuritic plaques are made up of extracellular deposits consisting of an amyloid core usually surrounded by enlarged axons and synaptic terminals, known as neurites, and abnormal dendritic processes, as well as variable numbers of infiltrating microglia and surrounding astrocytes. The neurofibrillary tangles present in the Alzheimer's disease brain mainly consist of tau protein, which is a microtubule-associated protein (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science 251:675–678, 1991*). At the ultrastructural level, the tangle consists of paired helical filaments twisting like a ribbon, with a specific crossing over periodicity of 80 nanometers. In many instances within a neurofibrillary tangle, there are both paired helical filaments and straight filaments. In addition, many times the nerve cell will die, leaving the filaments behind. These tangles are known as "ghost tangles" since they are the filamentous remnants of the dead neuron.

The other major type of lesion found in the brain of an Alzheimer's disease patient is the accumulation of amyloid in the walls of blood vessels, both within the brain parenchyma and in the walls of the larger meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90, 1986; Pardridge et al, *J. Neurochem.* 49:1394–1401, 1987).

In addition, Alzheimer's disease patients demonstrate neuronal loss and synaptic loss. Furthermore, these patients also exhibit loss of neurotransmitters such as acetylcholine. Tacrine, the first FDA approved drug for Alzheimer's disease is a cholinesterase inhibitor (Cutler and Sramek, *New Engil. J. Med.* 328:808–810, 1993). However, this drug has showed limited success, if any, in the cognitive improvement in Alzheimer's disease patients and initially had major side effects such as liver toxicity.

For many years there has been an ongoing scientific debate as to the importance of "amyloid" in Alzheimer's disease and whether the "plaques" and "tangles" characteristic of this disease, were a cause or merely the consequences of the disease. Recent studies during the last few years have now implicated that amyloid is indeed a causative factor for Alzheimer's disease and not merely an innocent bystander. The Alzheimer's disease Aβ protein in cell culture has been shown to cause degeneration of nerve cells within short periods of time (Pike et al, *Br. Res.* 563:311–314, 1991; *J. Neurochem.* 64:253–265, 1994). Studies suggest that it is the fibrillar structure, a characteristic of all amyloids, that is responsible for the neurotoxic effects. The Aβ has also been found to be neurotoxic in slice cultures of hippocampus (the major memory region affected in Alzheimer's)(Harrigan et al, *Neurobiol. Aging* 16:779–789, 1995) and induces nerve cell death in transgenic mice (Games et al, *Nature* 373:523–527, 1995; Hsiao et al, *Neuron* 15:1203–1218, 1995). In addition, injection of the Alzheimer's Aβ into rat brain causes memory impairment and neuronal dysfunction (Flood et al, *Proc. Natl. Acad. Sci. U.S.A.* 88:3363–3366, 1991; *Br. Res.* 663:271–276, 1994), two additional hallmarks of Alzheimer's disease. Probably, the most convincing evidence that amyloid (ie. beta-amyloid protein) is directly involved in the pathogenesis of Alzheimer's disease comes from recent genetic studies. It has been discovered that the production of Aβ can result from mutations in the gene encoding, its precursor, known as the beta-amyloid precursor protein (Van Broeckhoven et al, *Science* 248:1120–1122, 1990; *Europ. Neurol.* 35:8–19, 1995; Murrell et al, *Science* 254:97–99, 1991; Haass et al, *Nature Med.* 1:1291–1296, 1995). This precursor protein when normally processed only usually produces very little of the toxic Aβ. The identification of mutations in the amyloid precursor protein gene which causes familial, early onset Alzheimer's disease is the strongest argument that amyloid is central to the pathogenetic process underlying this disease. Four reported disease-causing mutations have now been discovered which demonstrate the importance of the beta-amyloid protein in causing familial Alzheimer's disease (reviewed in Hardy, *Nature Genet.* 1:233–234, 1992). These studies suggest that providing a drug to reduce, eliminate or prevent fibrillar beta-amyloid protein formation, deposition, accumulation and/or persistence in the brains of human patients should be considered an effective therapeutic.

Proteoglycans

Proteoglycans (PGs) are a group of complex macromolecules which are found in all organs and tissues, intracellularly in a variety of different cell types, or extracellularly in the matrix where they are exported for a variety of functions. Proteoglycans consist of a linear protein core backbone to which one or more glycosaminoglycan (GAG) chains are covalently linked (Hascall and Hascall, in *Cell Biology of the Extracellular Matrix*, Hay editor, New York, Plenum Press, pp. 39, 1981; Hassell et al, Ann. Rev. Biochem. 55:539–567, 1986). The highly anionic GAG chains consist of repeating disaccharine units, containing 1) hexosamine (either D-glucosamine or D-galactosamine), and 2) hexuronic acid (either D-glucuronic acid or L-iduronic acid) (Muir, *Am. J. Med.* 47:673–690, 1969). The PGs are traditionally named according to the identification of the primary GAG present and several major GAGs have been identified. These are hyaluronic acid, heparan sulfate, heparin, chondroitin-4-sulfate, chondroitin-6-sulfate, dermatan sulfate and keratan sulfate. Usually the linkage between the GAG chains and the protein core backbone consists of a xylose-galactose-galactose attachment region with the xylose molecule covalently linked to the hydroxyl groups of a serine residue on the protein core (Roden and Armand, *J. Biol. Chem.* 241:65–70, 1966). The exception is hyaluronic acid which has a backbone consisting of alternating D-glucuronic acid and D-glucosamine units with no protein component. Keratan sulfate is the one PG which lacks the typical xylose-serine linkage. It is linked to protein either via a N-acetylgalactosamine residue linked to either serine or threonine (in cartilage) or via a N-acetylglucosamine residue attached directly to an asparagine residue (in comea) (Hascall and Hascall, in *Cell Biology of the Extracellular Matrix*, Hay editor, New York, Plenum Press, pp. 39, 1981; Muir, Am. J. Med. 47:673–690, 1969).

Heparan Sulfate Proteoglycans: A Common Component of All Amyloids

A major question that persisted in amyloid research was: why do all amyloids containing unrelated proteins all form an amyloid fibril with similar characteristics (ie. all consist of fibrils of 7–10 nm and contain a predominant beta-pleated sheet secondary structure)? Is there a common component that may play a similar role in the pathogenesis of all amyloids?

The answer to this question is important in understanding the mechanisms involved in amyloid diseases. Early studies demonstrated that highly sulfated GAGs (later determined to be specific heparan sulfate PGs) were concurrently deposited with inflammation-associated amyloid (ie. AA amyloid) in a well-defined experimental mouse model (Snow et al, *Lab. Invest.* 56:665–675, 1987). Later studies demonstrated that heparan sulfate PGs were temporally and structurally associated with the deposition and accumulation of AA amyloid in a variety of different tissues (Snow et al, *J. Histochem. Cytochem.* 39:1321–1330, 1991). Specific staining techniques and immunohistochemical methods then determined that highly sulfated PGs were a common feature of most, if not all, amyloids, independent of the specific amyloid protein involved, the stage of the amyloid disease, and the tissue site of amyloid deposition (Snow et al, *Lab. Invest.* 56:120–123, 1987; *Am. J. Path.* 133:456–463, 1988; *Acta Neuropath.* 77:337–342, 1990; *Lab. Invest.* 63:601–611, 1990).

Studies were pursued to further try to understand the potential involvement of specific PGs in Alzheimer's disease amyloidosis. In initial studies using specific immunohistochemical probes it was first determined that heparan sulfate PGs were an important constituent of amyloid in neuritic plaques and cerebrovascular amyloid deposits (Snow et al, *Am. J. Path.* 133:456–463, 1988). It was later revealed that the antibodies employed for this initial study were in fact those that specifically recognized the core protein of a large heparan sulfate PG, known as "perlecan". Heparan sulfate PGs (and specifically perlecan) were also co-localized to prion protein (PrP) amyloid plaques in Gerstmann-Straussler syndrome, Creutzfeldt-Jakob disease, kuru and animal scrapie (Snow et al, *Lab. Invest.* 63:601–611, 1990). Subsequent studies demonstrated that heparan sulfate PGs were also immunolocalized to the neurofibrillary tangles of Alzheimer's disease (Perry et al, *J. Neurosc.* 11:3679–3683, 1991).

These studies led to the hypothesis that specific heparan sulfate PGs played important roles in amyloidosis by 1) influencing amyloidogenic proteins to adapt predominantly beta-pleated sheet structures (i.e. indicative of amyloid), 2)

determining the anatomical location of amyloid deposition, and 3) contributing to the stability of amyloid and its inaccessibility to proteolytic degradation in tissues, thus not allowing the body to properly degrade and remove unwanted amyloid deposits (Snow and Wight, *Neurobiol. Aging* 10:481–497, 1989).

The Importance of Heparan Sulfate Proteoglycans in Alzheimer's Disease

Heparan sulfate PGs were postulated to play a primary role in the pathogenesis of Alzheimer's disease amyloidosis, as well as in other types of central nervous system and systemic amyloidoses (reviewed in Snow and Wight, *Neurobiol. Aging* 10:481–497, 1989). Only heparan sulfate PGs were found immunolocalized to all three major lesions (ie. neuritic plaques, neurofibrillary tangles and cerebrovascular amyloid deposits) in Alzheimer's disease brain and specifically to the A$\beta$-containing amyloid fibrils in both amyloid plaques and congophilic angiopathy (Snow et al, *Am. J. Path.* 133:456–463, 1988; Snow and Wight, *Neurobiol. Aging*, 10:481–497, 1989; Perlmutter and Chui, *Brain Res. Bull.* 24:677–686, 1990; Snow et al, *Am. J. Path.* 137:1253–1270, 1990; Su et al, *Neuroscience* 51:801–813, 1992; Van Gool et al, *Dementia* 4:308–314, 1993). Accumulating evidence suggested that perlecan was a major heparan sulfate PG present within the A$\beta$-containing amyloid deposits in Alzheimer's disease (Snow et al, *Am. J. Path.* 133:456–463, 1988; Snow and Wight, *Neurobiol. Aging*, 10:481–497, 1989; Snow et al, *Am. J. Path.* 137:1253–1270, 1990; Snow et al, *Am. J. Path.* 144:337–347, 1994) and may play a primary role in A$\beta$ fibril formation, deposition, accumulation and persistence. The consistent co-localization of perlecan to A$\beta$ deposits which existed in both a fibrillar and non-fibrillar form (Snow et al, *Am. J. Path.* 144:337–347, 1994) was probably due to perlecan's high affinity interactions with A$\beta$ (Snow et al, *J. Neuropath. Exp. Neurol.* 48:352, 1989 Abstract; Buee et al, *Brain Res.* 601:154–163, 1993; Buee et al, *Brain Res.* 627:199–204, 1993; Snow et al, *Arch. Biochem. Biophys.* 320:84–95, 1995) and with beta-amyloid precursor proteins (Narindrasorasak et al, *J. Biol. Chem.* 266:12878–12883, 1991). Residues 13–16 of A$\beta$ have been identified as a perlecan binding site (Snow et al, *J. Neuropath. Exp. Neurol.* 48:352, 1989 Abstract; Brunden et al, *J. Neurochem.* 61:2147–2154, 1993; Snow et al, *Arch. Biochem. Biophys.* 320:84–95, 1995). This region contained a heparin/heparan sulfate binding consensus sequence (Cardin and Weintraub, *Arterioscl.* 9:21–32, 1989), and is adjacent to the postulated alpha-secretase cleavage site on A$\beta$ (at Lys-16). Once bound, perlecan was believed to influence the secondary structure and/or aggregation properties of A$\beta$ and/or beta-amyloid precursor proteins (Fraser et al, *J. Neurochem.* 59:1531–1540, 1992). Perlecan also appeared to play a role in stabilizing fibrillar A$\beta$ amyloid when deposited in vivo (Snow et al, *Neuron* 12:219–234, 1994; Snow et al, *Soc. Neurosc. Abst.* 21:1292, 1995 Abstract), and protected A$\beta$ from degradation by proteases as recently demonstrated in vitro (Gupta-Bansal et al, *J. Biol. Chem.* 270:18666–18671, 1995). The combined results described above suggested that perlecan may be an important macromolecule, implicated at several key steps in the pathogenesis of A$\beta$ amyloidosis in AD.

Perlecan and/or heparan sulfate PG accumulation in conjunction with a variety of different amyloid proteins also appeared to be an early event, and did not appear to merely represent secondary and non-specific deposition. In experimental inflammation-associated amyloidosis, perlecan expression actually preceded AA amyloid deposition (Ailles et al, *Lab. Invest.* 69:443–447, 1993) suggesting that up-regulation of specific PGs may be an initiating event leading to eventual amyloid formation and/or deposition. In a previous study (Snow et al, *Am. J. Path.* 137:1253–1270, 1990), the brains of Down's syndrome patients (aged 1 day to 51 years) were examined to determine the possible sequence of events leading to A$\beta$ and PG deposition. Down's syndrome patients, who were completely devoid of any A$\beta$ immunoreactivity, demonstrated prominent heparan sulfate immunoreactivity in neurons as early as 1 day after birth, which was not observed in similar aged-matched non-Down's syndrome brains. In older patients, aged 18 and 24 years, diffuse A$\beta$ immunoreactivity (which was Congo red negative and therefore suggestive of non-fibrillar deposits) in the extracellular matrix was accompanied by co-localized heparan sulfate deposition. In patients, over the age of 35 years, fibrillar A$\beta$ deposits in neuritic plaques and cerebrovascular amyloid accumulation were also observed with co-localized heparan sulfate immunoreactivity. This study suggested that heparan sulfate accumulation within neurons may be a primary event eventually leading to the co-accumulation of heparan sulfate and A$\beta$ in the extracellular matrix. It was feasible that once the interaction between heparan sulfate and A$\beta$ (or its precursor protein) took place, a cascade of events occurred which led to fibril formation, deposition and eventual persistence.

DNA Sequences and Structure of Normal Perlecan

Perlecan is a single copy gene consisting of 94 exons with the predicted perlecan core protein sequence having a molecular mass of 467 kilodaltons in humans (Kallunki and Tryggvason, *J. Cell Biol.* 116:559–571, 1992; Murdoch et al, *J. Biol. Chem.* 267: 8544–8557, 1992). Domain I of perlecan, which is encoded by 5 exons (numbered 2 to 6) is postulated to contain three heparan sulfate GAG attachment sites (FIG. 1) and is unique to perlecan showing no homology to other known sequences.

The DNA sequence for normal human perlecan encodes a protein core with a molecular mass of approximately 467 kilodaltons (Murdoch et al, *J. Biol. Chem.* 267:8544–8557, 1992) whereas the DNA sequence for mouse perlecan encodes a protein core with a molecular mass of approximately 396 kilodaltons (Noonan et al, *J. Biol. Chem.* 266:22939–22947, 1991). A schematic demonstrating the five structural domains of perlecan is shown in FIG. 1. Perlecan, for all purposes of the present invention, has been also referred to as a basement membrane heparan sulfate PG, and/or a heparan sulfate PG of basement membranes (Kato et al, *J. Cell Biol.* 106:2203–2210, 1988). The genes for human (Murdoch et al, *J. Biol. Chem.* 267:8544–8557, 1992; Kallunki and Tryggvason, *J. Cell Biol.* 116:559–571, 1992) and mouse (Noonan et al, *J. Biol. Chem.* 266:22939–22947, 1991) perlecan have been cloned and the predicted core protein consists of five distinct domains (FIG. 1). Domain I contains the proposed heparan sulfate GAG attachment sites and is unique to perlecan showing no similarity to other known protein sequences. The location of the three Ser-Gly consensus heparan sulfate GAG attachment sites at the N-terminus corresponds with the number and position of known GAG chains (Kokenyesi and Silbert, *Biochem. Biophys. Res. Comm.* 211: 262–267, 1995). Domain II is homologous to the LDL binding domain present in the LDL-receptor, whereas Domain III has homology to the globule-rod regions of the laminin short arms. Domain IV is a highly repetitive region with numerous immunoglobulin-like repeats that show the highest similarity to neural cell adhesion molecule (N-CAM). Domain V has three globular repeats very similar to the domain G repeats in the laminin A chain and the equivalent segment of the A chain homologue, merosin, and two epidermal growth factor-like regions (Noonan and Hassell, *Kidney Int.* 43:53–60, 1993). The perlecan core protein is therefore a unique and large macromolecule with homology to a number of other well known proteins.

Normal Perlecan Production by Different Cell Types

Perlecan is normally present on all basement membranes (Dziadek et al, *EMBO J.* 4, 905–912, 1985; Kato et al, *J. Cell Biol.* 106:2203–2210, 1988; Murdoch et al, *J. Histochem. Cytochem.* 42: 239–249, 1994) and is known to be produced by different cell types including endothelial cells (Kinsella and Wight, *Biochem.* 27:2136–2144, 1988; Saku and Furthmayr, *J. Biol. Chem.* 264:3514–3523, 1989; Rescan et al, *Am. J. Path.* 142:199–208, 1993), smooth muscle cells (Nikkari et al, *Am. J. Path. 144: 1348–1356, 1994*), fibroblasts (Murdoch et al, *J. Histochem. Cytochem.* 42:239–249, 1994; Heremans et al, *J. Cell Biol.* 109:3199–3211, 1989), epithelial cells (Morris et al, *In Vitro Cell Dev. Biol.* 30:120–128, 1994; Ohji, et al, *Invest. Opth. Vis. Sci.* 35:479–485, 1994; Van Det et al, *Biochem. J.* 307:759–768, 1995), and synovial cells (Dodge et al, *Lab. Invest.* 73:649–657, 1995). Perlecan is also synthesized by bone marrow derived cells (Grassel et al, *Mol. Cell Biochem.* 145:61–68, 1995) and is present in cancerous tissue including metastatic melanomas (Cohen et al, *Cancer Res.* 54:5771–5774, 1994), human breast tumors (Guelstein et al, *Int. J. Cancer* 53:269–277, 1993), and liver tumors (Kovalsky et al, *Acta Biomed. Ateneo Parmense* 64:157–163, 1993). Both F9 embryonal carcinoma cells (which form parietal endoderm) and P19 embryonal carcinoma cells (which form cholinergic neurons) also demonstrate marked increased perlecan expression and synthesis upon differentiation (Chakravarti et al, *Dev. Dyn.* 197:107–114, 1993; Sekiguchi et al, *J. Neurosc. Res.* 38:670–686, 1994).

Discovery of Perlecan Domain I Splice Variants

Perlecan is also a specific heparan sulfate PG (previously referred to as a basement membrane heparan sulfate PG) that is a common constituent of all amyloid deposits regardless of the specific amyloid protein involved. Perlecan is believed to play primary roles in the pathogenesis of amyloidosis in general and contributes to the formation, deposition, accumulation and/or persistence of amyloid in a variety of tissues and different clinical settings. However, whether perlecan or closely related macromolecules present in the characteristic lesions (i.e. amyloid deposits and neurofibrillary tangles) and/or tissues of Alzheimer's disease and other amyloid disorders are altered, abnormal and/or different than normal is not known. Using RT-PCR technology and cloning methodology the present invention has identified unique splice variants of perlecan domain I which are present in total RNA derived from Alzheimer's disease or aged brain, and which are present in other human Alzheimer's disease tissues (kidney, liver, spleen, heart and pancreas) outside the central nervous system. The first perlecan domain I variant identified was the result of deletion of exon 5 and is referred to as Perlecan Domain I variant exon 5 (PerDI-v5). The splicing out of exon 5 results in a new open reading frame containing a stop codon in exon 7 which encodes for a predicted protein of 169 amino acids, with a molecular mass of ~17–18 kilodaltons. New sequence consisting of 72 amino acids occurs at the beginning of exon 6 and through part of exon 7. Within this new 72 amino acid sequence is a Ser-Gly-Asp (SGD) sequence suggestive of a new GAG attachment site. Therefore, this first perlecan splice variant consists of a ~17–18 kilodalton perlecan core protein potentially containing 4 GAG attachment sites. A peptide containing 17 amino acids of the unique sequence which resulted from the deletion of exon 5 was utilized to produce polyclonal anti-peptide antibodies (referred to as the "exon 5 deletion" antibody). Immunostaining of Alzheimer's disease brain sections with this unique antibody demonstrated the immunolocalization of the perlecan domain I variant exon 5 specifically to neurofibrillary tangles, one of the major pathological hallmarks of Alzheimer's disease.The second perlecan domain I variant identified was the result of deletion of exons 4, 5 and part of 6 and is referred to as Perlecan Domain I variant exon 4–6.5 (PerDI–v4–6.5). This deletion produces a stop codon which results in a predicted protein of 82 amino acids, with a molecular mass of ~8–9 kilodaltons. The third perlecan domain I variant identified was the result of the addition of new sequence (ie. exon 4a) near the beginning of exon 4 and is referred to as Perlecan Domain I variant exon 4a (PerDI+v4a). This new sequence codes for 11 amino acids (33 base pairs), has no known homology to any other protein, and includes the presence of a new Ser-Gly pair which may serve as a potential GAG attachment site. The fourth perlecan domain I variant identified was the result of the addition of new sequence (ie. exon 3a) following exon 3 and is referred to as Perlecan Domain I variant exon 3a (PerlDI+v3a). This sequence codes for 26 new amino acids (75 base pairs), has no known homology to any other protein, and includes the presence of a new Ser-Gly site which may serve as a potential GAG attachment site. A peptide containing 19 amino acids of the unique sequence, parts of which contain both perlecan domain I variant exon 4a and perlecan domain I variant exon 3a sequence, was utilized to produce polyclonal anti-peptide antibodies (referred to as the "perlecan domain I insert" antibody). Immunostaining of Alzheimer's disease brain sections with this unique "perlecan domain I insert" antibody demonstrated the immunolocalization of the perlecan domain I variant exon 3a and/or perlecan domain I variant exon 4a specifically to non-tangle bearing neurons, and amyloid plaques (another major pathological hallmark of Alzheimer's disease). Since perlecan is an invariable component of all amyloid deposits regardless of the specific amyloid protein involved, and plays postulated roles in the formation, deposition, accumulation and/or persistence of amyloid, these newly identified perlecan splice variants are deemed to play similar, if not more important roles in the pathogenesis of the amyloidoses. This invention therefore identifies unique perlecan domain I splice variants and provides for the production and utilization of specific perlecan domain I variant peptides, nucleotides, antibodies, and molecular biology probes for the diagnosis and therapeutic intervention of Alzheimer's disease and other amyloid disorders. In addition new animal models to effectively screen potential therapeutic compounds for each of the amyloidoses are disclosed.

Examples

The following examples are put forth so as to provide those with ordinary skill in the art with the disclosure and description of four perlecan domain I splice variants of the invention. However, it should not be construed that the invention is limited to these specific examples.

Example 1

Cloning of Perlecan Domain I Splice Variants

Total RNA was isolated from 10 human adult non-demented (control) and 10 Alzheimer's disease hippocampus samples obtained at autopsy from the University of Washington Alzheimer's Disease Research Center Brain Bank and immediately frozen at −70° C. as previously described (Nochlin et al, *Acta Neuropath.* 86:645–650, 1993). As shown in Table 1 (see FIG. 13), the mean age (+/− standard error of the mean) of the Alzheimer's disease cases was 86.4+/−3.1 years, with a range of 69–101 years, whereas the mean age of the non-Alzheimer's cases was 77.0+/−1.8 years, with a range of 67–86 years. The mean post-mortem delay was 5.1+/−0.6 hours for the AD cases and 6.7+/−0.9 hours for non-Alzheimer's cases and no significant difference was found between the two groups (p=0.17). The average duration of disease for the AD cases was 11.3+/−1.4 years.

Total cellular RNA was extracted by the acid guanidinium thiocyanate/phenol/chloroform method described by Chomzynski and Sacchi (*Anal. Biochem.* 162:156–159, 1987) or using a kit from Biotech, (Houston TX). RNA isolation from human brain tissue was modified for the high lipid content of brain samples by including an additional phenol/chloroform/isoamyl alcohol extraction. RNA concentration was determined by measuring the absorbance at 260 nm and 280 nm of serial dilutions of each sample. Accuracy of RNA quantification was confirmed using slot blot analysis. Briefly, decreasing amounts of RNA (2 $\mu$g to 0.5 $\mu$g), as determined by spectrophotometry (at 260 and 280 nm), were applied to a nylon membrane (Boehringer Mannheim) using a Bio-Dot SF microfiltration apparatus (Bio-Rad) according to the manufacturer's instructions. Membranes were then UV-crosslinked and hybridized with a digoxigenin-labelled human glyceraldehyde-3-phosphate dehydrogenase (GAPD) standard probe (obtained from American Type Culture Collection) as described for Southern blot analysis below. Using this ubiquitous transcript as a probe, it was determined that the spectrophotometric quantitation of RNA amounts was accurate.

Single-stranded cDNA was synthesized using 2000U of RNase H-negative Reverse Transcriptase (Superscript II, Gibco-BRL/Life Technologies, Grand Island, N.Y., USA) and random priming with 1.5 ug hexameric primers (Gibco-BRL). A pool of normal aged and Alzheimer's disease (AD) RNA was produced by mixing 5 $\mu$g of each patient RNA in a single tube labelled control or AD. The 100 $\mu$l reaction contained 5 $\mu$g of pooled control or AD RNA, 500 $\mu$M of each deoxynucleotide triphosphate (dNTP; Boehringer Mannheim), 200U ribonuclease inhibitor (rRNasin, Promega), 10M dithiothreitol, in 50 mM Tris-HCl (pH 8.3), 75 mM KCl and 3 mM $MgCl_2$. The RNA and random primers were first heat denatured at 70° C. for 10 min., reverse transcribed for 1.5 hours at 42° C. and enzyme-inactivated at 95° C. for 10 min. They were then stored at −20° C. until further use.

Primer sequences were based on the published sequences of human perlecan (Kallunki and Tryggvason, *J. Cell. Biol.* 116:559–571, 1992; Genbank accession number X62515; Murdoch et al, *J. Biol. Chem.* 267:8544–8557, 1992; Genbank accession number M85289). For example, the sequence of primer FPerlDIE and the sequence of primer RPerlDIX are shown in Table 2 (see FIG. 14). All primers were obtained from Operon Technologies.

The single-stranded cDNA (ssDNA) was amplified by polymerase chain reaction (PCR) in a programmable thermocycler (DNA Thermal Cycler; Perkin Elmer Cetus, Foster City, CA, USA) using 5–15 $\mu$l of the ssDNA in a 100 $\mu$l reaction mix containing 2.5U of a high fidelity polymerase mixture (Expand High Fidelity PCR System, Boehringer Mannheim) and 50 pmoles of each sense and antisense primer, FPerlDIE and RPerlDIX (see Table 2 for the sequences of all primers used). The samples were overlaid with mineral oil, heat-denatured at 94° for 3 min. followed by 72° for 3 min., 51° for 2 min., amplified (35 cycles of denaturation at 94° for 45 sec., primer annealing at 51° for 1.5 min., and DNA extension at 72° for 45 sec.) and incubated for a final 5 min. at 72° to complete extension. Samples were then stored at 4° C. until further use.

PCR products were purified by extraction with phenol and digested with EcoRI and XhoI (Boehringer Mannheim). The digested cDNA's were electrophoresed on a preparative low melt 4% agarose gel and the regions above and below the major 500 bp perlecan domain I band were cut out and purified using GENECLEAN (Bio 101, Inc). These cDNA's were ligated into the EcoRi and XhoI sites of pBluescript II SK (Stratagene) and used to transform competent XL-1 blue *E. coli* according to the manufacturer (Epicurian Coli, Stratagene) and plated on L agar plates containing carbenicillin, coated with X-gal and IPTG. Individual carbenicillin-resistant positive white colonies were grown in 2 ml of L broth overnight and the plasmids were isolated using the Qiagen Miniprep kit and digested with EcoRI and XhoI to analyze the inserted cDNAs. After electrophoresis on 2% Nu-Sieve agarose gels (FMC Bioproducts, Rockville, ME, USA), plasmids containing cDNA inserts were transferred to nylon membrane by the well known method of Southern, and UV-crosslinked. Hybridization probes were generated from the perlecan plasmids pBS-19J (corresponding to Domains I and II) and pBS-366 (corresponding to an internal region of Domain I)(Maresh et al., *J. Neurochem.* 67:1132–1144, 1996) by cutting the plasmids with EcoRI and XhoI, purifying the perlecan inserts and labelling them with digoxigenin-11-dUTP using the random primer method according to the manufacturer (Genius System User's Guide to Filter Hybridization, Boehringer Mannheim). The probes (Dig-19J or Dig-366) were hybridized with the blots at 42° overnight followed by two 5 min. washes in 2×saline-sodium citrate (SSC) containing 0.1% sodium dodecyl sulfate, and two 15 min. washes in 0.5×SSC, containing 0.1% sodium dodecyl sulfate at 65°. The hybridized probes were detected with an anti-digoxigenin antibody conjugated to alkaline phosphatase (anti-digoxigenin-AP, Boehringer Mannheim) according to the manufacturer, and visualized with Lumi-Phos 530, a chemiluminescent substrate (Boehringer Mannheim). Positive clones (those which hybridized with the perlecan probes) were sequenced using primers to the T3 and T7 regions found on the pBluescript plasmid and utilizing an Applied BioSystems 373A Automated Sequencer and the Applied BioSystems Prism*Dye Terminator kit, or by Genomis, Inc.(Duluth, Ga.) on a PE Applied Biosystems 377 DNA Sequencer. The clones reported in this invention were each sequenced twice.

Example 2

Figure 2:
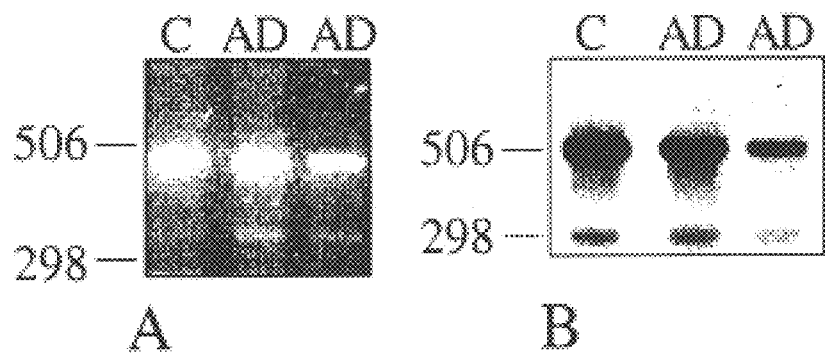
FIG. 2 is an example of RT-PCR performed on total RNA isolated from the hippocampus of one normal aged and two Alzheimer's disease patients using primers specific (FPerDI and RPerlDI) for perlecan domain I.

Identification of Higher and Lower Molecular Weight Perlecan Domain I Bands: Possibility of Potential Alternatively Spliced Transcripts Analysis of total RNA derived from hippocampi of patients with Alzheimer's disease or normal aged control (see Table 1; FIG. 13) suggested the possibility of alternatively spliced transcripts of perlecan domain I. FIG. 2A shows an ethidium bromide stained agarose gel of the RT-PCR products performed on total RNA derived from the hippocampus of one normal aged control (C) and two Alzheimer's disease (AD) patients, using primers specific (FPerDI and RPerlDI) for perlecan domain I (see Table 2; FIG. 14; and FIG. 4A). The prominent 503 base pair band apparent in control and AD lanes, which is the expected size of perlecan domain I, was accompanied by smaller and larger fainter bands (FIG. 2A) which were not eliminated by changing the conditions of PCR. Southern blot analysis (FIG. 2B) using a perlecan Domain I specific probe (Dig-366) demonstrated the expected 503 base pair band of perlecan. In addition, at least two smaller bands (one just below the 503 band of perlecan domain I, and the other just below the 298 base pair standard marker) were also recognized by the perlecan probe suggesting the possible presence of perlecan transcripts of unexpected sizes in both Alzheimer's disease and control hippocampus. Upon further analysis of total RNA from the hippocampi of more normal aged control and Alzheimer's disease patients using identical techniques (as described above), larger bands were sometimes observed above the expected 503 base pair band (not shown). It is important to note that the full-length mRNAs represented by these perlecan-related bands would most likely not be differentiated on Northern analysis since human perlecan MRNA is ~14 kilobases, and it would not be discerned from a potential transcript differing in only a few hundred nucleotides in size.

Example 3

Cloning and Sequencing of Perlecan Domain I Splice Variants

Figure 3:
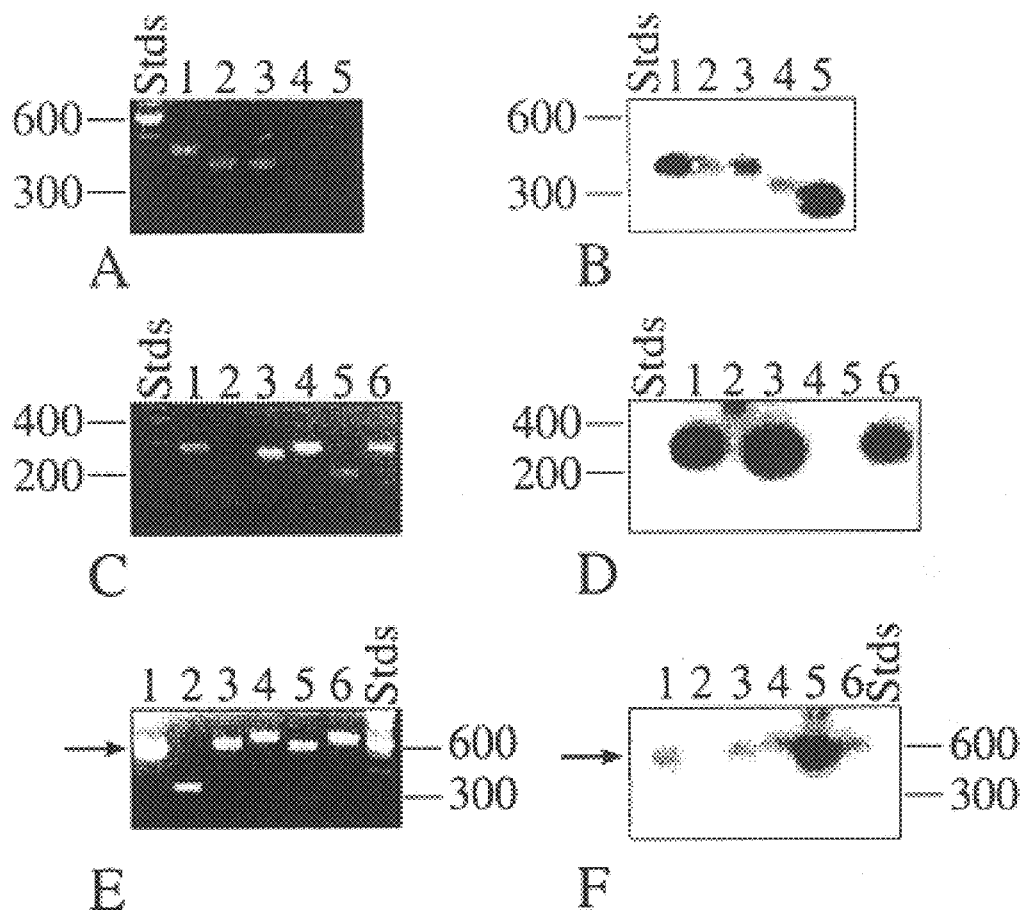
FIG. 3 are the clones produced by RT-PCR of pooled total RNA from either control or Alzheimer's disease hippocampi using high fidelity polymerase and primers FPerlDIE and RPerlDIX. RT-PCR products were separated on a low melt agarose gel and regions above and below the 503 base pair perlecan band were cut out and cloned into the EcoRI and XhoI sites of pBluescript.

Since the perlecan-related RT-PCR products may have been derived from either perlecan mRNA splice variants or genes with high homology to perlecan domain I, experiments were initiated and designed to identify these transcripts through cloning and sequencing. Primers were designed (Table 2; FIG. 14) for amplification and cloning as follows: the forward primer (FPerlDIE) was specific for a region near the 5' end of human perlecan domain I (Genbank accession number M85289) and contained an EcoRI restriction site, whereas the reverse primer (RPerlDIX) was specific for a region near the 3' end of human perlecan domain I and contained an XhoI restriction site. RT-PCR (using a high fidelity polymerase) was performed on pooled hippocampus samples from 10 Alzheimer's disease or 10 normal aged control patients (see Table 1; FIG. 13), and cDNA products which were smaller or larger than approximately 500 base pairs were cloned into the EcoRi and XhoI sites of pBluescript. FIG. 3 demonstrates examples of plasmid clones which had inserts smaller or larger than the 500 base pair perlecan domain I (arrow in FIG. 3E and 3F demonstrates normal perlecan at 503 base pairs in lanes 1 of each figure) upon digestion by EcoRI and XhoI (ethidium bromide stained gels, FIGS. 3A, C and E). All plasmids containing inserts were analyzed by Southern blot using one of two probes; Dig-19J which hybridizes to perlecan domains I and II (FIG. 3D), or Dig-366 which hybridizes to the central portion of perlecan domain I (FIGS. 3B and F). Out of 61 clones from the Alzheimer's disease pooled hippocampus RNA samples, 18 clones were found to hybridize with the perlecan domain I or perlecan domain I and II specific probes. Out of 48 clones from the normal aged control pooled hippocampus RNA samples, 18 clones were also found to hybridize with the perlecan domain I or perlecan domain I and II specific probes. Sequencing of some of the plasmids shown in FIG. 3 demonstrated the existence of four different perlecan domain I splice variants as described below. For example, the band shown in FIGS. 3A and B, lane 4 was found to contain a perlecan domain I splice variant in which exon 5 had been removed (discussed below). The bands shown in FIGS. 3C and D, lanes 1 and 6 were found to contain a perlecan domain I splice variant in which exons 4, 5 and part of 6 were removed (discussed below). Lastly, the bands shown in FIGS. 3E and F, lanes 4 and 6 were found to contain additional inserts of different sizes, following exon 3 and at the beginning of exon 4 (discussed below).

Example 4

Identification of a Perlecan Domain I Splice Variant Missing Exon 5

Figure 4A:
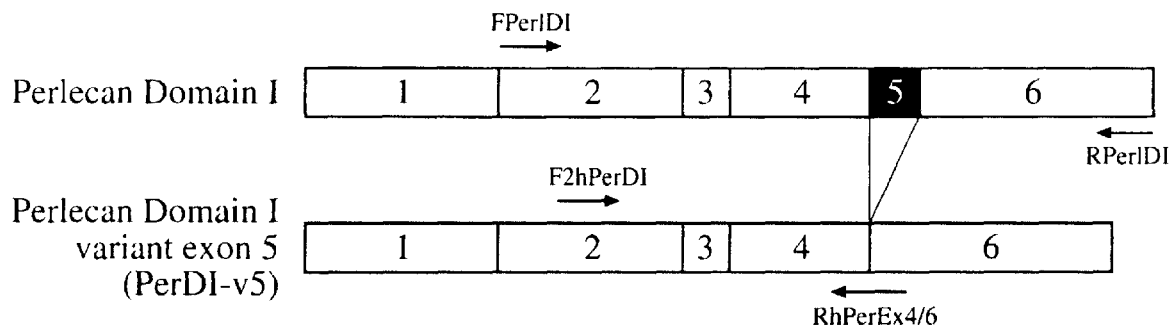
FIG. 4A compares the exon structure of the newly identified human perlecan domain I splice variant which has exon 5 deleted (referred to as Perlecan Domain I variant exon 5), to that of normal human perlecan domain I. The PCR primers used for amplification are indicated.

One of the clones that was sequenced from an Alzheimer's disease pooled hippocampal cDNA was found to consist of a perlecan domain I splice variant that was missing exon 5. This variant was designated as PerDI-v5 (Perlecan Domain I variant exon 5) to describe that exon 5 is deleted from perlecan domain I. FIG. 4A depicts the exon structure of this variant in comparison to that of normal human perlecan domain I (which contains 5 exons). In FIG. 4B, the nucleic acid sequence of this clone (SEQ ID NO: 1 and SEQ ID NO:2) is compared to that of normal human perlecan (using the nucleotide numbering system in Genbank accession number M85289). The first difference is a T to G change at nucleotide 252 resulting in a non-conservative amino acid change of tyrosine (amino acid number 58) to aspartic acid (FIG. 4C; SEQ ID NO: 3). The 59 base pair exon 5 (Cohen et al, *Proc. Natl. Acad. Sci. U.S.A.* 90:10404–10408, 1993) was found to be precisely deleted at the known splice sites. The complete amino acid sequence of this predicted perlecan domain I variant is shown in FIG. 4C (SEQ ID NO: 3). The sequence between the two black diamonds shown in FIG. 4C is the sequence of the cDNA clone that we obtained. The rest of the perlecan sequence is predicted from normal human perlecan. The deletion of exon 5 resulted in a change of the reading frame starting at exon 6. The new amino acid sequence (SEQ ID NO: 4) predicts a stop codon at nucleotide 651 which would result in a protein of 190 amino acids (169 amino acids without the signal peptide sequence). The new amino acid sequence of splice variant PerDI-v5contains a Ser-Gly-Asp (SGD) sequence at amino acid numbers 142–144, identical to the three SGD sequences present between amino acids 65–78 (FIG. 4C; SEQ ID NO: 3). The SGD sequences are consensus sequences for the addition of glycosaminoglycan chains (on each Serine residue) and therefore the predicted 169 amino acid protein (molecular mass of ~17–18 kilodaltons) would be a small proteoglycan with up to 4 GAG chains attached. Search for homologies of the new amino acid sequence (SEQ ID NO: 4) in Perlecan Domain I variant exon 5 in current genomic and protein databases demonstrated no matches with amino acid identity >30%. This indicated that the new amino acid sequence (SEQ ID NO: 4) in Perlecan Domain I variant exon 5 was unique.

Example 5

Identification of a Perlecan Domain I Splice Variants Missing Exons 4, 5 and Part of 6

Figure 5A:
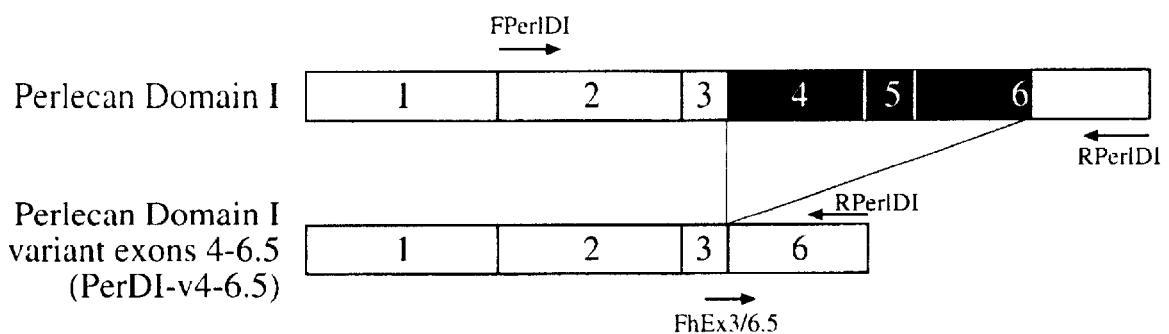
FIG. 5A compares the exon structure of the newly identified human perlecan domain I splice variant which has exons 4–6.5 deleted (referred to as Perlecan Domain I variant exons 4–6.5), to that of normal human perlecan domain I. The PCR primers used for amplification are indicated.

Three of the clones that were sequenced from the Alzheimer's disease pooled hippocampal cDNA were found to consist of a perlecan domain I splice variant that was missing exons 4, 5 and part of 6. This variant was designated as PerDI–v4–6.5 (Perlecan Domain I variant exons 4–6.5) to describe that exons 4, 5 and approximately half of 6, are deleted from perlecan domain I. FIG. 5A depicts the exon structure of this variant in comparison to that of normal human perlecan domain I. In FIG. 5B, the nucleic acid sequence of this clone (SEQ ID NO: 6) is compared to that of normal human perlecan (using the nucleotide numbering system in Genbank accession number M85289), and demonstrates that 236 base pairs have been removed. The sequences of normal perlecan in this region of exon 6 do not adhere to the GT/AG rule of consensus splice sites (Jacob and Gallinaro, *Nucleic Acid Res.* 17:2159–2180, 1989) although several examples of non-consensus MRNA splice sites are known (Jackson, *Nucleic Acid Res.* 19:3795–3798, 1991). The deletion results in a change of reading frame which immediately codes for a stop codon (*) in the amino acid sequence (* in FIG. 5C)(SEQ ID NO: 7). This results in the predicted production of a very small (82 amino acids or with a molecular mass of ~8–9 kilodaltons) perlecan domain-I like protein containing 3 GAG attachment sites. There is also a change in amino acid 58 from a tyrosine to an aspartic acid because of a T to G change at nucleotide 252 (FIG. 5C; SEQ ID NO: 7).

Example 6

Identification of a Perlecan Domain I Splice Variant Containing Additional New Sequence (33 Nucleotides) in Exon 4

Figure 6A:
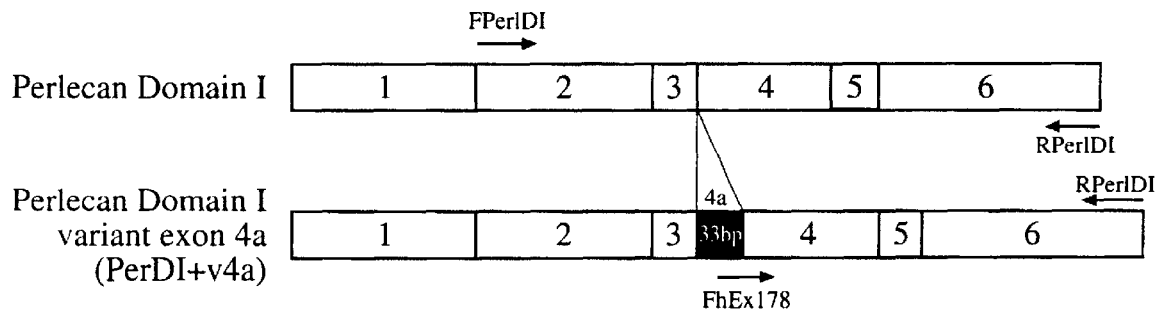
FIG. 6A compares the exon structure of the newly identified perlecan domain I splice variant which has 33 nucleotides inserted near the beginning of exon 4 (referred to as Perlecan Domain I variant exon 4a) to that of normal human perlecan domain I. The PCR primers used for amplification are indicated.

One clone that was sequenced from the normal aged pooled hippocampal cDNA was found to consist of a perlecan domain I splice variant in which 33 new nucleotides (SEQ ID NO: 9) were inserted near the beginning of exon 4. This variant was designated as PerDI+4a (Perlecan Domain I variant exon 4a) to describe that new sequence is present at the beginning of exon 4 (ie. new region referred to as exon 4a). FIG. 6A depicts the exon structure of this variant in comparison to that of normal human perlecan domain I. The insertion of new sequence occurred 14 bases following the start of exon 4 (FIG. 6B). This insertion leaves the reading frame unchanged and therefore this variant should code for the rest of normal perlecan, an approximately 14,000 base pair (bp) transcript with an open reading frame of 13,173 bp+33 bp=13,206 bp. The 33 inserted nucleotides code for 11 new amino acids (SEQ ID NO: 10), 5 of which are hydrophobic (FIG. 6C). A serine-glycine pair is also present in the new sequence which could also serve as a site for glycosaminoglycan chain attachment. There are also two nucleotide differences between this variant and normal perlecan at nucleotides 164 and 252 (FIGS. 6B, 6C). The A to C change at nucleotide 164 does not result in an amino acid (ie. alanine) change, however the T to G change at nucleotide 252 results in a non-conservative amino acid change of tyrosine to aspartic acid (FIG. 6C). Search for homologies of the new 11 amino acid sequence (SEQ ID NO: 10) in Perlecan Domain I variant exon 4a in current genomic and protein databases demonstrated no matches with amino acid identity >20%. This indicated that the new 11 amino acid sequence (SEQ ID NO: 10) in Perlecan Domain I variant exon 4a was unique.

Example 7

Identification of a Perlecan Domain I Splice Variant Containing Additional New Sequence (75 Nucleotides) Following Exon 3

Figure 7A:
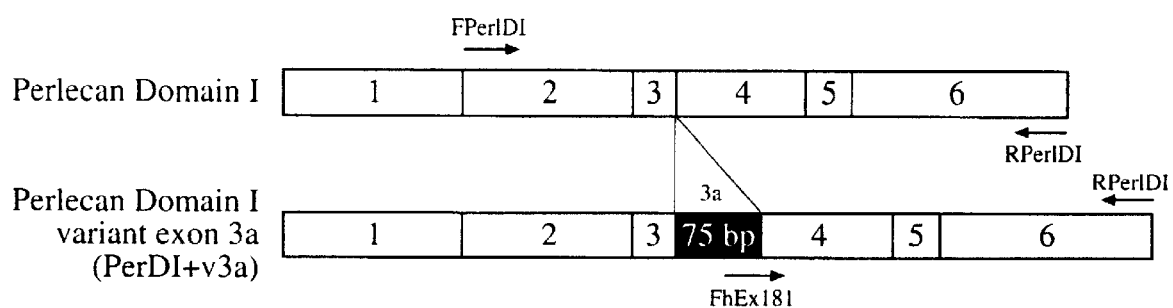
FIG. 7A compares the exon structure of the newly identified perlecan domain I splice variant which has 75 nucleotides inserted following exon 3 (ie. Perlecan Domain I variant exon 3a) to that of normal human perlecan domain I. The PCR primers used for amplification are indicated.

Two clones that were sequenced from the normal aged pooled hippocampal cDNA were found to consist of a perlecan domain I splice variant in which 75 new nucleotides (SEQ ID NO: 12) were inserted following exon 3. This variant was designated as PerDI+3a (Perlecan Domain I variant exon 3a) to describe that new sequence is present following exon 3 (ie. new region referred to as exon 3a). FIG. 7A depicts the exon structure of this variant in comparison to that of normal human perlecan domain I. The insertion of new sequence occurred precisely between exons 3 and 4 (FIG. 7B). This insertion leaves the reading frame unchanged and therefore this variant should code for the rest of normal perlecan, an approximately 14,000 base pair (bp) transcript with an open reading frame of 13,173 bp+75 bp=13,248 bp. This perlecan domain I variant is very similar to the variant PerDI+4a in that a) the first 33 base pairs (and therefore the encoded 11 amino acids; SEQ ID NO: 10) of the 75 base pair insert are the same, and b) there is also a T to G change at nucleotide 252 which results in a non-conservative change of tyrosine to aspartic acid (FIG. 7C). The new insertion codes for 26 amino acids (there is a valine to a glycine change right at the splice site), 13 of which are hydrophobic (FIG. 7C; SEQ ID NO: 13). In addition, the new sequence also contains a Serine-Glycine sequence indicative of a potential glycosaminoglycan attachment site. Search for homologies of the new 26 amino acid sequence (SEQ ID NO: 13) in Perlecan Domain I variant exon 3a in current genomic and protein databases demonstrated no matches with amino acid identity >20%. This indicated that the new 26 amino acid sequence (SEQ ID NO: 13) in Perlecan Domain I variant exon 4a was unique (with the exception noted above).

Example 8

Figure 8:
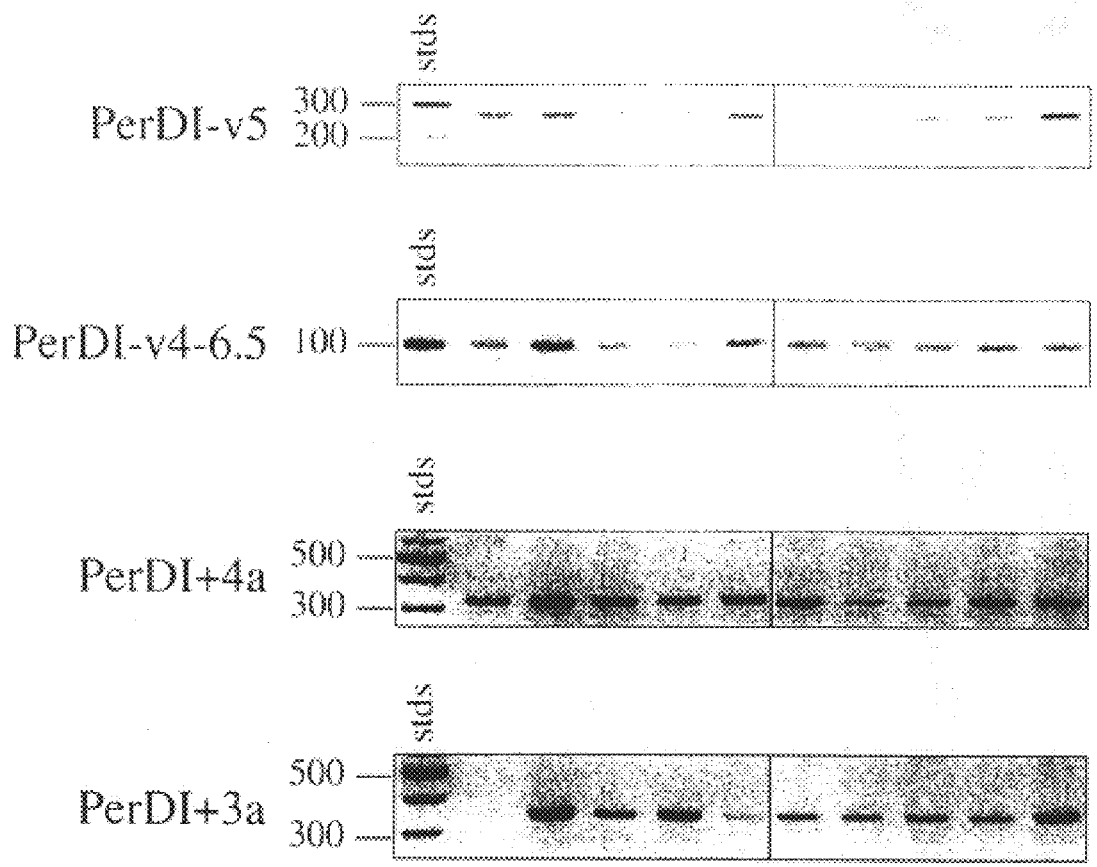
FIG. 8 demonstrates the expression of perlecan domain I splice variants in Alzheimer's disease hippocampi. RT-PCR was performed on total RNA derived from the hippocampi of 10 Alzheimer's disease patients. The primer pairs used, expected size of products and conditions for PCR were: F2hPerDI and RhPerEx4/6, 260 base pairs (56n° annealing, 35 cycles) for perlecan domain I variant exon 5; FhEx3/6.5 and RPerlDI, 92 base pairs (60° annealing, 35 cycles) for perlecan domain I variant exons 4–6.5; FhEx178 and RPerlDI, 325 base pairs (60° annealing, 35 cycles) for perlecan domain I variant exon 4a; FhEx181 and RPerDI, 339 base pairs (60° annealing, 35 cycles) for perlecan domain I variant exon 3a. The PCR products were analyzed on 2% or 4% agarose gels stained with ethidium bromide. The 100 base pair ladder of standards are indicated as stds. This figure demonstrates the presence of four perlecan domain I splice variants in most of the Alzheimer's disease hippocampi analyzed.

Presence of Four Perlecan Domain I Splice Transcripts in RNA Obtained from the Hippocampi of Different Individuals with Alzheimer's Disease Whether these four splice variants described in the invention existed in RNA obtained from the hippocampi of patients with Alzheimer's disease was then determined. For these studies, specific primers across the new exon junctions were designed (see Table 2-FIG. 14; FIGS. 4A, 5A, 6A and 7A; and SEQ ID NO: 5, SEQ ID NO: 8, SEQ ID NO: 11; SEQ ID NO: 14 and SEQ ID NOS: 17–20) and used RT-PCR reaction conditions which minimized the binding of primers to normal human perlecan sequence. Optimization of the PCR parameters to obtain maximum specificity included changing the annealing temperature and the number of amplification cycles. The primer pairs used, expected size of products and conditions for PCR were: F2hPerDI and RhPerEx4/6 (SEQ ID NO: 5 and SEQ ID NO: 17), 260 base pairs (56° annealing, 35 cycles) for perlecan domain I variant exon 5; FhEx3/6.5 and RPerlDI (SEQ ID NO: 8 and SEQ ID NO: 18), 92 base pairs (60° annealing, 35 cycles) for perlecan domain I variant exons 4–6.5; FhEx178 and RPerlDI (SEQ ID NO: 11 and SEQ ID NO: 19), 325 base pairs (60° annealing, 35 cycles) for perlecan domain I variant exon 4a; FhEx181 and RPerDI (SEQ ID NO: 14 and SEQ ID NO: 20), 339 base pairs (60° annealing, 35 cycles) for perlecan domain I variant exon 3a. Controls included performing the reverse transcriptase reaction without enzyme (to check for subsequent amplification of genomic DNA in the RNA preparations) and performing the PCR without template to check for DNA contamination in the reagents. Both controls described above were consistently negative. As shown in FIG. 8, RT-PCR was performed on total RNA isolated from hippocampi of 10 Alzheimer's disease patients (see Table 1-FIG. 13) using the specific perlecan domain I splice variant primer pairs. The results indicated (FIG. 8) that a) the perlecan domain I exon 5 splice variant was present in 10 of 10 AD patients; b) the perlecan domain I exons 4–6.5 splice variant was present in 10 of 10 AD patients; c) the perlecan domain I exon+4a insertion variant was present in 10 of 10 AD patients; and d) the perlecan domain I exon+3a insertion variant was present in 9 of 10 AD patients. These results indicate that all four splice variants are present in RNA derived from the hippocampi of nearly all patients with Alzheimer's disease.

Example 9

Production of Polyclonal Antibodies Against Unique Amino Acid Sequence in Perlecan Domain I Variant Exon 5

In contract with Zymed Laboratories (South San Francisco, U.S.A.), the unique amino acid sequence of Perlecan Domain I variant exon 5 (SEQ ID NO: 4) was analyzed to determine which specific region would be useful for custom peptide synthesis and the generation of polyclonal anti-peptide antibodies. Computer algorithms to determine the immunogenicity of different peptide regions included the Kyte and Doolittle model of hydrophilicity, and determinations of peptide regions for indices of flexibility, protein surface probability, amphiphilicity, and favorable secondary structure were used. The overall rating based on the first 5 categories gave an antigenic index for each specific peptide region considered. A segment of 17 amino acids corresponding to P-T-P-G-H-S-A-P-V-P-K-S-L-H-G-G-R (SEQ ID NO: 15) was picked for antibody production due primarily to favorable secondary structure. Peptide synthesis, purification and site-directed KLH conjugation, and accelerated antibody service using the PolyQuik™ method was performed by Zymed Laboratories (South San Francisco, U.S.A.). For site-directed KLH conjugation the following peptide was synthesized and immunized in rabbits for polyclonal anti-peptide production: (C)-P-T-P-G-H-S-A-P-V-P-K-S-L-H-G-G-R-COOH SEQ ID NO: 15. The cysteine residue (C) was assigned for single point, site-directed KLH conjugation use.

Two rabbits were immunized with the above peptide for polyclonal antibody production. Rabbit pre-immune serum, and serum obtained following peptide immunization, were then tested by ELISA, utilizing the specific peptide sequence described above. The ELISA data indicated very good, peptide-specific antibody titers (not shown).

Example 10

Immunolocalization of the Perlecan Domain I Variant Exon 5 to the Neurofibrillary Tangles of Alzheimer's Disease Polyclonal anti-peptide antibodies against the 17 amino acid peptide (SEQ ID NO: 15) unique sequence region present in perlecan domain I variant exon 5 (known as the "exon 5 deletion" antibody) were then used to immunolocalize this perlecan variant in the brains of patients with Alzheimer's disease. Brain tissue sections which included hippocampus or frontal cortex from 5 cases of confirmed Alzheimer's disease were obtained from the University of Washington Alzheimer's Disease Research Center and utilized. From each block of paraffin-embedded material, 6–8 $\mu$M serial sections were cut and placed on gelatin coated slides. Amyloid-containing plaques and neurofibrillary tangles were identified following Congo red staining (Puchtler et al, *J. Histochem. Cytochem.* 10:355–364, 1962) when viewed under polarized light. Detection of the perlecan domain I variant exon 5 was achieved using the "exon 5 deletion" antibody described above used at a dilution of 1:300 and 1:500. Controls consisted of staining an adjacent serial section with the same "exon 5 deletion" antibody preabsorbed with excess 17-amino acid peptide (which was also provided to us by Zymed Laboratories), and/or staining an adjacent serial section with preimmune serum from the same rabbit utilized to make the "exon 5 deletion:" antibody. Immunostaining of tissue sections was accomplished using the avidin-biotin complex (Hsu et al, *J. Histochem. Cytochem.* 29:577–580, 1981) with a hematoxylin counterstain. For immunocytochemical staining the primary antibody was tested at different dilutions to obtain the best specificity with the least background staining. Only the optimal dilutions of primary antibody are reported. Tissue sections with the "exon 5 deletion" antibody were pretreated for 5 minutes with 88% formic acid before immunostaining to aid in unmasking hidden antigenic sites (Kitamoto et al, *Lab. Invest.* 57:230–236, 1987).

Congo red staining of hippocampus and frontal cortex from patients with confirmed Alzheimer's disease revealed numerous amyloid plaques (not shown) and neurofibrillary tangles (FIG. 10A, arrowheads) when stained with Congo red and viewed under polarized light. The "exon 5 deletion" antibody revealed intense staining of neurofibrillary tangles (FIGS. 10B, 10C and 10D), both ghost tangles and intraneuronal tangles which were identified by positive Congo red staining on adjacent serial sections. The "exon 5 deletion" antibody only immunostained neurofibrillary tangles, and not amyloid or neuritic plaques, in several different cases of Alzheimer's disease. In addition, this antibody rarely immunostained non-tangle bearing neurons. Preabsorption experiments utilizing the "exon 5 deletion" antibody in the presence of excess 17-amino acid peptide (which served as the antigen for antibody production), completely eliminated any positive immunostaining, indicating the specificity of the antibody used (not shown). In addition, sections from Alzheimer's disease cases immunostained with preimmune serum did not show any positive immunostaining of neurofibrillary tangles. Immunolocalization studies utilizing the polyclonal perlecan "exon 5 deletion" antibody surprisingly did not immunostain basement membranes or blood vessels in brain, suggesting that this perlecan variant may have a distinctly different distribution than perlecan or "normal basement membrane heparan sulfate PGs". This study therefore demonstrated that in Alzheimer's disease brain the perlecan domain I exon 5 deletion variant was localized specifically to the neurofibrillary tangles present in brain.

Example 11

Production of Polyclonal Antibodies Against Unique Amino Acid Sequence in Perlecan Domain I Variant Exon 3a and/or Perlecan Domain I Variant Exon 4a In contract with Zymed Laboratories (South San Francisco, U.S.A.), the unique amino acid sequence region predicted in Perlecan Domain I variant exon 4a (SEQ ID NO: 13) was also analyzed to determine which specific region would be useful for custom peptide synthesis and the generation of polyclonal anti-peptide antibodies. Computer algorithms to determine the immunogenicity of different peptide regions included the Kyte and Doolittle model of hydrophilicity, and determinations of peptide regions for indices of flexibility, protein surface probability, amphiphilicity, and favorable secondary structure were used The overall rating based on the first 5 categories gave an antigenic index for each specific peptide region considered. A segment of 19 amino acids corresponding to Q-P-L-G-R-P-P-V-A-G-M-M-V-S-E-P-D-E-E (SEQ ID NO: 17) was picked for antibody production due primarily to favorable overall index. Note that the peptide region picked for antibody production consisted of 8 amino acids (out of 11) present in the perlecan domain I variant exon 3a (SEQ ID NO: 10), and 11 amino acids that were unique to perlecan domain I variant exon 4a. It was therefore believed that peptide antibodies produced against this 19 amino acid region would detect sequence present in perlecan domain I variant exon 4a and/or perlecan domain I variant exon 3a. Peptide synthesis, purification and site-directed KLH conjugation, and accelerated antibody service using the PolyQuik™ method was performed by Zymed Laboratories (South San Francisco, U.S.A.). For site-directed KLH conjugation the following peptide was synthesized and immunized in rabbits for polyclonal anti-peptide production: (C)-Q-P-L-G-R-P-P-V-A-G-M-M-V-S-E-P-D-E-E-COOH. The cysteine residue (C) was assigned for single point, site-directed KLH conjugation use.

Two rabbits were immunized with the above peptide for polyclonal antibody production. Rabbit pre-immune serum ,and serum obtained following peptide immunization, were then tested by ELISA, utilizing the specific peptide sequence as described above. The ELISA data indicated very good, peptide-specific antibody titers (not shown).

Example 12

Immunolocalization of the Perlecan Domain I Variant Exon 3a and/or Perlecan Domain I Variant Exon 4a to the Amyloid Plaques of Alzheimer's Disease Polyclonal anti-peptide antibodies against the 19 amino acid peptide (SEQ ID NO: 16) sequence region present in perlecan domain I variant exon 3a and/or perlecan domain I variant exon 4a (known as the "perlecan domain I insert" antibody) were then used to localize these perlecan "insert" variants in the brains of patients with Alzheimer's disease. Brain tissue sections which included hippocampus or frontal cortex from 5 cases of confirmed Alzheimer's disease were obtained from the University of Washington Alzheimer's Disease Research Center and utilized. From each block of paraffin-embedded material, 6–8 $\mu$M serial sections were cut and placed on gelatin coated slides. Amyloid-containing plaques and neurofibrillary tangles were identified following Congo red staining (Puchtler et al, *J. Histochem. Cytochem.* 10:355–364, 1962) when viewed under polarized light. In addition, A$\beta$ containing deposits (present in amyloid plaques and cerebrovascular amyloid deposits) were detected using a monoclonal antibody which recognizes residues 17–24 of A$\beta$ (known as anti-4G8; Senetek). Detection of the perlecan domain I variant exon 4a and/or perlecan domain I variant exon 3a was achieved using the "perlecan domain I insert" antibody described above used at a dilution of 1:250 and 1:350. Controls consisted of staining an adjacent serial section with the same "perlecan domain I insert" antibody preabsorbed with excess 19-amino acid peptide (which was also provided to us by Zymed Laboratories), and/or staining an adjacent serial section with preimmune serum from the same rabbit utilized to make the "perlecan domain I insert" antibody. Immunostaining of tissue sections was accomplished using the avidin-biotin complex (Hsu et al, *J. Histochem. Cytochem.* 29:577–580, 1981) with a hematoxylin counterstain. For immunocytochemical staining the primary antibody was tested at different dilutions to obtain the best specificity with the least background staining. Only the optimal dilutions of primary antibody are reported. Tissue sections with the "perlecan domain I insert" antibody were pretreated for 5 minutes with 88% formic acid before immunostaining to aid in unmasking hidden antigenic sites (Kitamoto et al, *Lab. Invest.* 57:230–236, 1987).

Figure 12:
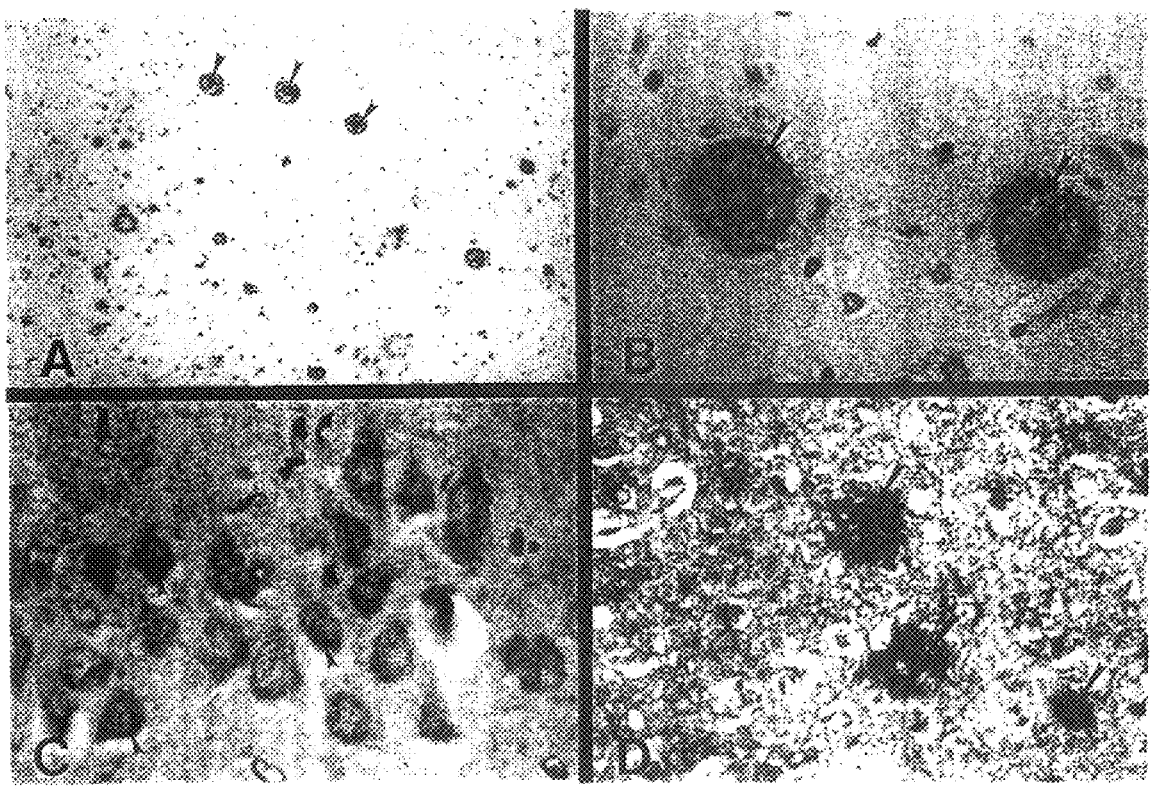
FIG. 12 are black and white photomicrographs demonstrating the immunolocalization of the Perlecan Domain I variant exon 4a and/or Perlecan Domain I variant exon 3a to neurons and amyloid plaques in Alzheimer's disease brain utilizing the "perlecan domain I insert" antibody.

Congo red staining of hippocampus and frontal cortex from patients with confirmed Alzheimer's disease revealed numerous amyloid plaques and neurofibrillary tangles when stained with Congo red and viewed under polarized light (not shown). A$\beta$-containing amyloid plaques were further identified and immunolocalized in Alzheimer's disease brain utilizing the anti-4G8 antibody (FIGS. 12A and 12B). The "perlecan domain I insert" antibody was immunolocalized to non-tangle bearing neurons (such as some of pyramidal neurons of the hippocampus)(FIG. 12C) in most cases of Alzheimer's disease. In addition, the "perlecan domain I insert" antibody immunostained amyloid-containing plaques (FIGS. 12D). Plaque immunostaining with the "perlecan domain I insert" antibody was found to be fixation sensitive and was generally surprisingly observed predominantly in tissues that had been fixed in formalin. The "perlecan domain I insert" antibody generally did not immunostain neurofibrillary tangles, but did immunostain blood vessel walls including medium size arterioles and small capillaries [reminiscent of normal perlecan (i.e. non-splice variant) immunostaining]. Preabsorption experiments utilizing the "perlecan domain I insert" antibody in the presence of excess 19-amino acid peptide (which served as the antigen for antibody production), completely eliminated all positive immunostaining described above, indicating the specificity of the antibody used (not shown). In addition, sections form Alzheimer's disease cases immunostained with preimmune serum did not show any positive immunostaining of neurons or amyloid plaques. This study therefore demonstrated that in Alzheimer's disease brain the perlecan domain I variant exon 3a, and/or perlecan domain I variant exon 4a, was localized specifically and primarily to neurons and amyloid plaques present in brain.

Example 13

Presence of Four Perlecan Domain I Splice Transcripts in RNA from Alzheimer's Disease Tissues Obtained Outside the Central Nervous System Human tissues including brain (hippocampus, cortex), spleen, liver, kidney, heart and/or pancreas were obtained from the autopsy service of the Dept. of Pathology, University of Washington. Brain and other tissues were derived from an 80 yr old male with confirmed Alzheimer's disease. Total RNA was isolated as described above (in example 1) and single-stranded cDNA was synthesized using 1 ug of RNA, 200U of RNase H-negative Reverse Transcriptase (Superscript II, Gibco-BRL) and 150 ng hexameric primers (Gibco-BRL) in the reaction buffer provided for 1.5 hr at 42°. Amplification was performed as described above (in example 1) except that a) Taq polymerase (Boehringer Mannheim) was used, b) primer annealing was performed at the temperatures dictated by the primer pair used, and c) the annealing time was 1 min and cycle number varied from 30–35. Optimization of the PCR parameters to obtain maximum specificity of junction spanning primers included changing the annealing temperature and the number of amplification cycles. The primer pairs used, expected size of products and conditions for PCR were: F2hPerDI and RhPerEx4/6, 260 base pairs (56° annealing, 35 cycles) for perlecan domain I variant exon 5; FhEx3/6.5 and RPerlDI, 92 base pairs (60° annealing, 35 cycles) for perlecan domain I variant exons 4–6.5; FhEx178 and RPerlDI, 325 base pairs (60° annealing, 35 cycles) for perlecan domain I variant exon 4a; FhEx 181 and RPerDI, 339 base pairs (60° annealing, 35 cycles) for perlecan domain I variants exon 3a. Controls included performing the reverse transcriptase reaction without enzyme (to check for subsequent amplification of genomic DNA in the RNA preparations) and performing the PCR without template to check for DNA contamination in the reagents. Both control scenarios described above were consistently negative. RT-PCR products were analyzed on 2% or 4% agarose gels stained with ethidium bromide.

The specific perlecan domain I primers (described in example 8) were used to determine whether these splice variants existed in RNA obtained from other tissues outside of the central nervous system. Normal perlecan domain I expression was detected in several tissues from the same Alzheimer's disease patient including brain (cortex), pancreas, liver, spleen and kidney (Table 3). Initial analysis utilizing the specific perlecan domain I variant primers and RT-PCR methodology (as described herein) also suggested that all four perlecan splice variants were present in most other organs (which lie outside the central nervous system) analyzed. For example, the perlecan domain I exon 5 variant (designated v5 in Table 3) was detected by RT-PCR analysis in the pancreas, liver, heart, spleen, brain and kidney. Similarly, the perlecan domain I exon 4–6.5 variant was detected in the pancreas, liver, heart, spleen, brain and kidney of the same Alzheimer's disease patient. These results indicated that the four perlecan splice variants identified in this invention were not only present in brain, but were also likely present in several tissues lying outside the central nervous system. The presence of these perlecan domain I splice variants in a variety of tissues outside the central nervous system strengthens the concept that these variants are most likely important for each of the amyloidoses which demonstrate amyloid deposition in brain (ie. Aβ amyloid, PrP amyloid) or in specific organs outside the central nervous system (ie. AA amyloid, AL amyloid, beta$_2$-microglobulin amyloid , islet amyloid, endocrine type amyloidosis, transthyretin/prealbumin amyloid). Even though these perlecan domain I splice variants may be present in brain and in systemic organs, differences in quantitative levels of these variants will also serve as a important basis for diagnostic and therapeutic applications as described herein.

TABLE 3

Perlecan Domain I Splice Variant RNA Expression in Human Tissues

| Alzheimer's patient Tissues | Perlecan | v5 | v4–6.5 | v4a | v3a |
|---|---|---|---|---|---|
| Brain | ++* | ++ | ++ | ++ | ++ |
| Pancreas | ++ | + | ++ | ++ | ++ |
| Liver | ++ | ++ | ++ | + | ++ |
| Heart | +++ | ++ | ++ | + | ++ |
| Spleen | ++ | ++ | ++ | ++ | + |
| Kidney | ++ | ++ | +++ | ++ | ++ |

*Relative abundance is depicted as: +, ++, or +++

FURTHER ASPECTS, UTILIZATIONS AND PREFERRED EMBODIMENTS OF THE INVENTION

Nucleic Acids

In accordance with one aspect of the present invention there are provided isolated nucleic acid molecules, including mRNAs, DNAs, cDNAs, as well as analogs and biologically active and diagnostically or therapeutically useful fragments thereof.

In accordance with another aspect of the present invention there are provided isolated nucleic acids (polynucleotides) which encode for the mature polypeptides having the deduced amino acid sequences of FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16).

The polynucleotides of the present invention may be in the form of RNA or in the form of DNA, which DNA includes cDNA, genomic DNA, and synthetic DNA. The DNA may be double-stranded or single-stranded, and if single-stranded may be the coding strand or non-coding (anti-sense) strand. The coding sequence which encodes the mature polypeptide may be identical to the coding sequence shown in FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), FIG. 11 (SEQ ID NO: 16) or may be a different nucleotide sequence as a result of the redundancy or degeneracy of the genetic code, encodes the same mature polypeptide as the DNA of FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), FIG. 11 (SEQ ID NO: 16) or the cDNA.

The polynucleotide which encodes for the mature polypeptides of FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16) or for the mature polypeptides encoded by the deposited cDNA may include, but is not limited to: only the coding sequence for the mature polypeptides, the coding sequences for the mature polypeptides and additional coding sequences such as a leader or secretory sequence or proprotein sequence, the coding sequences for the mature polypeptides (and optionally additional coding sequences) and non-coding sequences, such as introns or non-coding sequences 5' and/or 3' of the coding sequences for the mature polypeptides. Therefore, the term "polynucleotide encoding a polypeptide" encompasses a polynucleotide which includes only coding sequence for the polypeptide as well as a polynucleotide which includes additional coding and/or non-coding sequence.

The present invention includes polynucleotides encoding the same mature polypeptides as shown in FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16) or the same mature polypeptides encoded by the cDNAs of the deposited clones as well as variants of such polynucleotides which variants encode for a fragment, derivative or analog of the polypeptides of FIG. 4C (SEQ ID NO: 4), Figure 5C (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16) or the polypeptides encoded by the cDNAs of the deposited clones. Such nucleotide variants include deletion variants, substitution variants and additional or insertion variants.

As hereinabove indicated, the polynucleotides may have a coding sequence which is a naturally occurring allelic variant of the coding sequences shown in FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16) or the coding sequences of the deposited clones. As known in the art, an allelic variant is an alternate form of a polynucleotide sequence which may have a substitution, deletion or addition of one or more nucleotides, which does not substantially alter the function of the encoded polypeptides.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional N-terminal amino acid residues. A mature protein having a prosequence is a proprotein and is an inactive form of the protein. Once the prosequence is cleaved an active mature protein remains. Thus, for example the polynucleotides of the present invention may encode for a mature protein, or for a protein having a prosequence or for a protein having both a prosequence and a presequence (leader sequence).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 4C (SEQ ID NO: 4), FIG. 5C (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16) or the deposited cDNAs.

The present invention further relates to variants of the hereinabove described polynucleotides which encode for fragments, analogs and derivatives of the polypeptide having the deduced amino acid sequence of FIG. 4C (SEQ ID NO: 4), FIG. 5C (SEQ ID NO: 7), FIG. 6C (SEQ ID NO: 10 ), FIG. 7C (SEQ ID NO: 13), FIG. 9 (SEQ ID NO: 15), and FIG. 11 (SEQ ID NO: 16) or the polypeptides encoded by the cDNA of the deposited clones. The variant of the polynucleotide may be a naturally occurring allelic variant of the polynucleotide or a naturally occurring variant of the polynucleotide.

In yet another aspect of the invention, the perlecan domain I variant plasmids as described herein can be used for Northern blot analysis of mRNA derived from human tissues, cells, and/or cells in biological fluids to further determine the size of transcripts. In addition, Northern blots utilizing the same probes of the invention can be utilized to quantitate relative levels of perlecan domain I splice variant mRNA in tissues from normal patients in comparison to those with specific diseases (such as the amyloid diseases).

In yet another aspect of the invention, fragments of the full length gene may be used as a hybridization probe for a cDNA library to isolate the full length gene and to isolate other genes which have a high sequence similarity to the gene or similar biological activity. Probes of this type have at least 19 bases and may contain, for example, 50 or more bases. The probe may also be used to identify a cDNA clone corresponding to a full length transcript and a genomic clone or clones that contain the complete perlecan domain I splice variant gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Another aspect of the invention relates to vectors which includes polynucleotides as described herein, host cells which are genetically engineered with vectors of the invention and the production of polypeptides of the invention by recombinant techniques. Host cells are genetically engineered (transformed or transduced or transfected) with the vectors of the invention which may be, for example, a cloning vector or an expression vector. The vector may be, for example, in the form of a plasmid, a viral particle, a phage etc. The engineered host cells can be cultured in conventional nutrient media modified as appropriate for activating promoters, selecting transformants or amplifying the genes. The culture conditions, such as temperature, pH and the like, are those previously utilized with the host cell selected for expression, and will be apparent to those ordinarily skilled in the art.

In another aspect of the invention, the polynucleotides of the present invention may be employed for producing polypeptides by recombinant techniques. For example, the polynucleotides may be included in any one of a variety of expression vectors for expressing a polypeptide. Such vectors included chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The present invention accordingly encompasses the expression of a perlecan domain I splice variant polypeptide, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cells or tissue is of human, primate, hamster, rabbit, rodent, cow, pig, sheep, horse, goat, dog, or cat origin, but any other mammalian cell may be used.

The polynucleotides of the present invention may be utilized as research reagents and materials for discovery of treatments and diagnostics to human diseases.

Peptides, Amino Acids and GAGs

The polypeptides referred to in the present invention may be a natural polypeptide, a synthetic polypeptide or a recombinant polypeptide. The fragments, derivatives or analogs of the polypeptides to any of the perlecan domain I splice variants referred to herein may be a) one in which one or more of the amino acid residues are substituted with a conserved or non-conserved amino acid residue and such substituted amino acid residue may or may not be encoded by the genetic code, or b) one in which one or more of the amino acid residues includes a substituent group, or c) one in which the mature polypeptide is fused with another compound, such as a compound used to increase the half-life of the polypeptide (for example, polyethylene glycol), or d) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of the invention.

The polypeptides of the present invention include the polypeptides or fragments therein contained within the deduced amino acid sequences of each perlecan domain I splice variant as shown in FIG. 4C (SEQ ID NO: 4), FIG. SC (SEQ ID NO: 7), FIG. 6C (SEQ ID NO: 10), FIG. 7C (SEQ ID NO: 13), FIG. 9 (SEQ ID NO: 15), and FIG. 11 (SEQ ID NO: 16) as well as polypeptides which have at least 70% similarity (preferably 70% identity) and more preferably a 90% similarity (more preferably a 90% identity) to the polypeptides described above.

Fragments or portions of the polypeptides of the present invention may be employed for producing the corresponding full-length polypeptides by peptide synthesis; therefore, the fragments may be employed as intermediates for producing the full length polypeptides. Fragments of portions of the polynucleotides of the present invention may be used to synthesize full-length polynucleotides of the present invention.

In accordance with one aspect of the present invention there is provided novel new peptide sequences within the new perlecan domain I splice variants described herein, as well as biologically active and diagnostically or therapeutically useful fragments, analogs and derivatives thereof. The peptide sequences described in the present invention are human sequences.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant procedure, the polypeptides of the present invention may be glycosylated or may be non-glycosylated. Polypeptides of the invention may also include an initial methionine amino acid residue.

Perlecan domain I polypeptides of the present invention of can be synthesized according to known method steps, including portions of disclosed new perlecan domain I polypeptides, conservative substitution derivatives thereof or functional derivatives thereof.

Chemical polypeptide synthesis is a rapidly evolving area in the art, and methods of solid phase polypeptide synthesis are well-described in the following references, hereby entirely incorporated by reference (Merrifield, *J. Amer. Chem. Soc.* 85:2149–2154, 1963; Merrifield, *Science* 232:341–347, 1986; Fields, *Int. J. Polypeptide Prot. Res.* 35, 161, 1990).

Recombinant production of perlecan domain I polypeptide can be accomplished according to known method steps. Standard reference works seting forth the general principles of recombinant DNA technology include Watson, *Molecular Biology of the Gene*, Volumes I and II, The Benjamin/Cummings Publishing Company Inc., publisher, Menlo Park, Calif. 1987; Ausubel et al, eds., *Current Protocols in Molecular Biology*, Wiley Interscience, publisher, New York, N.Y. 1987; 1992; and Sambrook et al, *Molecular Cloning: A Laboratory Manual*, Second Edition, Cold Spring Harbor Laboratory, publisher, Cold Spring Harbor, N.Y. 1989, the entire contents of which references are herein incorporated by reference.

The polypeptides of the present invention may be utilized as research reagents and materials for discovery of treatments and diagnostics for human diseases.

Perlecan domain I splice variant antibodies can also be used to isolate the perlecan domain I splice variant proteins from tissues using procedures known to those in the art. Examples include, but are not limited to, the use of affinity column chromatography and immunoprecipitation methodology. Isolation of perlecan domain I splice variants from tissues will allow one to also further strucutrally characterize the GAG chains associated with said perlecan domain I splice variants. Such GAG chains can be isolated and characterized according to class of GAG, length and size of GAG chain, and specific monosaccharide, disaccharide and polysaccharide structures. Such analysis can be obtained using methods known to those in the art including those described in Hampson and Gallagher, *Biochem. J.* 221:697–705, 1984; Farach-Carson et al, *Biotech* 7:482–493, 1989; Gyo and Conrad, *Anal. Biochem.* 176:96–104, 1989; DaCol et al, *J. Chromatography* 647:289–300, 1993; Hovingh et al, *Eur. J. Biochem.* 211:771–779, 1993; which are entirely incorporated herein by reference, included all references cited therein.

Antibodies

Antibodies generated against the polypeptides corresponding to specific sequences recognizing the perlecan domain I splice variants of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptides from tissue expressing that polypeptide. Preferred embodiments include, but are not limited to, the anti-peptide antibodies described herein such as the "perlecan exon 5 deletion" antibody and the "perlecan domain I insert" antibody, which are utilized to detect for the presence and location of perlecan domain I exon 5 variant, and perlecan domain I variant exon 4a and/or perlecan domain I variant exon 3a, respectively. Preferred peptides utilized to make these antibodies include, but are not limited to, the peptide sequences described of SEQ ID NO: 15 and SEQ ID NO: 16. For the generation of anti-peptide antibodies using these described sequences, a preferred embodiment includes the addition of a cysteine residue at the amino terminal end of SEQ ID NO: 15 and/or SEQ ID NO: 16 for single point, site directed KLH conjugation use.

The term "antibody" is meant to include polyclonal antibodies, monoclonal antibodies, chimeric antibodies, anti-idiotypic antibodies to antibodies specific for a perlecan domain I splice variant polypeptide of the present invention, as well as fragments thereof.

Polyclonal antibodies are heterogeneous populations of antibody molecules derived from the sera of animals immunized with an antigen.

A monoclonal antibody contains a substantially homogeneous population of antibodies specific to antigens, which population contains substantially similar epitope binding sites. For preparation of monoclonal antibodies, any technique which provides antibodies produced by continuous cell line cultures can be used. Examples include the hybridoma technique (Kohler and Milstein, *Nature* 256:495–497, 1975), the trioma technique, the human B-cell hybridoma technique (Kozbor et al, *Immunology Today* 4:72, 1983), and the EBV-hybridoma technique to produce human monoclonal antibodies (Cole et al, in *Monoclonal Antibodies and Cancer Therapy*, Alan R. Liss, Inc., pp. 77–96, 1985). Such antibodies may be of any immunoglobulin class including IgG, IgM, IgE, IgA, GILD and any subclass thereof.

Chimeric antibodies are molecules different portions of which are derived from different animal species, such as those having variable region derived from a murine monoclonal antibody and a human immunoglobulin constant region, which are primarily used to reduce immunogenicity in application and to increase yields in production. Chimeric antibodies and methods for their production are known in the art (ex. Cabilly et al, *Proc. Natl. Acad. Sci. U.S.A* 81:3273–3277, 1984; Harlow and Lane: *Antibodies: A Laboratory Manual*, Cold Spring Harbor Laboratory 1988).

An anti-idiotypic antibody is an antibody which recognizes unique determinants generally associated with the antigen-binding site of an antibody. An anti-iodiotypic antibody can be prepared by immunizing an animal of the same species and genetic type (e.g., mouse strain) as the source of the monoclonal antibody with the monoclonal antibody to which an anti-iodiotypic antibody is being prepared. The immunized animal will recognize and respond to the idiotypic determinants of the immunizing antibody by producing an antibody to these idiotypic determinants (the anti-idiotypic antibody). See, for example, U.S. Pat. No. 4,699,880, which is herein incorporated by reference.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al, *J. Nucl. Med.* 24:316–325, 1983).

The antibodies or fragments of antibodies, useful in the present invention may be used to quantitatively or qualitatively detect a perlecan domain I splice variant in a sample or to detect presence of cells which express a perlecan domain I variant polypeptide of the present invention. This can be accomplished by immunofluorescence techniques employing a fluorescently labeled antibody coupled with light microscopic, flow cytometric or fluorometric detection.

One of the ways in which a perlecan domain I variant antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric, or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colometric methods which employ a chromogenic substrate for the enzyme. Detection can be accomplished by colorimetric methods which employ a chromogenic substrate for the enzyme. Detection can also be accomplished by visual comparison of the extent of enzymatic reaction of a substrate with similarly prepared standards (see Harlow and Lane, *Antibodies: A Laboratory Manual*, Cold Spring Harbor Laboratory 1988; Ausubel et al, eds., *Current Protocols in Molecular Biology*, Wiley Interscience, N.Y. 1987, 1992).

Detection may be accomplished using any of a variety of other immunoassays. For example, by radiolabeling of the antibodies or antibody fragments, it is possible to detect R-PTPase through the use of a radioimmunoassay (RIA). A good description of RIA may be found in *Laboratory Techniques and Biochemistry in Molecular Biology*, by Work et al, North Holland Publishing Company, NY (1978) with particular reference to the chapter entitled "An Introduction to Radioimmune Assay and Related Techniques" by Chard, incorporated entirely by reference herein. The radioactive isotope can be detected by such means as the use of a gamma-counter, a scintillation counter or by autoradiography.

It is also possible to label an anti-perlecan domain I splice variant polypeptide antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg., U.S.A.).

The antibody can also be detectably labeled using fluorescence emitting metals such as 152EU, or other of the lanthanide series. These metals can be attached to the antibody using such metal groups as diethylenetriamine pentacetic acid (EDTA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Like wise, a bioluminescent compound may be used to label the antibody of the present invention. Bioluminescence is a type of chemiluminescence found in biological systems in which a catalytic protei n increases the efficiency of the chemiluminescent reaction. The presence of a bioluminescent protein is determined by detecting the presence of luminescence. Important bioluminescent compound s for purposes of labeling are luciferin, luciferase and aequorin.

The antibodies (or fragments thereof) useful in the present invention may be employed histologically, as in immunofluorescence or immunoelectron microscopy, for in situ detection of a perlecan domain I splice variant of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of a perlecan domain I variant polypeptide but also its distribution on the examined tissue. Using the present invention, those of ordinary skill will readily perceive that any of a wide variety of histological methods (such as staining procedures) can be modified in order to achieve such in situ detection.

In accordance with yet a further aspect of the present invention there are provided antibodies against each of the perlecan domain I splice variant peptides or fragments thereof. These antibodies can be used for a number of important diagnostic and/or therapeutic applications as described herein. In one aspect of the invention, polyclonal and/or monoclonal antibodies made against each perlecan domain I splice variant (such as the "perlecan exon 5 deletion" antibody described in example 9 and the "perlecan domain I insert" antibody described in example 11) may be utilized for Western blot analysis (using standard Western blotting techniques knowledgeable to those skilled in the art) to detect the presence of each perlecan domain I splice variant protein in human tissues and in tissues of other species. Western blot analysis can also be used to determine the apparent size of each full length perlecan domain I splice variant. In addition, Western blotting following by scanning densitometry (knowledgeable to those skilled in the art) can be used to quantitate and compare levels of each of the perlecan domain I splice variants in tissue samples or biopsies obtained from individuals with specific diseases (such as the amyloid diseases) in comparison to tissue samples or biopsies obtained from normal individuals or controls.

In yet another aspect of the invention, polyclonal and/or monoclonal antibodies made against the perlecan domain I splice variants can be utilized for immunoprecipitation studies (using standard immunoprecipitation techniques knowledgeable to one skilled in the art) to detect each of the perlecan domain I splice variant proteins in tissues, cells and/or biological fluids. Use of the perlecan domain I splice variant antibodies for immunoprecipitation studies can also be quantitative to determine relative levels of a particular splice variant in tissues, cells and/or biological fluids. Quantitative immunoprecipitation can be used to compare levels of each of the perlecan domain I splice variants in tissue samples or biopsies obtained from individuals with specific diseases (such as the amyloid diseases) in comparison to tissue samples or biopsies obtained from normal individuals or controls.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Diagnostic Applications
Use of Primers and/or Nucleic Acids

The invention provides in one aspect methods of diagnosis of amyloidosis, which method comprises analyzing the expression of the perlecan domain I variant gene in a sample. In a particular embodiment, the invention provides methods of assaying a sample for products of the perlecan gene or part thereof which method comprises, making cDNA from messenger RNA (MRNA) in the sample, amplifying portions of the complementary DNA (cDNA) corresponding to the perlecan gene or part thereof and detecting the amplified cDNA, characterized in that the amplified cDNA is used in the diagnosis and prognosis of the amyloidoses.The amyloid diseases include, but are not limited to, the amyloid associated with Alzheimer's disease and Down's syndrome (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the arnyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin). The sample on which the assay is preformed is preferably of body tissue or body fluid. The sample may be a piece of tissue obtained by biopsy, or a fine needle aspirate of cells. Alternatively, it may be a sample of blood or urine or another body fluid, such as a cervical scraping or a non-invasively obtained sample such as sputum, urine or stool.

The primers described in FIG. 14-Table 2 can be utilized for the specific detection of perlecan domain I splice variants in RNA derived from tissues, cells, and/or cells in biological fluids. In one preferred embodiment, the primer referred to as RhPEREx4/6 as described in Table 2 and SEQ ID NO: 5 is a primer that spans across the exon 4–6 junction of perlecan domain I (FIG. 4A) and can be used in conjunction with primer F2hPerDI (Table 2)(SEQ ID NO: 5) to detect perlecan domain I variant exon 5 in human tissues using standard RT-PCR methodology, knowledgeable to one skilled in the art. In another preferred embodiment, the primer referred to as FhEx3/6.5 as described in Table 2 and SEQ ID NO: 8 is a primer that spans across the exon 3–6.5 junction of perlecan domain I (FIG. 5A) and can be used in conjunction with primer RPerDI (FIG. 14-Table 2)(SEQ ID NO: 8) to detect perlecan domain I variant exons 4–6.5 in human tissues using standard RT-PCR methodology, knowledgeable to one skilled in the art. In yet another preferred embodiment, the primer referred to as FhEx178 as described in Table 2 and SEQ ID NO: 11 is a primer that spans exons 4a–4 (exon 4a is an additional exon identified in this invention) of perlecan domain I (FIG. 7A) and can be used in conjunction with primer RPerDI (Table 2)(SEQ ID NO: 11) to detect perlecan domain I variant exon 4a in human tissues using standard RT-PCR methodology, knowledgeable to one skilled in the art. In yet another preferred embodiment, the primer referred to as FhEx181 as described in Table 2 and SEQ ID NO: 14 is a primer that spans exons 3a–4 (exon 3a is an additional exon identified in this invention) of perlecan domain I (FIG. 8A) and can be used in conjunction with primer RPerDI (FIG. 14-Table 2; SEQ ID NO: 11) to detect perlecan domain I variant exon 3a in human tissues using standard RT-PCR methodology, knowledgeable to one skilled in the art. Such use of primers described in the present invention can be used in a kit comprising of primer pairs (as described above) for the detection of each perlecan domain I splice variant in RNA.

In addition, the primers can be used for quantitative competitive RT-PCR (Maresh et al, *J. Neurochem.* 67:1132–1144, 1996) to determine the quantitative differences in these specific perlecan domain I variants in total RNA derived from human tissues, cells, white blood cells and/or cells in biological fluids. Changes in quantitative levels of these perlecan domain I splice variants will aid in the diagnosis and prognosis of patients who demonstrate amyloid and concurrent perlecan domain I splice variant accumulation in tissues as part of the pathological process in the amyloid diseases. In a preferred embodiment, specific primers are utilized (as described above) for quantitative RT-PCR to determine levels of specific perlecan domain I splice variants in patients with an amyloid disease in comparison to age-matched controls. The specific perlecan domain I splice variants which are determined to be significantly elevated or diminished in tissues, cells and/or cells in biological fluids in a type of amyloidosis will aid in the diagnosis and monitoring of the prognosis of a given patient afflicted with a particular amyloid disease. Elevated or diminished levels of a particular perlecan domain I splice variant will be indicative of perlecan domain I splice variant deposition, accumulation and/or persistence which will correlate with amyloid deposition, accumulation and/or persistence in a given patient. Increasing elevations of a particular perlecan domain I splice variant in a biopsy or biological fluid sample obtained from a patient at regular intervals (ie. every 6 months) may suggest continued deposition and accumulation of this perlecan domain I splice variant in conjunction with amyloid, implicating a worsening of the disease. Such diagnostic assays as described above may be produced in a kit form.

This invention is also related to the use of the perlecan domain I splice variant gene as a diagnostic. Detection of a mutated form of perlecan domain I splice variants will allow a diagnosis of a disease or a susceptibility to a disease which results from overexpression or underexpression of perlecan domain I splice variants. Individuals carrying mutations in the human perlecan domain I splice variant gene may be detected at the DNA level by a variety of techniques. Nucleic acids for diagnosis may be obtained from a patient's cells, from blood, urine, saliva, tissue biopsy, stool and autopsy material. The genomic DNA may be used directly for detection or may be amplified enzymatically by using PCR prior to analysis. RNA or cDNA may also be used for the same purpose. As an example, PCR primers (as described herein; FIG. 14-Table 2) complementary to the nucleic acids encoding the perlecan domain I splice variants can be used to identify and analyze mutations. For example, deletions and insertions can be detected by a change in size of the amplified product in comparison to the normal genotype. Point mutations can be identified by hybridizing amplified DNA to radiolabeled perlecan domain I splice variant RNA or alternatively, radiolabeled perlecan domain I splice variant antisense DNA sequences. Perfectly matched sequences can be distinguished from mismatched duplexes by RNase A digestion or by differences in melting temperatures.

Sequencing differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags. Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (Myers et al, *Science* 230:1242, 1985). Sequence changes at specific locations may also be revealed by nuclease protection assays, such as RNase and S1 protection or the chemical cleavage method (e.g., Cotton et al, *Proc. Natl. Acad. Sci. U.S.A*, 85:4397–4401, 1985). Therefore, the detection of a specific DNA sequence may be achieved by methods such as hybridization, RNase protection, chemical cleavage, direct DNA sequencing or the use of restriction enzymes (e.g., Restriction Fragment Length Polymorphisms (RFLP)) and Southern blotting of genomic DNA. In addition to more conventional gel-electrophoresis and DNA sequencing, mutations can also be detected by in situ analysis.

Yet another aspect of the invention is to make oligonucleotides utilizing the nucleotide sequences described herein, to be utilized as new molecular biological probes to detect perlecan domain I splice variants in human tissues by standard in situ hybridization techniques, knowledgeable by one skilled in the art. In a preferred embodiment, this includes the utilization of the nucleic acid sequenes described in SEQ ID NO: 1, SEQ ID NO: 2, SEQ ID NO: 6, SEQ ID NO: 9, and/or SEQ ID NO: 12.

Use of Peptides and/or Antibodies

Another aspect of the invention is to provide polyclonal and/or monoclonal peptide antibodies which would be utilized to specifically detect each of the perlecan domain I splice variants in human tissues and/or biological fluids. In a preferred embodiment, polyclonal or monoclonal antibodies made against a peptide portion or fragment of the perlecan domain I splice variant exon 5 (SEQ ID NO: 3) and/or the unique 72 amino acid peptide (shown in FIG. 4C and SEQ ID NO: 4) contained within perlecan domain I variant exon 5, can be used to detect and quantify perlecan domain I variant exon 5 in human tissues and/or biological fluids. In a preferred embodiment, a polyclonal antibody made against the amino acid sequence of SEQ ID NO: 15 (ie. referred herein as to the "perlecan exon 5 deletion" antibody) can be utilized to detect perlecan domain I variant exon 5 in tissues, and/or biological fluids, and would have both diagnostic and therapeutic applications (described herein). Polyclonal and/or monoclonal peptide antibodies can also be utilized to specifically detect the perlecan domain I splice variant exons 4–6.5 in human tissues and/or biological fluids. In a preferred embodiment, a polyclonal or monoclonal antibody made specifically against a peptide portion or fragment of the amino acid sequence region of perlecan domain I variant 4–6.5 (SEQ ID NO: 6) and/or a portion thereof that, can be used to detect and quantify perlecan domain I variant exons 4–6.5 in human tissues and/or biological fluids. Polyclonal and/or monoclonal peptide antibodies can also be utilized to specifically detect the perlecan domain I splice variant exon 4a in human tissues and/or biological fluids. In a preferred embodiment, a polyclonal or monoclonal antibody made specifically against a peptide portion or fragment of the unique 11 amino acid sequence region (shown in FIG. 6C and SEQ ID NO: 10) contained within perlecan domain I variant exon 4a can be used to detect and quantify perlecan domain I variant exon 4a in human tissues and/or biological fluids. Polyclonal and/or monoclonal peptide antibodies can also be utilized to specifically detect the perlecan domain I splice variant exon 3a in human tissues and/or biological fluids. In a preferred embodiment, a polyclonal or monoclonal antibody made specifically against a peptide portion or fragment of the new 26 amino acid sequence (shown in FIG. 7C and SEQ ID NO: 13) contained within perlecan domain I variant exon 3a can be used to detect and quantify perlecan domain I variant exon 3a in human tissues and/or biological fluids. In another preferred embodiment, a polyclonal antibody made against the amino acid sequence of SEQ ID NO: 16 which can detect perlecan domain I exon variant 4a and/or perlecan domain I exon variant 3a, is utilized to detect these perlecan domain I "insert" variants in tissues and/or biological fluids.

For detection of the perlecan domain I splice variants described above in human tissues, cells, and/or in cell culture, the polyclonal and/or monoclonal antibodies can be utilized using standard immunohistochemical and immunocytochemical techniques, knowledgeable to one skilled in the art.

For detection and quantitation of specific perlecan domain I splice variants in biological fluids, including cerebrospinal fluid, blood, plasma, serum, urine, sputum, and/or stool, various types of ELISA assays can be utilized, knowledgeable to one skilled in the art. An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier, and a quantity of detectable labeled soluble antibody is added to permit detection and/or quantitation of the ternary complex formed between solid-phase antibody, antigen, and labeled antibody.

In a preferred embodiment, a "sandwich" type of ELISA can be used. Using this preferred method a pilot study is first implemented to determine the quantity of binding of each perlecan domain I splice variant monoclonal antibody to microtiter wells. Once this is determined, aliquots (usually in 40 $\mu$l of TBS; pH 7.4) of the specific perlecan domain I splice variant antibody are allowed to bind overnight to microtiter wells (Maxisorb C plate from Nunc) at 4° C. A series of blank wells not containing any primary perlecan domain I splice variant specific monoclonal antibody are also utilized as controls. The next day, non-bound monoclonal antibody is shaken off the microtiter wells. All of the microtiter wells (including the blank wells) are then blocked by incubating for 2 hours with 300 $\mu$l of Tris-buffered saline containing 0.05% Tween-20 (TTBS) plus 2% bovine serum albumin, followed by 5 rinses with TTBS. 200 $\mu$l of cerebrospinal fluid, blood, plasma, serum, urine, sputum, and/or stool and/or any other type of biological sample is then diluted (to be determined empirically) in TTBS containing 2% bovine serum albumin and placed in wells (in triplicate) containing bound perlecan domain I splice variant antibody (or blank) and incubated for 2 hours at room temperature. The wells are then washed 5 times with TTBS. A second biotinylated-monoclonal antibody against the same perlecan domain I splice variant (but which is against a different epitope) is then added to each well (usually in 40 $\mu$l of TBS; pH 7.4) and allowed to bind for 2 hours at room temperature to any perlecan domain I splice variant protein captured by the first antibody. Following incubation, the wells are washed 5 times with TTBS. Bound materials are then detected by incubating with 100 $\mu$l of peroxidase-avidin complex (1:250 dilution in TTBS with 0.1% BSA) for 1 hour on a rotary shaker. After 5 washes with TTBS, a substrate solution (100 $\mu$l, OPD-Sigma Fast from Sigma Chemical Co., St. Louis, Mo., USA) is added and allowed to develop significant color (usually 8–10 minutes). The reaction is stopped with 50 $\mu$l of 4N sulfuric acid and read on a standard spectrophotometer at 490 nm. This ELISA can be utilized to determine differences in specific perlecan domain I splice variants in biological fluids which can serve as a diagnostic marker to follow the progression on a live patient during the progression of disease (ie. monitoring of amyloid disease as an example). In addition, quantitative changes in perlecan domain I splice variants can also serve as a prognostic indicator monitoring how a live patient will respond to treatment which targets a given amyloid disease. Such diagnostic assays can be provided in a kit form.

A competition assay may also be employed wherein antibodies specific to a perlecan domain I splice variant are attached to a solid support and labelled perlecan domain I splice variant protein and a sample derived from a host are passed over the solid support and the amount of label detected attached to the solid support can be correlated to the quantity of the perlecan domain I splice variant in the sample. This standard technique is knowledgeable to one skilled in the art.

Another object of the present invention is to use the perlecan domain I splice variant peptides or fragments thereof, in conjunction with perlecan domain I variant specific antibodies, in an ELISA assay to detect potential perlecan domain I splice variant autoantibodies in human biological fluids. Such a diagnostic assay may be produced in a kit form. In a preferred embodiment, peptides containing the new sequences of the perlecan domain I splice variants as shown in FIG. 4C (SEQ ID NO: 4), FIG. 6C (SEQ ID NO: 10), FIG. 7C (SEQ ID NO: 13), FIG. 9 (SEQ ID NO: 15), FIG. 11 (SEQ ID NO: 16) or containing the amino acid sequence spanning the new exon 3 to exon 6.5 junction as shown in FIG. 5C (SEQ ID NO: 7) will be used to initially bind to microtiter wells in an ELISA plate. A pilot study is first implemented to determine the quantity of binding of each perlecan domain I splice variant peptide to microtiter wells. Once this is determined, aliquots (usually 1–2 $\mu$g in 40 $\mu$l of TBS; pH 7.4) of specific perlecan domain I splice variant peptides (as described herein) are allowed to bind overnight to microtiter wells (Maxisorb C plate from Nunc) at 4° C. All the microtiter wells (including blank wells without the perlecan domain I splice variant) are blocked by incubating for 2 hours with 300 $\mu$l of Tris-buffered saline (pH 7.4) with 0.05% Tween-20 (TTBS), containing 2% albumin. This is followed by 5 rinses with TTBS. The patients biological fluids (i.e., cerebrospinal fluid, blood, plasma, serum, sputum, urine, and/or stool) are then utilized and 200 $\mu$l are diluted (to be determined empirically) with TTBS containing 2% bovine serum albumin, and placed in microtiter wells (in triplicate) containing a specific perlecan domain I variant peptide or blank wells (which do not contain peptide), and are incubated at 1.5 hours at room temperature. Any autoantibodies present in the biological fluids against the specific perlecan domain I splice variant will bind to the substrate bound perlecan domain I variant peptide (or fragments thereof). The wells are then rinsed by washing 5 times with TTBS. 100 $\mu$l of biotinylated polyclonal goat anti-human IgGs (Sigma Chemical company, St. Louis, Mo., USA), diluted 1:500 in TTBS with 0.1% bovine serum albumin, is then aliquoted into each well. Bound materials are detected by incubating with 100 $\mu$l of peroxidase-avidin complex (1:250 dilution in TTBS with 0.1% bovine serum albumin) for 1 hour on a rotary shaker. Following 5 washes with TTBS, substrate solution (100 $\mu$l, OPD-Sigma Fast from Sigma Chemical Company, St. Louis, Mo., USA) is added and allowed to develop significant color (usually 8–10 minutes). The reaction is stopped with 50 $\mu$l of 4N sulfuric acid added to each well and read on a standard spectrophotometer at 490 nm. This assay system can be utilized to not only detect the presence of autoantibodies against perlecan domain I splice variants in biological fluids, but also to monitor the progression of disease by following elevation or diminution of perlecan domain I splice variant autoantibody levels. It is believed that patients demonstrating excessive perlecan domain I splice variant formation, deposition, accumulation and/or persistence as observed in the amyloid diseases, will also carry autoantibodies against one or many of the perlecan splice variants in their biological fluids. Various ELISA assay systems, knowledgeable to those skilled in the art, can be used to accurately monitor the degree of perlecan domain I splice variants in biological fluids as a potential diagnostic indicator and prognostic marker for patients during the progression of disease (ie. monitoring of an amyloid disease for example). Such assays can be provided in a kit form. In addition, quantitative changes in perlecan domain I splice variant autoantibody levels can also serve as a prognostic indicator monitoring how a live patient will respond to treatment which targets a given amyloid disease.

Other diagnostic methods utilizing the invention include diagnostic assays for measuring altered levels of each perlecan domain I splice variant in various tissues compared to normal control tissue samples. Assays used to detect levels of perlecan domain I splice variant protein in a sample derived from a host are well-known to those skilled in the art and included radioimmunoassays, competitive-binding assays, Western blot analysis and preferably ELISA assays (as described above).

Yet another aspect of the present invention is to use the antibodies recognizing each of the perlecan domain I splice variants for labellings, for example, with a radionucleotide, for radioimaging or radioguided surgery, for in vivo diagnosis, and/or for in vitro diagnosis. In one preferred embodiment, radiolabelled nucleic acids or antibodies made (by one skilled in the art) against perlecan domain I splice variants may be used as minimally invasive techniques to locate perlecan domain I splice variants and concurrent amyloid deposits in a living patient. These same imaging techniques could then be used at regular intervals (ie. every 6 months) to monitor the progression of the amyloid disease by following the specific levels of a particular perlecan domain I splice variant.

Yet another aspect of the present invention is to provide a method which can evaluate a compound's ability to alter (diminish or eliminate) the affinity of a given amyloid protein (as described herein) or amyloid precursor protein, to perlecan domain I splice variant protein or perlecan domain I splice variant-derived GAGs. By providing a method of identifying compounds which affect the binding of amyloid proteins, or amyloid precursor proteins to such perlecan domain I splice variant protein or perlecan domain I splice variant derived-GAGs or fragments thereof, the present invention is also useful in identifying compounds which can prevent or impair such binding interaction. Thus, compounds can be identified which specifically affect an event linked with the amyloid formation, amyloid deposition, and/or amyloid persistence condition associated with Alzheimer's disease and other amyloid diseases as described herein.

According to one aspect of the invention, to identify for compounds which inhibit the interaction of amyloid proteins or precursor proteins to perlecan domain I splice variants, either amyloid or a perlecan domain I splice variant is immobilized, and the other of the two is maintained as a free entity. The free entity is contacted with the immobilized entity in the presence of a test compound for a period of time sufficient to allow binding of the free entity to the immobilized entity, after which the unbound free entity is removed. Using antibodies which recognize the free entity, or other means to detect the presence of bound components, the amount of free entity bound to immobilized entity can be measured. By performing this assay in the presence of a series of known concentrations of test compound and, as a control, the complete absence of test compound, the effectiveness of the test compound to impede binding of free entity to immobilized entity can be determined and a quantitative determination of the effect of the test compound on the affinity of free entity to immobilized entity can be made. By comparing the binding affinity of the amyloid-perlecan domain I splice variant complex in the presence of a test compound to the binding affinity of the amyloid-perlecan domain I splice variant complex in the absence of a test compound, the ability of the test compound to modulate the binding can be determined.

In the case in which the amyloid is immobilized, it is contacted with free perlecan domain I splice variant polypeptides, perlecan domain I splice variant derived-GAGs or fragments thereof, in the presence of a series of concentrations of test compound. As a control, immobilized amyloid is contacted with free perlecan domain I splice variant polypeptides, perlecan domain I splice variant derived-GAGs, or fragments thereof in the absence of the test compound. Using a series of concentrations of perlecan domain I splice variant polypeptides, perlecan domain I splice variant derived-GAGs or fragments thereof, the dissociation constant ($K_d$) or other indicators of binding affinity of amyloid-perlecan domain I splice variant binding can be determined. In the assay, after the perlecan domain I splice variant polypeptides, perlecan domain I splice variant derived-GAGs, or fragments thereof is placed in contact with the immobilized amyloid for a sufficient time to allow binding, the unbound perlecan domain I splice variant is removed. Subsequently, the level of perlecan domain I splice variant-amyloid binding can be observed. One method uses perlecan domain I splice variant antibodies, as described in the invention, to detect the amount of specific perlecan domain I splice variants bound to the amyloid or the amount of free perlecan domain I splice variant remaining in solution. This information is used to determine first qualitatively whether or not the test compound can prevent or reduce binding between perlecan domain I splice variant and amyloid. Secondly, the data collected from assays performed using a series of test compound at various concentrations, can be used to measure quantitatively the binding affinity of the perlecan domain I splice variant-amyloid complex and thereby determine the effect of the test compound on the affinity between perlecan domain I splice variant and amyloid. Using this information, compounds can be identified which modulate the binding of perlecan domain I splice variant to amyloid and thereby prevent or reduce the amyloid formation, deposition, accumulation and/or persistence, and the subsequent development and persistence of amyloidosis.

In a preferred embodiment, such screening assays as described above can be employed with either perlecan domain I splice variant protein, polypeptides or fragments thereof as described herein, or with perlecan domain I splice variant GAG chains, the latter of which can be isolated from tissues using procedures known to the art. As an example of perlecan domain I splice variant GAG isolation, perlecan domain I splice variants are first isolated from tissues, such as brain, utilizing the specific perlecan domain I splice variant antibodies described herein, and using procedures known to the art, such as affinity-column chromatography and immunoprecipitation methodology. Isolation of perlecan domain I splice variant GAG chains from perlecan domain I splice variants, for example, can be achieved by use of alkaline borohydride treatment as previously described by Castillo and Templeton (*Biochim. Biophys. Acta* 1136:119–128, 1992), which is entirely incorporated herein by reference.

Therefore a kit for practicing a method for identifying compounds useful for altering binding of perlecan domain I splice variant protein, or perlecan domain I splice variant derived-GAGs, to an immobilized amyloid protein, said kit comprising a) a first container having amyloid protein immobilized upon the inner surface, b) a second container which contains perlecan domain I splice variant protein or perlecan domain I splice variant derived-GAGs dissolved in solution, c) a third container which contains antibodies specific for said perlecan domain I splice variant protein or perlecan domain I splice variant derived-GAGs, said antibodies dissolved in solution, and d) a fourth container which contains labelled antibodies specific for antibodies specific for perlecan domain I splice variant or perlecan domain I splice variant derived-GAGs, said labelled antibodies dissolved in solution.

Therapeutic Applications
Use of Primers and/or Nucleic Acids

Another aspect of the present invention is to provide a potential therapeutic using antisense technology. Antisense technology can be used to control gene expression through triple-helix formation or antisense DNA or RNA, both of which methods are based on the binding of a polynucleotide to DNA or RNA. For example, the 5' coding portion of the polynucleotide sequence, which encodes for the mature polypeptides of the present invention is used to design an antisense RNA oligonucleotide of from about 10 to 40 base pairs in length. A DNA oligonucleotide is designed to be complementary to a region of the gene involved in transcription (Lee et al, *Nucleic Acids Res.* 6:3073, 1979; Cooney et al, *Science* 241:456, 1988; Dervan et al, *Science* 251:1360, 1991), thereby preventing transcription and the production of perlecan domain I splice variants. The antisense RNA oligonucleotide hybridizes to the mRNA in vivo and blocks translation of the mRNA molecule into perlecan domain I splice variants (Okano, *J. Neurochem.* 56:560, 1991). The oligonucleotides described above can also be delivered to cells such that the antisense RNA or DNA may be expressed in vivo to inhibit production of the perlecan domain I splice variants.

The perlecan domain I splice variant polypeptides of the present invention and antagonists which are polypeptides may also be employed in accordance with the present invention by expression of such polypeptides in vivo which is often referred to as "gene therapy". For example, cells from a patient may be engineered with a polynucleotide (DNA or RNA) encoding a polypeptide ex vivo, with the engineered cells then being provided to the patient to be treated with the polypeptide. Such methods are well known in the art. For example, cells may be engineered by procedures known in the art by use of a retroviral particle containing RNA encoding a polypeptide of the present invention.

Use of Peptides and/or Antibodies

Figure 10:
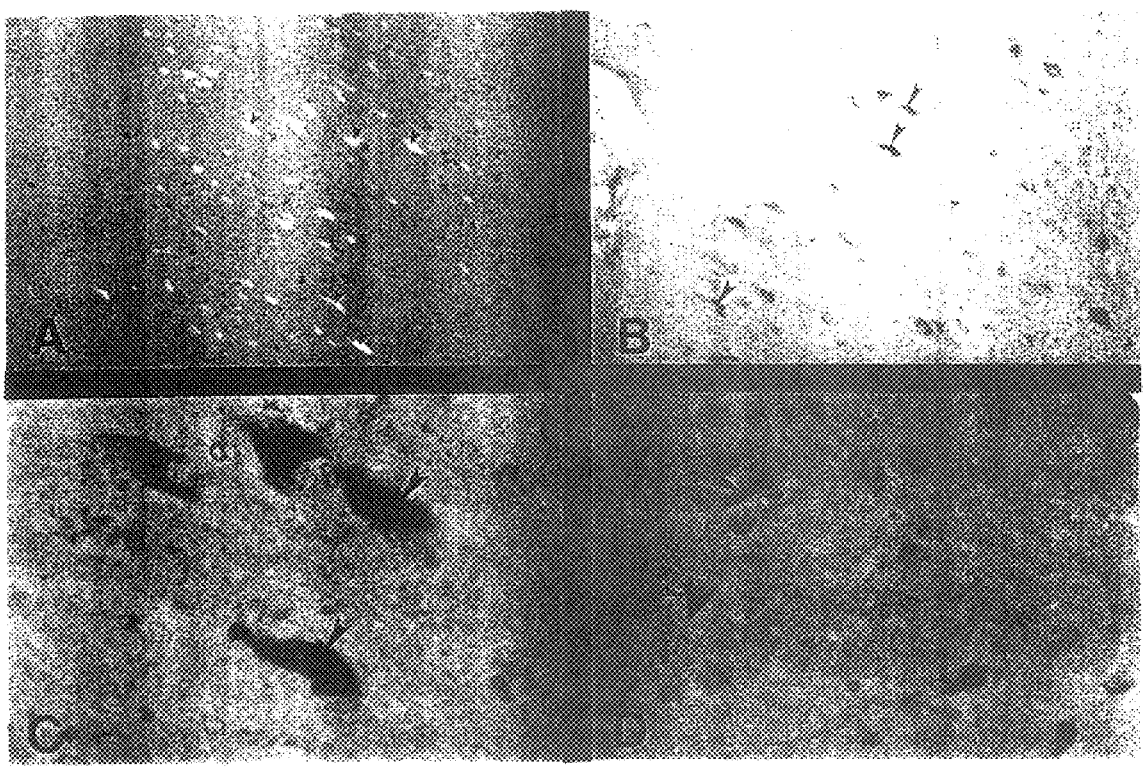
FIG. 10 are black and white photomicrographs demonstrating the localization of Perlecan Domain I variant exon 5 to neurofibrillary tangles in Alzheimer's disease brain utilizing the "exon 5 deletion" antibody.

Yet another aspect of the present invention is to make use of peptides or fragments thereof which are specifically against new sequences of the perlecan domain I splice variants as shown in FIG. 4C (SEQ ID NO: 4), FIG. 6C (SEQ ID NO: 10), FIG. 7C (SEQ ID NO: 13), FIG. 9 (SEQ ID NO: 15), and FIG. 10 (SEQ ID NO: 16). In addition, a peptide or fragment thereof made against the new exon 3 to exon 6.5 junction, as shown in FIG. 5C (SEQ ID NO: 7) can be utilized. The peptide sequences or fragments can by synthesized utilizing standard techniques (ie. using an automated synthesizer). The peptides can be used as potential blocking therapeutics for the interaction of the perlecan domain I splice variants in a number of biological processes and diseases (such as in the amyloid diseases described above). In a preferred embodiment, specific peptides made against the new sequences contained within one or more of the perlecan domain I splice variants may be used to block the interaction of these variants with a given target (ie. amyloid deposits). Inhibition by these peptides may alleviate the continued amyloid formation, deposition, accumulation and/or persistence observed in a given patient. Likewise, in another preferred embodiment antibodies made against each of the perlecan domain I splice variants (as described above) may be given to a human patient as potential blocking antibodies to disrupt continued amyloid formation, deposition, accumulation and/or persistence in the given patient.

Preparations of perlecan domain I splice variant polypeptides for parenteral administration include sterile aqueous or non-aqueous solutions, suspensions, and emulsions, which may contain auxiliary agents or excipients which are known in the art. Pharmaceutical compositions such as tablets, pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to routine methods and are known in the art.

In yet another aspect of the invention, the perlecan domain I variant antibodies may be used as an effective therapy to block perlecan domain I splice variant and hence amyloid formation, deposition, accumulation and/or persistence as observed in the amyloid diseases. For example, the invention includes a pharmaceutical composition for use in the treatment of amyloidoses comprising a pharmaceutically effective amount of a perlecan domain I splice variant antibody and a pharmaceutically acceptable carrier. The compositions may contain the perlecan domain I splice variant antibody, either unmodified, conjugated to a potentially therapeutic compound, conjugated to a second protein or protein portion or in a recombinant form (ie. chimeric or bispecific perlecan domain I variant antibody). The compositions may additionally include other antibodies or conjugates. The antibody compositions of the invention can be administered using conventional modes of administration including, but not limited to, topical, intravenous, intra-arterial, intraperitoneal, oral, intralymphatic or intramuscular. Intravenous administration is preferred. The compositions of the invention can be a variety of dosage forms, with the preferred form depending upon the mode of administration and the therapeutic application. Optimal dosage and modes of administration for an individual patient can readily be determined by conventional protocols.

Perlecan domain I splice variant polypeptides, or antibodies of the present invention may be administered by any means that achieve their intended purpose, for example, to treat perlecan domain I splice variant related pathologies, such as Alzheimer's disease and other amyloid diseases, or other related pathologies, using a perlecan domain I splice variant polypeptide described herein, in the form of a pharmaceutical composition.

For example, administration of such a composition may be by various parenteral routes such as subcutaneous, intravenous, intradermal, intramuscular, intraperitoneal, intranasal, transdermal or buccal routes. Alternatively, or concurrently, administration may be by the oral route. Parenteral administration can be by bolus injection or by gradual perfusion over time.

A preferred mode of using a perlecan domain I splice variant polypeptides, or antibody pharmaceutical composition of the present invention is by oral administration or intravenous application.

A typical regimen for preventing, suppressing or treating perlecan domain I splice variant-related pathologies, such as comprises administration of an effective amount of a perlecan domain I splice variant polypeptide, administered over a period of one or several days, up to and including between one week and about 24 months.

It is understood that the dosage of the perlecan domain I splice variant polypeptide of the present invention administered in vivo or in vitro will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

The total dose required for each treatment may be administered by multiple doses or in a single dose. A perlecan domain I splice variant polypeptide may be administered alone or in conjunction with other therapeutics directed to perlecan domain I splice variant-related pathologies, such as Alzheimer's disease or amyloid diseases, as described herein.

Effective amounts of a perlecan domain I splice variant polypeptide or composition, which may also include a perlecan domain I splice variant antibody, are about 0.01 $\mu$g to about 100 mg/kg body weight, and preferably from about 10 $\mu$g to about 50 mg/kg body weight, such as 0.05, 0.07, 0.09, 0.1, 0.5, 0.7, 0.9., 1, 2, 5, 10, 20, 25, 30, 40, 45, 50, 55, 60, 65, 70, 75, 80, 85, 90, 95 or 100 mg/kg.

Preparations for parenteral administration include sterile aqueous or non-aqueous solutions, suspensions, and emulsions, which may contain auxiliary agents or excipients which are known in the art. Pharmaceutical compositions comprising at least one perlecan domain I splice variant polypeptide, such as 1–10 or 1, 2, 3, 4, 5, 6, 7, 8, 9, or 10 perlecan domain I splice variant polypeptides, of the present invention may include all compositions wherein the perlecan domain I splice variant polypeptide is contained in an amount effective to achieve its intended purpose. In addition to at least one perlecan domain I splice variant polypeptide, a pharmaceutical composition may contain suitable pharmaceutically acceptable carriers, such as excipients, carriers and/or auxiliaries which facilitate processing of the active compounds into preparations which can be used pharmaceutically.

Pharmaceutical compositions comprising at least one perlecan splice variant polypeptide or antibody may also include suitable solutions for administration intravenously, subcutaneously, dermally, orally, mucosally, rectally or may by injection or orally, and contain from about 0.01 to 99 percent, preferably about 20 to 75 percent of active component (i.e. polypeptide or antibody) together with the excipient. Pharmaceutical compositions for oral administration include pills, tablets, caplets, soft and hard gelatin capsules, lozenges, sachets, cachets, vegicaps, liquid drops, elixers, suspensions, emulsions, solutions, and syrups.

Use of Perlecan Domain I Splice Variants for Production of New Animal Models

Infusion Models for Alzheimer's Disease and Down's Syndrome Amyloidosis

The production of each of the perlecan domain I splice variants in sufficient quantities can also be utilized to produce new animal models of the amyloidoses. For purposes of this application, perlecan domain I splice variants can refer to a) perlecan variants which contain both core protein and attached GAG chains, b) perlecan core protein only, or c) perlecan GAG chains derived from perlecan splice variants, or any fragments or combinations of any of the above. For example, as a new model of Alzheimer's disease amyloidosis, perlecan domain I splice variants can be continuously infused in combination with beta-amyloid protein (A$\beta$) into the hippocampus of groups of rats or mice. In a preferred embodiment perlecan domain I splice variant (25 $\mu$g) is dissolved in water in a microcentrifuge tube containing 50 $\mu$g of A$\beta$ (1–40) or (1–42). Using the described methods of Snow et al (*Neuron* 12:219–234, 1994) herewith incorporated by reference, the perlecan domain I splice variant+A$\beta$ is continuously infused for 1 week into hippocampus (via stereotaxic surgeries knowledgeable by one skilled in the art) of groups (usually 10) of 3 month old Sprague-Dawley rats. Following the 1 week infusion the animals are sacrificed and the brains are removed as described in Snow et al (*Neuron* 12:219–234, 1994), and 6–8 $\mu$m serial sections spanning through the entire infusion site are cut from paraffin embedded blocks or from frozen sections. The extent of amyloid deposition per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of fibrillar A$\beta$ amyloid deposition, accumulation and persistence in vivo. In addition, this model may be used to rapidly screen potential therapeutics targeting fibrillar A$\beta$ amyloid formation, deposition, accumulation and/or persistence. In a preferred embodiment, perlecan domain I splice variant+A$\beta$+ therapeutic compound is directly infused into the hippocampus (as described above) of a group of animals and comparisons are made to a group of animals infused with only perlecan domain I splice variant+A$\beta$. Compounds or drugs found to reduce amyloid formation, deposition, accumulation and/or persistence (as determined by Congo red or Thioflavin S scoring) in vivo are then identified as having potential therapeutic value.

In another preferred embodiment, the potentially therapeutic compound can be tested to reduce amyloid persistence over prolonged periods of time. In this model, groups of animals (usually 10 animals per group) are infused with perlecan domain I splice variant+A$\beta$+therapeutic compound and directly compared to groups of animals (usually 10 animals per group) infused with perlecan domain I splice variant+A$\beta$. Following a 1 week infusion (as described above), the cannulae are removed with the animals under anesthesia, and the animals are then allowed to recover until sacrifice 1, 3, 6 or 12 months later. Serial sections are cut and amyloid is scored as described above. It is expected that persistent amyloid deposits can be observed in animals infused with the perlecan domain I splice variant+A$\beta$. Potent therapeutic compounds are those that effectively reduce the amount of amyloid observed in comparison to those animals not given the therapeutic compound. These compounds can therefore be referred to as compounds which effectively reduce amyloid persistence in vivo.

In yet another preferred embodiment, potentially therapeutic compounds can be tested for reducing or eliminating pre-formed amyloid deposits. In this model, two groups of animals (usually 10 animals per group) are infused with perlecan domain I splice variant+Aβ. Following a 1 week infusion (as described above), the cannulae and osmotic pumps are changed (with the animals under anesthesia), and a new cannulae connected by vinyl tubing to a new osmotic pump, contains either vehicle only (ie. double distilled water) or the potential therapeutic compound. Following a 1 week continuous infusion of either the vehicle or the potential therapeutic compound of interest, the animals are sacrificed. Serial sections are then cut through the entire infusion site and the extent of amyloid is measured by arbitrary blind scoring as described above. Potent therapeutic compounds are those that are able to effectively remove pre-formed arnyloid deposits. It is expected that little to no reduction in the amount of amyloid will be observed in the group of animals infused with vehicle only. These compounds can therefore be referred to as therapeutic compounds which effectively reduce pre-formed amyloid deposits in vivo.

New Animal Models of AA Amyloidosis

The production of each of the perlecan domain I splice variants in sufficient quantities can also be utilized to produce a new animal model of AA amyloidosis. For example, perlecan domain I splice variants can be continuously infused into systemic organs (ie. kidney, liver, spleen, lung or heart) or injected daily into the tail veins of rats or mice, in combination with AA amyloid protein. In a preferred embodiment perlecan domain I splice variant is dissolved in water in a microcentrifuge tube containing AA amyloid protein. Using the described methods of Snow et al (*Neuron* 12:219–234, 1994), the perlecan domain I splice variant+AA amyloid is continuously infused for 1 week into a systemic organ of choice (via stereotaxic surgeries knowledgeable by one skilled in the art) of groups (usually 10) of adult rats or mice. Alternatively, AA amyloid protein+/−perlecan domain I splice variant is injected daily into the tail veins of a group of rats or mice. Following the 1 week experimental period, the animals are sacrificed and the systemic organs are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of fibrillar AA amyloid deposition, accumulation and persistence in vivo. In addition, this model may be used to rapidly screen potential therapeutics targeting AA amyloid formation, deposition, accumulation and/or persistence. In a preferred embodiment, perlecan domain I splice variant+AA amyloid+therapeutic compound is directly infused or injected (as described above) into a group of animals and comparisons are made to a group of animals infused or injected with only perlecan domain I splice variant+Aβ. Compounds or drugs found to reduce amyloid formation, deposition, accumulation and/or persistence (as determined by Congo red or Thioflavin S scoring) in vivo are then identified as having potential therapeutic value.

New Animal Models of AL Amyloidosis

The production of each of the perlecan domain I splice variants in sufficient quantities can also be utilized to produce a new animal model of AL amyloidosis. For example, perlecan domain I splice variants can be continuously infused into systemic organs (ie. kidney, liver, spleen, lung or heart) or injected daily into the tail veins of rats or mice, in combination with AL amyloid protein. In a preferred embodiment perlecan domain I splice variant is dissolved in water in a microcentrifuge tube containing AA amyloid protein. Using the described methods of Snow et al (*Neuron* 12:219–234, 1994), the perlecan domain I splice variant+AL amyloid is continuously infused for 1 week into a systemic organ of choice (via stereotaxic surgeries knowledgeable by one skilled in the art) of groups (usually 10) of adult rats or mice. Alternatively, AL amyloid protein+/−perlecan domain I splice variant is injected daily into the tail veins of a group of rats or mice. Following the 1 week experimental period, the animals are sacrificed and the systemic organs are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of fibrillar AL amyloid deposition, accumulation and persistence in vivo. In addition, this model may be used to rapidly screen potential therapeutics targeting AL amyloid formation, deposition, accumulation and/or persistence. In a preferred embodiment, perlecan domain I splice variant+AL amyloid+therapeutic compound is directly infused or injected (as described above) into a group of animals and comparisons are made to a group of animals infused or injected with only perlecan domain I splice variant+AL amyloid. Compounds or drugs found to reduce amyloid formation, deposition, accumulation and/or persistence (as determined by Congo red or Thioflavin S scoring) in vivo are then identified as having potential therapeutic value.

New Animal Models of Transthyretin/Prealbumin Amyloidosis

The production of each of the perlecan domain I splice variants in sufficient quantities can also be utilized to produce a new animal model of transthyretin/prealbumin amyloidosis. For example, perlecan domain I splice variants can be continuously infused or injected daily into the sciatic nerve, dorsal root ganglion or autonomic ganglion of rats or mice, in combination with various normal or mutated transthyretin/prealbumin proteins. In a preferred embodiment perlecan domain I splice variant is dissolved in water in a microcentrifuge tube containing of normal or mutated transthyretin/ prealbumin proteins. Using the described methods of Snow et al (*Neuron* 12:219–234, 1994), the perlecan domain I splice variant+normal or mutated transthyretin/ prealbumin amyloid is continuously infused for 1 week into sciatic nerve, dorsal root ganglion or autonomic ganglion (via stereotaxic surgeries knowledgeable by one skilled in the art) of groups (usually 10) of adult rats or mice. Alternatively, normal or mutated transthyretin/ prealbumin+/−perlecan domain I splice variant are injected daily into sciatic nerve, dorsal root ganglion or autonomic ganglion of a group of rats or mice. Following the 1 week experimental period, the animals are sacrificed and the pertinent tissues are removed, and 6–8 μm serial sections are cut from paraffin embedded blocks or from frozen sections containing the tissues of interest.The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of fibrillar transthyretin/prealbumin amyloid deposition, accumulation and persistence in vivo. In addition, this model may be used to rapidly screen potential therapeutics targeting transthyretin/prealbumin amyloid formation, deposition, accumulation and/or persistence. In a preferred embodiment, perlecan domain I splice variant+normal or mutated transthyretin/prealbumin+therapeutic compound is directly infused or injected (as described above) into a group of animals and comparisons are made to a group of animals infused or injected with only perlecan domain I splice variant+normal or mutated transthyretin/prealbumin. Compounds or drugs found to reduce amyloid formation, deposition, accumulation and/or persistence (as determined by Congo red or Thioflavin S scoring) in vivo are then identified as having potential therapeutic value.

New Animal Models of Beta$_2$-Microglobulin Amyloidosis

The production of each of the perlecan domain I splice variants in sufficient quantities can also be utilized to produce a new animal model of beta$_2$-microglobulin amyloidosis. For example, perlecan domain I splice variants can be continuously infused into the bloodstream (for example, through external jugular vein to superior vena cava) or injected daily into the tendon or hind leg (adjacent to the medial nerve) of rats or mice, in combination with beta$_2$-microglobulin. In a preferred embodiment perlecan domain I splice variant is dissolved in water in a microcentrifuge tube containing beta$_2$-microglobulin. Using the described methods of Snow et al (*Neuron* 12:219–234, 1994), the perlecan domain I splice variant+beta$_2$-microglobulin is continuously infused for 1 week into the bloodstream (via stereotaxic surgeries knowledgeable by one skilled in the art) of groups (usually 10) of adult rats or mice. Alternatively, beta$_2$-microglobulin+/−perlecan domain I splice variant are injected daily into the tendon or hind leg of a group of rats or mice. Following the 1 week experimental period, the animals are sacrificed and the pertinent tissues are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of beta$_2$-microglobulin amyloid deposition, accumulation and persistence in vivo. In addition, this model may be used to rapidly screen potential therapeutics targeting beta$_2$-microglobulin amyloid formation, deposition, accumulation and/or persistence. In a preferred embodiment, perlecan domain I splice variant+beta$_2$-microglobulin+therapeutic compound is directly infused or injected (as described above) into a group of animals and comparisons are made to a group of animals infused or injected with only perlecan domain I splice variant+beta$_2$-microglobulin. Compounds or drugs found to reduce amyloid formation, deposition, accumulation and/or persistence (as determined by Congo red or Thioflavin S scoring) in vivo are then identified as having potential therapeutic value.

New Animal Models of Amylin (Islet Amyloid) Amyloidosis

The production of each of the perlecan domain I splice variants in sufficient quantities can also be utilized to produce a new animal model of amylin (islet amyloid) amyloidosis. For example, perlecan domain I splice variants can be continuously infused or daily injected into the pancreas or bloodstream of rats or mice, in combination with human amylin. In a preferred embodiment perlecan domain I splice variant is dissolved in water in a microcentrifuge tube containing amylin. Using the described methods of Snow et al (*Neuron* 12:219–234, 1994), the perlecan domain I splice variant+amylin is continuously infused or daily injected for 1 week into the pancreas or bloodstream (via stereotaxic surgeries knowledgeable by one skilled in the art) of groups (usually 10) of adult rats or mice. Following the 1 week experimental period, the animals are sacrificed and the pancreas is removed, and 6–8 μm serial sections are cut from paraffin embedded blocks or from frozen sections containing the pancreas. The extent of amyloid deposition in the pancreas per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of amylin (islet amyloid) deposition, accumulation and persistence in vivo. In addition, this model may be used to rapidly screen potential therapeutics targeting amylin (islet amyloid) formation, deposition, accumulation and/or persistence. In a preferred embodiment, perlecan domain I splice variant+amylin+therapeutic compound is directly infused or injected (as described above) into a group of animals and comparisons are made to a group of animals infused or injected with only perlecan domain I splice variant+amylin. Compounds or drugs found to reduce amyloid formation, deposition, accumulation and/or persistence (as determined by Congo red or Thioflavin S scoring) in vivo are then identified as having potential therapeutic value.

New Animal Models of Endocrine Type Amyloidosis

The production of each of the perlecan domain I splice variants in sufficient quantities can also be utilized to produce a new animal model of endocrine amyloidosis, such as observed when a variant of calcitonin is found in the amyloid of medullary carcinoma of the thyroid, as well as in the islets of Langerhans in the pancreas of patients with type II (non-insulin dependent) diabetes. For example, perlecan domain I splice variants can be continuously infused or daily injected into the thyroid gland or pancreas of rats or mice, in combination with calcitonin. In a preferred embodiment perlecan domain I splice variant is dissolved in water in a microcentrifuge tube containing calcitonin. Using the described methods of Snow et al (*Neuron* 12:219–234, 1994), the perlecan domain I splice variant+calcitonin is continuously infused or daily injected for 1 week into the thyroid gland or pancreas (via stereotaxic surgeries knowledgeable by one skilled in the art) of groups (usually 10) of adult rats or mice. Following the 1 week experimental period, the animals are sacrificed and the thyroid gland or pancreas is removed, and 6–8 μm serial sections are cut from paraffin embedded blocks or from frozen sections containing the thyroid gland or pancreas. The extent of amyloid deposition in the thyroid gland or pancreas per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of endocrine amyloid deposition, accumulation and persistence in vivo. In addition, this model may be used to rapidly screen potential therapeutics targeting endocrine amyloid formation, deposition, accumulation and/or persistence. In a preferred embodiment, perlecan domain I splice variant+calcitonin+therapeutic compound is directly infused or injected (as described above) into a group of animals and comparisons are made to a group of animals infused or injected with only perlecan domain I splice variant+calcitonin. Compounds or drugs found to reduce amyloid formation, deposition, accumulation and/or persistence (as determined by Congo red or Thioflavin S scoring) in vivo are then identified as having potential therapeutic value.

New Animal Models of PrP Amyloidosis

The production of each of the perlecan domain I splice variants in sufficient quantities can also be utilized to produce a new animal model of prion protein (PrP) amyloidosis. For example, perlecan domain I splice variants can be continuously infused in combination with PrP protein into the hippocampus of groups of rats or mice. In a preferred embodiment perlecan domain I splice variant is dissolved in water in a microcentrifuge tube containing PrP 27–30. Using the described methods of Snow et al (*Neuron* 12:219–234, 1994), the perlecan domain I splice variant+PrP is continuously infused for 1 week into hippocampus (via stereotaxic surgeries knowledgeable by one skilled in the art) of groups (usually 10) of adult rats or mice. Following the 1 week infusion the animals are sacrificed and the brains are removed as described in Snow et al (*Neuron* 12:219–234, 1994), and 6–8 µm serial sections spanning through the entire infusion site are cut from paraffin embedded blocks or from frozen sections. The extent of amyloid deposition per animal is then detected by Congo red staining (as viewed under polarized light) or Thioflavin S fluorescence and quantitated in a blind study using an arbitrary scoring method as described by Snow et al (*Neuron* 12:219–234, 1994). The use of the perlecan domain I splice variant peptides and/or proteins in this model can be used as a rapid model of PrP amyloid deposition, accumulation and persistence in vivo. In addition, this model may be used to rapidly screen potential therapeutics targeting PrP amyloid formation, deposition, accumulation and/or persistence. In a preferred embodiment, perlecan domain I splice variant+PrP 27–30+therapeutic compound is directly infused into the hippocampus (as described above) of a group of animals and comparisons are made to a group of animals infused with only perlecan domain I splice variant+PrP 27–30. Compounds or drugs found to reduce amyloid formation, deposition, accumulation and/or persistence (as determined by Congo red or Thioflavin S scoring) in vivo are then identified as having potential therapeutic value.

Perlecan Domain I Splice Variant Transgenic Animals

In accordance with the disclosure of means and methods of making transgenic animals, in particular transgenic mice, which disclosure is found in U.S. patent application Ser. No. 08/870.987 by K. Fukuchi, A. Snow and J. Hassell, filed Jun. 6, 1997, and which is hereby incorporated by this reference as if fully set forth, another aspect of the invention is to produce new transgenic animals that overexpress or knock-out a particular perlecan domain I splice variant in an effort to produce specific phenotypes associated with a number of diseases and/or pathological processes. For the production of these new perlecan domain I splice variant transgenic animals, this would generally involve ligating the splice variant cDNA sequence from the plasmid clones (described herein) into the correct region of normal human perlecan cDNA (available in an expression vector with correct promoter and enhancer regions as described in the incorporated reference above). The perlecan splice variant expression vector would then be inserted into mouse eggs or embryonic stem cells and transgenic mice would be produced through known, routine methods as described in the incorporated reference above. Production of these transgenic mice, and the mating of these mice with transgenic animals which overexpress a given amyloid protein or its precursor protein, will produce progeny that develop much or all of the phenotypic pathology of a given amyloid disease. The production of new transgenic animal models of amyloid diseases may be used as in vivo screening tools to aid in the identification of lead therapeutics for the amyloidoses and for the treatment of clinical manifestations associated with these diseases (as described in the incorporated reference above). The successful overproduction of perlecan domain I splice variants in transfected cells also serves as a new means to isolate these perlecan domain I splice variants which will meet the increasing demands for use of perlecan domain I splice variants for a variety of in vitro and in vivo assays.

What we claim is:

1. An isolated polynucleotide comprising a splice variant of perlecan formed by a partial or complete deletion of a number of exons within domain I of perlecan, the number of exons deleted from domain I numbering less than the number of exons in domain I.

2. The polynucleotide of claim 1 comprising the 573 nucleotides of SEQ ID NO: 1 or a fragment thereof.

3. The polynucleotide of claim 1 comprising the 219 nucleotides of SEQ ID NO: 2 or a fragment thereof.

4. The polynucleotide of claim 1 comprising the 312 nucleotides of SEQ ID NO: 6 or a fragment thereof.

5. The polynucleotide of claim 1 wherein the polynucleotide is cDNA or genomic DNA.

6. The polynucleotide of claim 1 wherein the polynucleotide is synthetic DNA.

7. The polynucleotide of claim 1 wherein the polynucleotide is RNA.

8. The polynucleotide of claim 1 which encodes a polypeptide which contains a consensus sequence for a glycosaminoglycan attachment site, wherein the sequence is Ser-Gly or Ser-Gly-Asp.

9. The polynucleotide of claim 8 which encodes the polypeptide as set forth in SEQ ID NO: 3 or a fragment thereof.

10. An isolated polynucleotide comprising a splice variant of perlecan formed by an insertion of nucleotides within domain I of perlecan such that the isolated polynucleotide is comprised of domain I plus the inserted nucleotides.

11. The polynucleotide of claim 10 comprising the 33 nucleotides of SEQ ID NO: 9 or a fragment thereof.

12. The polynucleotide of claim 10 comprising the 75 nucleotides of SEQ ID NO: 12 or a fragment thereof.

13. The polynucleotide of claim 10 wherein the polynucleotide is cDNA or genomic DNA.

14. The polynucleotide of claim 10 wherein the polynucleotide is synthetic DNA.

15. The polynucleotide of claim 10 wherein the polynucleotide is RNA.

16. The polynucleotide of claim 10 which encodes a polypeptide which contains a consensus sequence for a glycosaminoglycan attachment site, wherein the sequence is Ser-Gly or Ser-Gly-Asp.

17. A method of detection and/or quantitation of a splice variant of perlecan domain I gene in a sample, the method comprising making complementary DNA (cDNA) from messenger RNA (mRNA) in the sample, amplifying portions of the cDNA corresponding to the perlecan gene or parts thereof and detecting and quantifying the amplified cDNA in order to detect or quantify the splice variant.

18. The method of claim 7, wherein the sample assayed is RNA derived from tissues, cells and/or cells in biological fluids.

19. The method of claim 17 wherein said tissues, cells and/or cells in biological fluids are derived from humans.

20. The method of claim 18 wherein said biological fluids are selected from a group of biological fluids consisting of blood, plasma, serum, cerebrospinal fluid, sputum, saliva, urine and stool.

21. The method of claim 17 wherein primers are utilized to amplify and detect a perlecan domain I splice variant, and the primers are selected from one or both primers in a SEQ ID primer pair selected from the group of SEQ ID's primer pairs consisting of SEQ ID NO: 5 and SEQ ID NO: 17, SEQ ID NO: 8 and SEQ ID NO: 18, SEQ ID NO: 11 and SEQ ID NO: 19 and SEQ ID NO: 14 and SEQ ID NO: 20.

22. The method of claim 17 whereby said method utilizes quantitative competitive RT techniques followed by PCR techniques to determine relative quantitative levels of a perlecan domain I splice variant in RNA.

\* \* \* \* \*

UNITED STATES PATENT AND TRADEMARK OFFICE
CERTIFICATE OF CORRECTION

PATENT NO. : 6,432,636 B1
DATED : August 13, 2002
INVENTOR(S) : Grace A. Maresh et al.

It is certified that error appears in the above-identified patent and that said Letters Patent is hereby corrected as shown below:

Column 66,
Line 33, change "claim 7" to -- claim 17 --.

Signed and Sealed this

Twenty-ninth Day of October, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,432,636 B1
APPLICATION NO. : 08/918428
DATED : August 13, 2002
INVENTOR(S) : Grace Maresh It is certified that error appears in the above-identified patent and that said Letters Patent is hereby corrected as shown below:

Col. 1 Lines 2-3 insert
--This invention was made with government support under RO1 AG12953-02 awarded by NIH. The government has certain rights in the invention.--

Signed and Sealed this

Twenty-eighth Day of August, 2007

JON W. DUDAS
*Director of the United States Patent and Trademark Office*